(12) United States Patent
Zhang

(10) Patent No.: US 11,680,042 B2
(45) Date of Patent: Jun. 20, 2023

(54) COMPOUNDS, REAGENTS, AND USES THEREOF

(71) Applicant: Metabolon, Inc., Morrisville, NC (US)

(72) Inventor: Qibo Zhang, Cary, NC (US)

(73) Assignee: Metabolon, Inc., Morrisville, NC (US)

( * ) Notice: Subject to any disclaimer, the term of this patent is extended or adjusted under 35 U.S.C. 154(b) by 470 days.

(21) Appl. No.: 16/650,429

(22) PCT Filed: Sep. 27, 2018

(86) PCT No.: PCT/US2018/053091
§ 371 (c)(1),
(2) Date: Mar. 25, 2020

(87) PCT Pub. No.: WO2019/067699
PCT Pub. Date: Apr. 4, 2019

(65) Prior Publication Data
US 2020/0231541 A1  Jul. 23, 2020

Related U.S. Application Data

(60) Provisional application No. 62/564,558, filed on Sep. 28, 2017.

(51) Int. Cl.
| | | |
|---|---|---|
| *C07C 323/54* | (2006.01) | |
| *C07C 319/18* | (2006.01) | |
| *C07K 16/44* | (2006.01) | |
| *G01N 30/72* | (2006.01) | |

(52) U.S. Cl.
CPC .......... *C07C 323/54* (2013.01); *C07C 319/18* (2013.01); *C07K 16/44* (2013.01); *G01N 30/7233* (2013.01)

(58) Field of Classification Search
CPC ... C07C 323/54; C07C 319/18; C07C 201/00; C07C 319/12; C07K 16/44; G01N 30/7233; G01N 33/6893; G01N 33/6848
See application file for complete search history.

(56) References Cited

FOREIGN PATENT DOCUMENTS

WO    2016/025429 A1    2/2016
WO    WO-2016025429 A1 *  2/2016 ............ G01N 21/62

OTHER PUBLICATIONS

Sela-Culang, et al. Front. in Immunol. 2013 vol. 4, Article 302 (Year: 2013).*
Almagro & Fransson, Frontiers in Bioscience 2008; 13:1619-33 (Year: 2008).*
Marchalonis et al., Dev & Comp Immunol 30:223-247 (2006) (Year: 2006).*
Edwards et al, J Mol Biol 334:103-118 (2003) (Year: 2003).*
Zhang, et al., Org. Letter 2018, 20, 2100-2103 (Year: 2018).*
Baird, et al., Measuring Kinetic Isotope Effects of Carbon at Natural Abundance 2002, URL: https://chemistry.illinois.edu/system/files/inline-files/Abstract_Baird1.pdf; Accessed Jul. 29, 2022 (Year: 2002).*
Zhang et al., Identification of an Endogenous Organosulfur Metabolite by Interpretation of Mass Spectrometric Data. Org Lett. 2018;20(7):2100-2103.
International Search Report and Written Opinion for Application No. PCT/US2018/053091, dated Jan. 3, 2019, 8 pages.

* cited by examiner

*Primary Examiner* — Julie Wu
*Assistant Examiner* — John L Van Druff
(74) *Attorney, Agent, or Firm* — McCarter & English, LLP; Anita M. Bowles; Xin Zhang

(57) ABSTRACT

The present invention provides a compound of formula (I), formula (II), formula (III), (IV) or a salt thereof, compositions and methods of making the compound, methods and reagents for measuring the compound, and kits using the same. The use of a compound of formula (I), formula (II), formula (III), or formula (IV) for assessing or monitoring kidney function in a subject, determining predisposition to developing reduced kidney function, classifying a subject according to level of kidney function, and diagnosing or monitoring chronic kidney disease is also described.

20 Claims, 45 Drawing Sheets

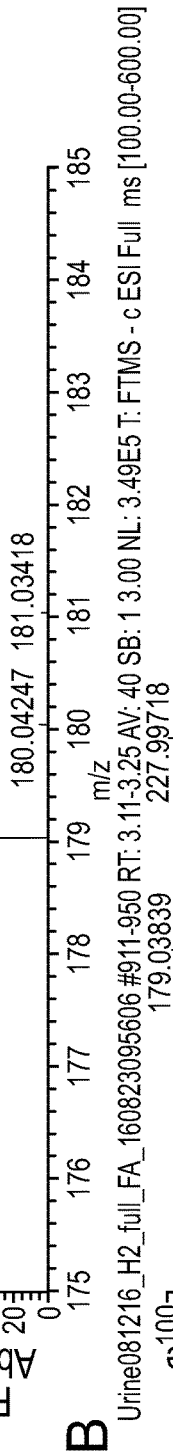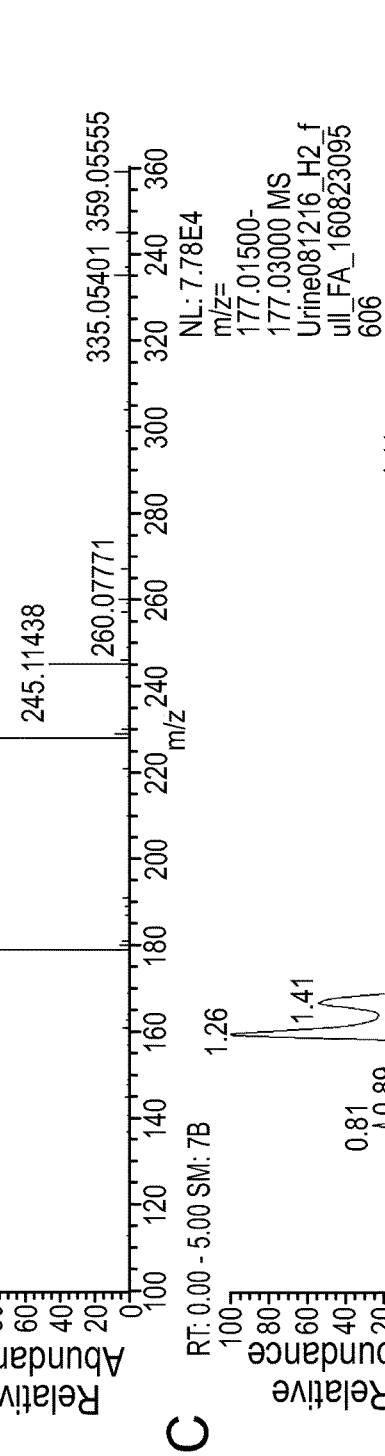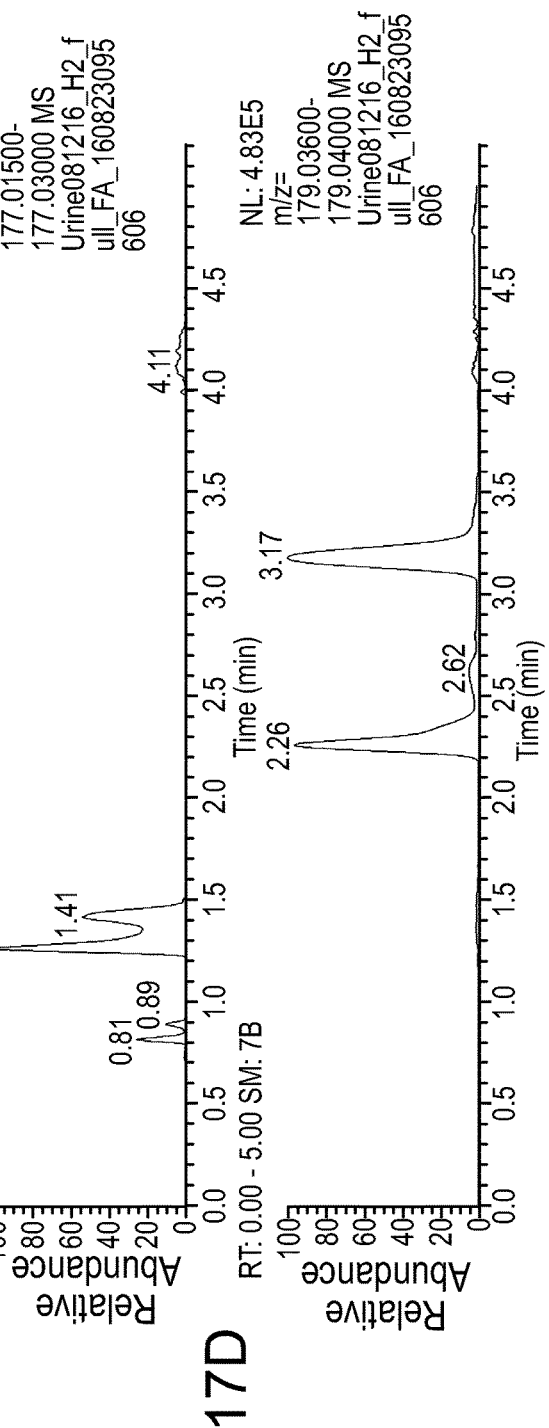
FIG. 17A
FIG. 17B
FIG. 17C
FIG. 17D

COMPOUNDS, REAGENTS, AND USES THEREOF

RELATED APPLICATIONS

This application is a 35 U.S.C. § 371 national stage filing of International Application No. PCT/US2018/053091, filed on Sep. 27, 2018, which claims the benefit of the filing date under 35 U.S.C. § 119(e), of U.S. Provisional Application No. 62/564,558, filed on Sep. 28, 2017. The entire contents of each of the foregoing applications, including all drawings, formulae, specifications, and claims, are incorporated herein by reference.

BACKGROUND OF THE INVENTION

The following information to describe the background of the invention is provided to assist the understanding of the invention and is not admitted to constitute or describe prior art to the invention.

Kidney function is traditionally assessed using the glomerular filtration rate (GFR). While the gold standard methodology, measured GFR (mGFR), is precise and accurate, its utility is limited due to the complex, time-consuming, and invasive nature of the test. It is also an expensive test to perform. As a result, GFR is estimated clinically using equations based on concentrations of endogenous filtration markers, creatinine and Cystatin C, measured in serum. Currently used equations for estimating GFR (eGFR) (MDRD, CKD-EPI) include demographic variables (age, sex, race) as surrogates for factors unrelated to kidney function/GFR that influence serum levels of creatinine and Cystatin C. However, these eGFR equations show limited accuracy and precision versus mGFR.

Current markers may have limited utility because demographic variables are poor surrogates for non-GFR determinants (e.g., muscle mass for creatinine, adiposity for Cystatin C), certain patients are inappropriately categorized (e.g., multiracial, transgender, intersex), and local sensitivity to reporting (e.g., race). Due to limitations with current eGFR markers, alternative endogenous filtration markers with low molecular weight that are freely filtered by the glomerula and are not (or only minimally) affected by non-GFR determinants have been identified. These alternative markers may also be independent from demographic variables, thereby overcoming limitations associated with using these variables.

Described herein are methods for the synthesis, isolation, detection, and quantitation of an endogenous small molecule filtration marker ((2R,3R)-2,3-dihydroxy-5-methylthio-trans-4-pentenoic acid, DMTPA) in a biological sample. The analyte/marker, was previously discovered as X-11564, a marker associated with GFR and kidney function, but the structure was unknown which limited its utility. Here we report the structure of this molecule and provide methods of synthesis of the compound, methods of measuring (including measuring individually or as part of a panel of markers), reagents for measuring (e.g., internal standards, antibodies), and kits using the same.

SUMMARY OF THE INVENTION

The present invention provides novel compounds and compositions, synthetic methods and methods for detecting the amount of the compound in a biological sample which may be useful in assessing and monitoring kidney function as well as diagnostic methods for kidney diseases.

In one embodiment, the present invention provides a compound represented by formula (I):

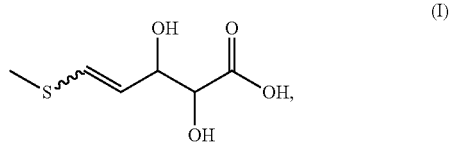

or a salt thereof, wherein the compound is at least 60%, 70%, 80%, 90%, 95%, 99%, 99.5% or 99.9% pure.

In another embodiment, the present invention provides a compound represented by formula (II):

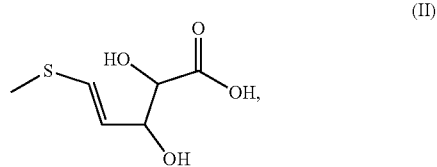

or a salt thereof, wherein the compound is at least 60%, 70%, 80%, 90%, 95%, 99%, 99.5% or 99.9% pure.

In another embodiment, the present invention provides a method for determining the level of a compound of formula I or formula II or salt thereof using an assay.

In another embodiment, the present invention provides a method for determining the level of a compound of formula I or formula II or salt thereof, in a subject comprising: (1) preparing an analytical sample from a biological sample obtained from the subject; and (2) determining the level of the compound using chromatography, mass spectrometry, enzyme-linked immunosorbent assay (ELISA), antibody linkage, immunoblotting, immunohistochemistry (IHC), other immunochemical methods, or a combination thereof.

In an aspect of the invention, a method comprises detecting and determining the amount of a compound of formula I or formula II or a salt thereof in a sample by mass spectrometry. In another aspect, a method comprises detecting and determining the amount of a compound of formula I or formula II or a salt thereof and one or more of a panel of analytes comprised of one or more analytes selected from the group consisting of pseudouridine, N-acetylthreonine, phenylacetylglutamine, tryptophan, N,N,N-trimethyl-L-alanyl-L-proline betaine (TMAP), creatinine, meso-erythritol, arabitol, myo-inositol, N-acetylserine, N-acetylalanine, 3-methylhistidine, trans-4-hydroxyproline, kynurenine, urea, 3-indoxylsulfate, and combinations thereof in a sample by mass spectrometry. Methods to extract the analytes from biological samples and to chromatographically separate the analytes prior to detection by mass spectrometry are also provided.

In an aspect of the invention wherein the method comprises detecting and determining the amount of compound A in a sample by mass spectrometry, the mass spectrum of compound A may comprise one or more peaks (i.e., mass to charge ratio (m/z)) selected from the group consisting of about 177, 159, 133, 131, 129, 115, 113, 111, 101, 100, 99, 89, 85, 83, 75, 73, 57.03, 57.00, 97, 87, 74, 84, and 67.

As use herein, the term "about" means the value±0.5.

In another embodiment, the present invention provides a method for calculating the estimated glomerular filtration rate (eGFR) in a subject comprising the steps of:

1) determining the level of a compound represented by formula I or formula II or a salt thereof, in a biological sample obtained from the subject, using chromatography, mass spectrometry, enzyme-linked immunosorbent assay (ELISA), antibody linkage, immunoblotting, immunohistochemistry (IHC), other immunochemical methods, or a combination thereof; and 2) calculating the eGFR using an algorithm that utilizes the determined level of the compound.

In other embodiments, the present invention provides methods for determining predisposition of a subject to developing reduced kidney function, classifying (or staging) a subject according to level (or stage) of kidney function, monitoring kidney function in a subject, diagnosing chronic kidney disease (CKD), monitoring the progression or regression of CKD in a subject, diagnosing acute kidney injury (AKI), monitoring the progression or regression of AKI, assessing kidney function of a subject in response to a composition, treating a subject having CKD, and treating a subject having AKI based on the level of a compound represented by formula I or formula II detected in a biological sample obtained from the subject.

The present invention also provides kits comprising a compound of formula I or formula II or a salt thereof.

In another embodiment, the kit of the present invention comprises a compound of formula I or formula II or a salt thereof and instructions for measuring the level of the compound of formula I or formula II or a salt thereof in a biological sample.

In another embodiment, the kit includes an internal standard comprising a labeled compound of formula I or formula II or a salt thereof and instructions for measuring the level of the compound of formula I or formula II or a salt thereof in a biological sample.

In yet another embodiment, the kit includes a compound of formula I or formula II or a salt thereof, a labeled compound of formula I or formula II or a salt thereof, and instructions for measuring the level of the compound of formula I or formula II in a biological sample.

In one embodiment, the kit of the present invention comprises a compound of formula I or formula II or a salt thereof and instructions for estimating GFR in a subject, determining predisposition of a subject to developing reduced kidney function, classifying (or staging) a subject according to level (or stage) of kidney function, monitoring kidney function in a subject, diagnosing chronic kidney disease (CKD), monitoring the progression or regression of CKD in a subject, diagnosing acute kidney injury (AKI), monitoring the progression or regression of AKI, assessing kidney function of a subject in response to a composition, treating a subject having CKD, and treating a subject having AKI based on the level of the compound detected in a biological sample obtained from the subject.

BRIEF DESCRIPTION OF THE DRAWINGS

FIGS. 17A, 17B, 17C and 17D show LC/MS mass spectra (A-B) and chromatogram (D) of hydrogenated compound A in a urine sample. Panel C shows the extracted ion chromatogram for native compound A (~2.5 min), which is absent after hydrogenation.

DETAILED DESCRIPTION OF THE INVENTION

Definitions

Figure 1:
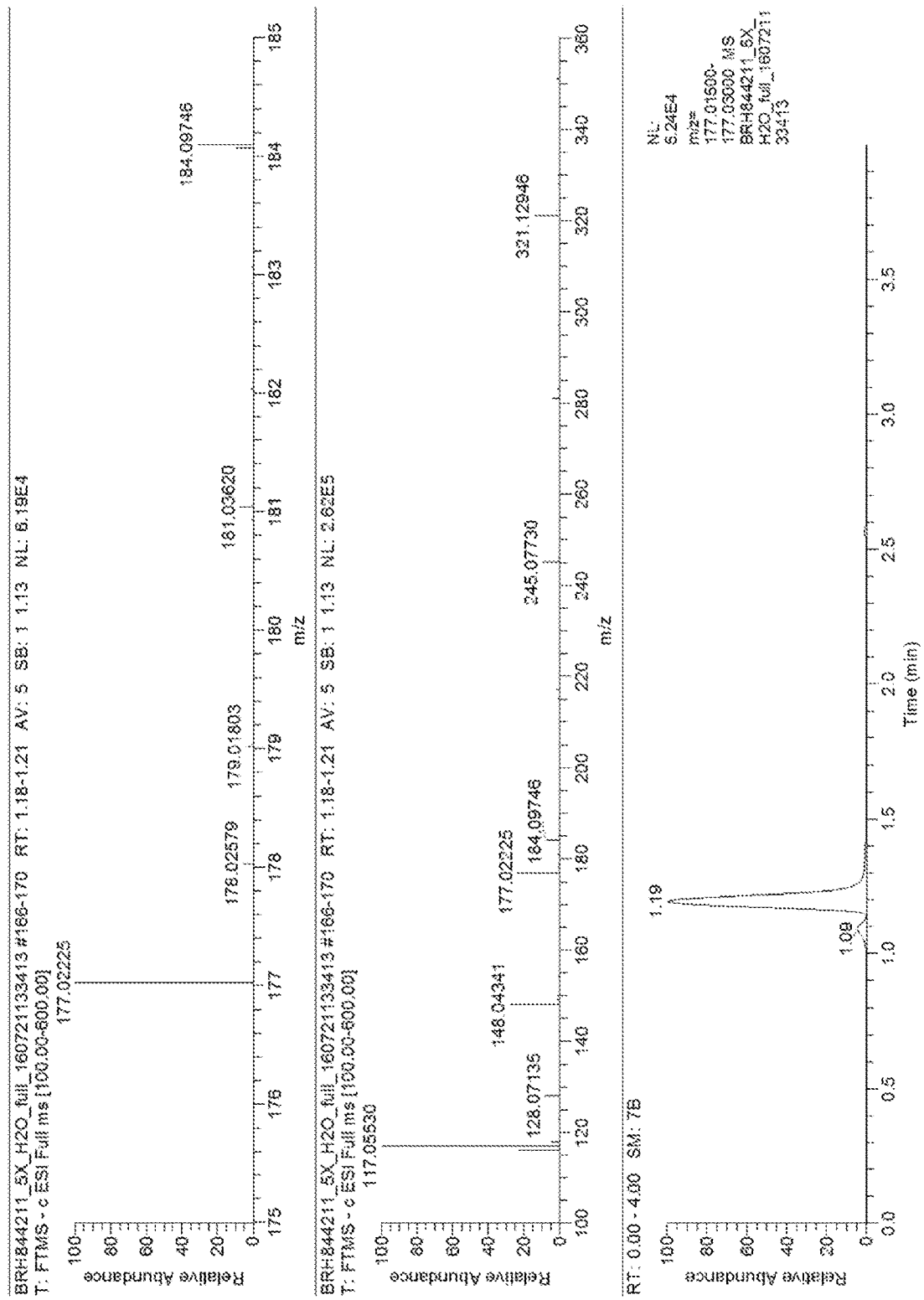
FIG. 1 shows LC/MS chromatogram and spectrum of compound A in a human plasma sample under basic chromatographic conditions.

Unless otherwise specified, the below terms used herein are defined as follows:

The compounds of the invention may be present in the form of salts. Any suitable organic or inorganic salts are included in the present invention. In certain embodiments, the salts of the compounds of the invention refer to non-toxic "pharmaceutically acceptable salts." The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Pharmaceutically acceptable salt forms include pharmaceutically acceptable acidic/anionic or basic/cationic salts. Examples of pharmaceutically acceptable salts include, but are not limited to, mineral or organic acid salts of basic residues such as amines; alkali or organic salts of acidic residues such as carboxylic acids; and the like.

For example, such salts include, the acetate, ascorbate, benzenesulfonate, benzoate, benzylate, bicarbonate, bitartrate, bromide, calcium edetate, camsylate, carbonate, chloride, citrate, dihydrochloride, edetate, edisylate, ethane disulfonate, estolate, esylate, fumarate, glyceptate, gluconate, glutamate, glycolate, glycollylarsanilate, hexylresorcinate, hydrabamine, hydrobromide, hydrochloride, hydroxymaleate, hydroxynaphthoate, iodide, isethionate, lactate, lactobionate, malate, maleate, mandelate, methanesulfonate, mesylate, methylbromide, methylnitrate, methylsulfate, mucate, napsylate, nitrate, oxalate, pamoate, pantothenate, phenylacetate, phosphate/diphosphate, polygalacturonate, propionate, salicylate, stearate, subacetate, succinate, sulfamide, sulfate, tannate, tartrate, teoclate, tosylate, triethiodide, ammonium, benzathine, chloroprocaine, colline, diethanolamine, ethylenediamine, meglumine and procaine salts. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of acids other than those mentioned above which, for example, are useful for purifying or isolating the compounds of the present invention (e.g. trifluoroacetate salts) also comprise a part of the invention.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 95%, 99% or 99.9% by weight pure relative to the other stereoisomers. When a single enantiomer is named or depicted by structure, the depicted or named enantiomer is at least 60%, 70%, 80%, 90%, 95%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of the compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

When compounds having one or more stereocenters are depicted with particular stereochemistry for at least one stereocenter, the present invention also includes compounds that have the opposite stereochemistry at the corresponding stereocenter(s) and compounds that have no specific stereochemistry at the corresponding stereocenter(s).

"Treating" a condition or disease refers to curing as well as ameliorating at least one symptom of the condition or disease.

As used herein, the term "subject" means any animal, but is preferably a mammal, such as, for example, a human, monkey, non-human primate, rat, mouse, cow, dog, cat, pig, horse, or rabbit. Even more preferably, the subject is a human.

As used herein, "effective amount" means the amount of active compound agent that elicits the desired biological response in a subject. Such response includes alleviation of the symptoms of the disease or disorder being treated. The effective amount of a compound of the invention in such a therapeutic method is from about 0.01 mg/kg/day to about 1000 mg/kg/day or from about 0.1 mg/kg/day to about 100 mg/kg/day.

The "level" of the compound of the present invention or one or more additional compounds means the absolute or relative amount or concentration of the compound measured in the sample.

"Sample" or "biological sample" means biological material isolated from a subject. The biological sample may contain any biological material suitable for detecting the desired compounds, and may comprise cellular and/or non-cellular material from the subject. The sample can be isolated from any suitable biological tissue or fluid such as, for example, kidney tissue, blood, blood plasma (plasma), blood serum (serum), urine, saliva, or cerebral spinal fluid (CSF). Preferably, the biological sample is blood, blood plasma, serum, saliva or urine. In another preferred embodiment, the biological sample is blood serum or blood plasma.

A "reference level" means a level of the compound of the present invention or additional compound(s) that is indicative of a particular disease state, phenotype, or lack thereof, as well as combinations of disease states, phenotypes, or lack thereof. A "reference level" may be an absolute or relative amount or concentration of the compound of the present invention or additional compound(s), a presence or absence of the compound of the present invention or additional compound(s), a range of amount or concentration of the compound of the present invention or additional compound(s), a minimum and/or maximum amount or concentration of the compound of the present invention or additional compound(s), a mean amount or concentration of the compound of the present invention or additional compound(s), and/or a median amount or concentration of the compound of the present invention or additional compound(s); and, in addition, "reference levels" of combinations of the compound of the present invention and additional compound(s) may also be ratios of absolute or relative amounts or concentrations of two or more compounds with respect to each other. Appropriate reference levels of the compound of the present invention or additional compound(s) for a particular disease state, phenotype, or lack thereof may be determined by measuring levels of the compound of the present invention or desired compounds in one or more appropriate subjects. A "positive" reference level means a level that is indicative of a particular disease state or phenotype. A "negative" reference level means a level that is indicative of a lack of a particular disease state or phenotype.

As used herein, a "reference sample" refers to a sample containing reference level of a compound. For example, a reference sample can be obtained from a subject that does not have a particular disease, disease state or phenotype, such as CKD or acute kidney injury.

"Glomerular filtration rate" or "GFR" is the volume of fluid filtered from the renal glomerular capillaries into the Bowman's capsule per unit time. The GFR is a metric of kidney function whereby GFR at or above a certain threshold indicates normal kidney function and GFR below the threshold value indicates kidney function is compromised or impaired. Generally, a high GFR value indicates better kidney function while a low GFR indicates kidney function impairment (e.g., chronic kidney disease, acute kidney injury).

"Measured glomerular filtration rate" or "mGFR" means the actual glomerular filtration rate which is determined using a filtration marker such as inulin, iothalamate or iohexol. mGFR is performed in a clinical setting and is the most accurate measurement of renal function.

"Estimated glomerular filtration rate" or "eGFR" means a calculated estimate of the actual glomerular filtration rate. The calculated value may be based on the level of one or more compounds or biomarkers and may include other variables such as demographic information (e.g., age or gender). One current method for calculating eGFR is based on serum creatinine concentration. Other current methods for calculating an eGFR use the amount of cystatin C alone or in combination with the amount of serum creatinine. Currently used equations for estimating GFR include "Chronic Kidney Disease Epidemiology Collaboration" (CKD-EPI) and "Modification of Diet in Renal Disease eGFR" (MDRD). Generally, low eGFR values are associated with decreased kidney function.

"Urine albumin" is a test measuring the amount of albumin in the urine and is also used to detect kidney disease.

"Serum creatinine" or "SCr" refers to the measurement of creatinine in serum and is commonly used to estimate GFR.

"Blood urea nitrogen" or "BUN" refers to the measurement of the amount of nitrogen in the blood in the form of urea. BUN is a test used to measure kidney function.

"Chronic Kidney Disease" or "CKD" includes conditions that damage kidneys resulting in decreased ability of the kidney to remove wastes from the body resulting in high levels of the wastes in the body and leading to increased risk of illness and development of complications such as high blood pressure, anemia, poor nutritional health and nerve damage. Patients with abnormalities in kidney function for at least three months may be diagnosed with CKD. Kidney damage due to CKD is permanent.

"Acute kidney injury" or "AKI" refers to a condition in which there is a rapid loss of kidney function. Kidney damage due to AKI may be reversible.

"Chronic Kidney Disease Stages" or "CKD Stages" means the degree of kidney damage as currently assessed using the measured or estimated glomerular filtration rate (mGFR, eGFR). Clinically, 5 stages of CKD are generally recognized with kidney function regarded as normal in Stage 1 (GFR>90), minimally reduced in Stage 2 (GFR 60-89), moderately reduced in Stages 3 A and 3B (GFR 30-59), severely reduced in Stage 4 (GFR 15-29) and very severe or endstage kidney failure, also referred to as established renal failure at Stage 5 (GFR<15, or on dialysis). Kidney function stages may be used to refer to kidney damage present for any amount of time (i.e., kidney damage due to AKI or CKD).

The present invention can be understood more fully by reference to the following detailed description and examples, which are intended to exemplify non-limiting embodiments of the invention.

Compounds and Compositions

The present invention provides novel compounds, compositions, methods of synthesis, detection methods, and their use in diagnostic methods and treatment methods.

In a 1$^{st}$ embodiment, the present invention provides a compound represented by the following formula:

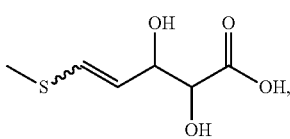

(I)

or a salt thereof.

In certain embodiments, the compound of formula (I) in the 1$^{st}$ embodiment is represented by the following formula:

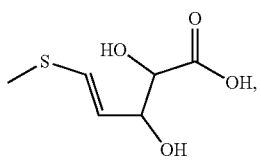

(II)

or a salt thereof.

In certain embodiments, the compound of formula (I) or formula (II) in the 1$^{st}$ embodiment is represented by the following formula:

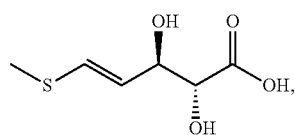

(III)

or a salt thereof.

In certain embodiments, the compound of formula (I) or formula (II) in the 1$^{st}$ embodiment is represented by the following formula:

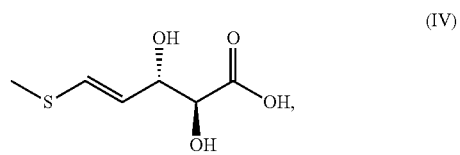

(IV)

or a salt thereof.

In one embodiment, the compound of formula (II), (III), or (IV), or a salt thereof is at least 60% optically pure, at least 70% optically pure, at least 80% optically pure, at least 90% optically pure, at least 95% optically pure, or at least 99% optically pure.

In various embodiments, the compound of the present invention described herein (e.g., compounds represented by formula (I), (II), (III), or (IV), or a salt thereof) is substantially free of impurities.

In various embodiments, the compound of the present invention described herein (e.g., compounds represented by formula (I), (II), (III), or (IV), or a salt thereof) is at least 60% pure, at least 70% pure, at least 80% pure, at least 90% pure, at least 95% pure or at least 99% pure.

In certain embodiments, the compound of the present invention described herein (e.g., compounds represented by formula (I), (II), (III), or (IV), or a salt thereof) is isotopically labeled. In one embodiment, the compound of formula (I), (II), (III), or (IV), or a salt thereof is radiolabeled, such as with tritium ($^3$H) or carbon 14 ($^{14}$C). In another embodiment, the compound of formula (I), (II), (III), or (IV) or a salt thereof is labeled with deuterium, carbon 13 ($^{13}$C), oxygen 17 ($^{17}$O), oxygen 18 ($^{18}$O), sulfur 33 ($^{33}$S), sulfur 34 ($^{34}$S), or any other known sulfur isotopes, or a combination thereof. Any suitable methods for isotopic labeling of the compounds of the present invention can be used.

In certain embodiments, the isotopically labeled compound of the present invention is represented by the following formula:

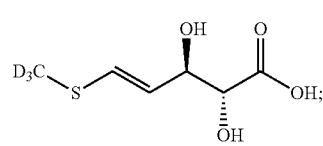

(L1)

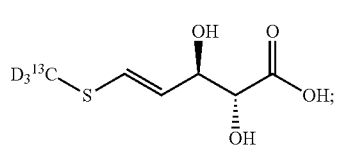

(L2)

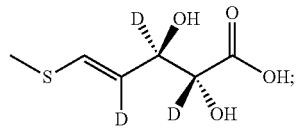

(L3)

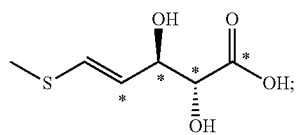

(L4)

-continued

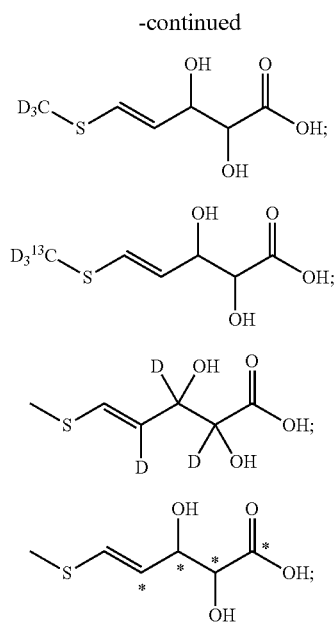

or a pharmaceutically acceptable salt thereof, wherein *indicates $^{13}C$.

The compounds described above, such as compounds of formula (I), (II), (III), (IV), (L), (L2), (L3), (L4), (L5), (L6), (L7) or (L8) or a salt (e.g., a pharmaceutically acceptable salt) thereof, can be used in any of the methods described herein. For example, the compounds of the present invention can be used to assess kidney function in a subject, to calculate an estimate of the glomerular filtration rate in a subject, to monitor a subject to detect changes in kidney function (e.g., decreases in function which may indicate acute kidney injury or incipient CKD), to classify subjects according to the degree of kidney function (e.g., normal, mildly reduced, moderately reduced, severely reduced, end-stage kidney failure) and to distinguish subjects having CKD vs. control subjects not diagnosed with CKD. Further, the compounds may be used to monitor changes in kidney function over time or in response to drug treatment, disease (e.g., type II diabetes), or lifestyle interventions (e.g., diet, exercise) and to identify or rule-out subjects as suitable candidates for drug therapies and/or kidney transplant.

Also included in the present invention are antibodies or antibody fragments that specifically bind to the compound described herein (e.g. compound of formula (I), (II), (III), or (IV) or a salt (e.g., a pharmaceutically acceptable salt) thereof). Methods for generating antibodies that specifically binds to small molecules are known in the art. Antibody derivatives, such as a polypeptide comprising the $V_H$ and $V_L$ sequences of the antibody described above are also included. In certain embodiments, the polypeptide is a fusion protein. The present invention also includes cells for producing the antibodies or antibody fragments and the antibody derivatives described herein. In one embodiment, the cell is a eukaryotic cell.

Methods

In a $2^{nd}$ embodiment, the present invention provides a method for determining the level of the compound of the present invention (e.g., compound of formula (I), (II), (III), or (IV), or a salt thereof), in a subject comprising: (1) preparing an analytical sample from a biological sample obtained from the subject; and (2) determining the level of the compound.

The biological sample is analyzed in order to determine the level of the compound of the present invention (e.g., compound of formula (I), (II), (III), or (IV), or a salt thereof) in the sample. Methods of analyzing the sample include chromatography (e.g., HPLC, gas chromatography, liquid chromatography), mass spectrometry (e.g., MS, MS-MS), enzyme-linked immunosorbent assay (ELISA), antibody linkage, immunoblotting, immunohistochemistry (IHC), other immunochemical techniques, and combinations thereof.

In an exemplary method, determining the level of the compound of formula (I):

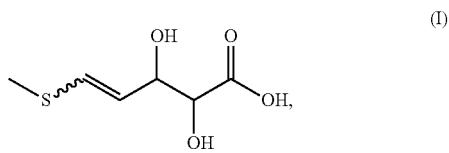

or a salt thereof, in a biological sample obtained from the subject, comprises determining the level of the compound of formula (I) using mass spectrometry.

In one example, the biological sample may be subjected to liquid chromatography (LC) prior to mass spectrometry. LC methods may include, for example, high performance LC (HPLC) or ultra high performance LC (UHPLC or UPLC). In some examples, HPLC or UPLC may be conducted using a reversed phase column chromatographic system, hydrophilic interaction chromatography (HILIC), ion exchange chromatography, or a mixed phase column chromatographic system.

Mass spectrometry is performed using a mass spectrometer that includes an ion source for ionizing the fractionated sample and creating charged molecules for further analysis. Ionization of the sample may be performed by, for example, heated electrospray ionization (HESI-II). The sample may be ionized in positive or negative mode.

After a sample has been ionized, the positively or negatively charged ions may be analyzed to determine a mass-to-charge ratio. Exemplary suitable analyzers for determining mass-to-charge ratios include quadrupole analyzers, ion trap analyzers, Fourier Transform Mass Spectrometry (FTMS) analyzers, and time of flight analyzers.

In some embodiments, the method for determining the level of compound A in a sample by mass spectrometry comprises detecting one or more ions selected from the group consisting of ions with a mass to charge ratio (m/z) of about 177, 159, 133, 131, 129, 115, 113, 111, 101, 100, 99, 89, 85, 83, 75, 73, 57.03, 57.00, 56, 97, 87, 74, 84, and 67.

Analysis results may include data produced by tandem MS. In some examples, tandem MS may be accurate-mass tandem MS. For example, the accurate-mass tandem mass spectrometry may use a quadrupole time-of-flight (Q-TOF) analyzer. In other examples, tandem MS may be FTMS. Tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion.

In some embodiments, the level of the compound of the present invention (e.g., compound of formula (I), (II), (III), or (IV) or a salt (e.g., a pharmaceutically acceptable salt) thereof, can be used, for example, to assess kidney function in a subject, to calculate an estimate of the glomerular filtration rate in a subject, to monitor a subject to detect changes in kidney function (e.g., decreases in function which may indicate acute kidney injury or incipient CKD), to classify subjects according to the degree of kidney function (e.g., normal, mildly reduced, moderately reduced, severely reduced, end-stage kidney failure) and to distinguish subjects having CKD vs. control subjects not diagnosed with CKD. Further, the compounds may be used to monitor changes in kidney function over time or in response to drug treatment, disease (e.g., type II diabetes), or lifestyle interventions (e.g., diet, exercise) and to identify or rule-out subjects as suitable candidates for drug therapies and/or kidney transplant.

In an exemplary method, assessing kidney function in a subject comprises determining the level of the compound of formula (I):

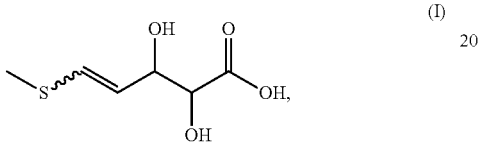

(I)

or a salt thereof, in a biological sample obtained from the subject, wherein an elevated level of the compound in the biological sample as compared to a reference level is indicative of reduced kidney function in the subject.

In a 3$^{rd}$ embodiment, the present invention provides a method for calculating the estimated glomerular filtration rate (eGFR) in a patient comprising the steps of: (1) determining the level of the compound of formula (I) or a salt thereof, in a biological sample obtained from the subject; and (2) calculating the eGFR using an algorithm that utilizes the measured level of the compound, wherein the algorithm is developed using GFR measured using an exogenous filtration marker. Any suitable methods can be used for determining the level of the compound. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

In certain embodiments, the eGFR is calculated using one or more additional compounds relevant for the assessment of kidney function. In one embodiment, the one or more additional compounds are selected from pseudouridine, N-acetylthreonine, 2-C-mannopyranosyl tryptophan, N-acetylserine, N-acetyl alanine, N6-carbamoylthreonyl adenosine, 4-acetamidobutanoate, erythritol, myo-inositol, erythronate, urea, arabitol, N2,N2-dimethylguano sine, N1-methyladeno sine, 3-methylglutarylcarnitine, S-adenosylhomocysteine, N-acetylmethionine, N6-acetyllysine, kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate, p-cresol sulfate, and N,N,N-trimethyl-L-alanyl-L-proline betaine (TMAP). In another embodiment, the eGFR algorithm further utilizes serum cystatin C levels. In yet another embodiment, the eGFR algorithm further utilizes one or more demographic parameters selected from the group consisting of age, sex and race.

In a 4$^{th}$ embodiment, for methods described in the 2$^{nd}$ and 3$^{rd}$ embodiments, the compound of formula (I) is represented by formula (II):

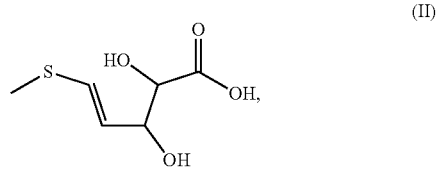

(II)

or a salt thereof.

In a 5$^{th}$ embodiment, for methods described in the 2$^{nd}$ and 3$^{rd}$ embodiments, the compound of formula (I) or formula (II) is represented by formula (III):

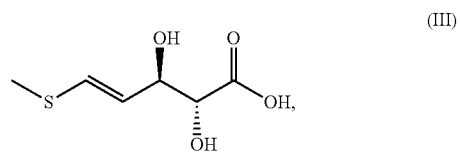

(III)

or a salt thereof.

In a 6$^{th}$ embodiment, for methods described in the 2$^{nd}$ and 3$^{rd}$ embodiments, the compound of formula (I) or formula (II) is represented by formula (IV):

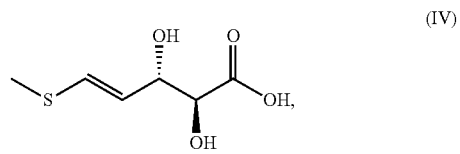

(IV)

or a salt thereof.

In a 7$^{th}$ embodiment, for methods described in the 2$^{nd}$-6$^{th}$ embodiments, the level of the compound is determined by tandem liquid chromatography-mass spectrometry (LC-MS/MS).

In an 8$^{th}$ embodiment, the methods described in the 2$^{nd}$-7$^{th}$ embodiments further comprise using the determined level of the compound in a mathematical model to assess kidney function.

In a 9$^{th}$ embodiment, the methods described in the 2$^{nd}$-8$^{th}$ embodiments further comprise analyzing the biological sample to determine the level of one or more additional compounds relevant for the assessment of kidney function. The one or more compounds may be selected from the group consisting of the following compounds: pseudouridine, N-acetylthreonine, 2-C-mannopyranosyl tryptophan, N-acetylserine, N-acetylalanine, N6-carbamoylthreonyladenosine, 4-acetamidobutanoate, erythritol, myo-inositol, erythronate, urea, arabitol, N2,N2-dimethylguano sine, N1-methyladeno sine, 3-methyl glutarylcarnitine, S-adenosylhomocysteine, N-acetylmethionine, N6-acetyllysine, kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate, and p-cresol sulfate, and N,N,N-trimethyl-L-alanyl-L-proline betaine (TMAP), and combinations thereof. In one embodiment, the additional compounds are selected from the group consisting of pseudouridine, N-acetylthreonine, tryptophan, phenylacetylglutamine, 2-C-mannopyranosyl tryptophan, kynurenine, myo-inositol, N,N,N-trimethyl-L-alanyl-L-proline betaine (TMAP), and creatinine. In another embodiment, the additional compounds are selected from the group consisting of pseudouridine, N-acetylthreonine, tryptophan, phenylacetylglutamine, and creatinine.

In certain embodiments, the levels of two, three, four, five, six, seven, eight, nine, ten, eleven, twelve or more additional compounds are determined in the method described in the $9^{th}$ embodiment.

In certain embodiments, the method described in the $9^{th}$ embodiment further comprises analyzing the biological sample to determine the level of pseudouridine, N-acetylthreonine, tryptophan, and phenylacetylglutamine.

In certain embodiments, the method described in the $9^{th}$ embodiment further comprises analyzing the biological sample to determine the level of pseudouridine, N-acetylthreonine, tryptophan, phenylacetylglutamine, and creatinine.

Determining levels of the compound of the present invention and one or more additional compounds may allow greater sensitivity and specificity in the described methods. For example, pair-wise analysis of two compounds or ratios of the levels of certain compounds in biological samples may allow greater sensitivity and specificity in assessing kidney function and aiding in the assessment of kidney function.

The level(s) of the compound of formula (I), (II), (III), or (IV), and/or the one or more additional compounds may be compared to kidney function reference levels using various techniques, including a simple comparison (e.g., a manual comparison). The level(s) of the compound of formula (I), (II), (III), or (IV), and/or the one or more additional compounds in the biological sample may also be compared to reference levels using one or more statistical analyses (e.g., t-test, Welch's T-test, Wilcoxon's rank sum test, correlation analysis, Random Forest, T-score, Z-score) or using a mathematical model (e.g., algorithm, statistical model). For example, a mathematical model comprising a single algorithm or multiple algorithms may be used to assess kidney function in a subject.

The results of the method may be used along with other methods and measurements (or the results thereof) useful in the assessment of kidney function in a subject. For example, clinical parameters such as BUN, SCr, and/or urine albumin measurements; markers of kidney function such as β-2 microglobulin, β-TRACE, 2-C-mannopyranosyl tryptophan; as well as patient information such as, for example, family history of CKD or other risk factors can be used with the compounds.

In certain embodiments, the level of the compound of the present invention and/or one or more additional compounds can be used in a mathematical or statistical model or formula to provide a physician with a numerical score ("Kidney Function Score") indicating the level of kidney function and/or the probability that a subject has compromised kidney function which may indicate AKI or CKD. The score is based upon clinically significantly changed reference level(s) for a compound and/or combination of compounds. The reference level can be derived from an algorithm or computed from indices for impaired GFR. Methods for determining a subject's Kidney Function Score may comprise comparing the level(s) of the one or more kidney function compounds in the sample to kidney function reference levels of the one or more compounds in order to determine the subject's Kidney Function Score. The method may employ any number of compounds selected from the following list: pseudouridine, N-acetylthreonine, 2-C-mannopyranosyl tryptophan, N-acetylserine, N-acetylalanine, N6-carbamoylthreonyladenosine, 4-acetamidobutanoate, erythritol, myo-inositol, erythronate, urea, arabitol, N2,N2-dimethylguanosine, N1-methyladenosine, 3-methyl glutarylcarnitine, S-adenosylhomocysteine, N-acetylmethionine, N6-acetyllysine, kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate, p-cresol sulfate, and N,N, N-trimethyl-L-alanyl-L-proline betaine (TMAP). Multiple compounds may be correlated with kidney function, by any method, including statistical methods such as regression analysis.

The Kidney Function Score can be used to place the subject in the range of kidney function from normal (i.e. no kidney function impairment) to mildly reduced, moderately reduced, severely reduced, or end-stage kidney failure. Non-limiting example uses of the Kidney Function Score include: assessment of kidney function; estimation of GFR; classification of kidney function; susceptibility to developing CKD; susceptibility to developing AKI; diagnosis and stage of CKD; monitoring CKD progression by periodic determination and monitoring of the Kidney Function Score; monitoring the kidney function status of kidney transplant recipients; determining a response to therapeutic intervention; evaluating drug efficacy; and determining tolerance of therapeutic and/or contrast imaging agents.

In certain embodiments, for the methods of the present invention described herein, the biological sample is blood, blood plasma, serum, saliva or urine. In one embodiment, the biological sample is blood plasma. In another embodiment, the biological sample is serum.

In certain embodiments, for the methods of the present invention described herein, the biological sample is obtained from the subject prior to treatment with an agent that allows direct measurement of glomerular filtration rate.

In certain embodiments, for the methods of the present invention described herein, the subject is a human.

In certain embodiments, for the methods of the present invention described herein, the subject has no symptoms of impaired kidney function or has no known risk factors for impaired kidney function. In other embodiments, the subject exhibits risk factors for developing chronic kidney disease (e.g., age over 60, hypertension, diabetes, cardiovascular disease, family history of CKD). In certain embodiments, the subject has been previously diagnosed with hypertension or diabetes. In certain embodiments, the subject a family history of chronic kidney disease. In certain embodiments, the subject has symptoms of impaired kidney function. In certain embodiments, the subject is one for whom kidney function assessment using conventional methods is difficult.

In certain embodiments, the subject is selected from the group consisting of the following: obese, very lean, vegetarian, chronically ill, and elderly.

In certain embodiments, the subject is a candidate to be a kidney donor.

In certain embodiments, the subject has been treated with or is being considered for treatment with an agent that may have a toxic effect on the kidneys. In one embodiment, the agent is contrast imaging agent. In another embodiment, the agent is a therapeutic agent for treating a disease or condition, such as a chemotherapeutic agent. In yet another embodiment, the agent is an antibiotic.

In certain embodiments, the methods could be used to monitor kidney function in subjects having CKD or subjects suspected of being predisposed to developing CKD (e.g., at risk subjects due to family history of CKD, drug therapy, chronic illness, etc.). In one example, the compound of the present invention may be used to monitor kidney function in subjects not having CKD. For example, in a subject suspected of being predisposed to developing CKD, the compounds described herein may be used to monitor the development of CKD.

Kits

The present invention includes kits for measuring the level of the compound of formula (I), (II), (III), or (IV), or a salt thereof, in a biological sample.

In certain embodiments, the kit of the present invention comprises a compound of formula (I), (II), (III), or (IV), or a salt thereof.

In certain embodiments, the kit of the present invention comprises a compound of formula (I), (II), (III), or (IV), or a salt thereof and instructions for measuring the level of the compound of formula (I), (II), (III), or (IV), in a biological sample.

In certain embodiments, the kit of the present invention can comprise a labeled compound (e.g., an internal standard) or an agent capable of detecting the compound of formula (I), (II), (III), or (IV), or a salt thereof, in a biological sample.

In certain embodiments, the kit of the present invention can comprise a labeled compound (e.g., an internal standard) or an agent capable of detecting the compound of formula (I), (II), (III), or (IV), or a salt thereof, in a biological sample and instructions for measuring the level of the compound of formula (I), (II), (III), or (IV), or a salt thereof, in a biological sample.

In one embodiment, the internal standard in the kit described above is a labeled compound of formula (I), (II), (III), or (IV), or a salt thereof (e.g., a compound of formula (L), (L2), (L3), (L4), (L5), (L6), (L7) or (L8) or a salt thereof).

In one embodiment, the kit of the present invention comprises an unlabeled compound of formula (I), (II), (III), or (IV), or a salt thereof, a labeled compound of formula (I), (II), (III), or (IV), or a salt thereof (e.g., a compound of formula (L), (L2), (L3), (L4), (L5), (L6), (L7) or (L8) or a salt thereof), as an internal standard and instructions for measuring the level of the compound of formula (I), (II), (III), or (IV), or a salt thereof, in a biological sample.

In certain embodiments, the kit of the present invention can comprise a labeled compound (e.g., an internal standard, such as a compound of formula (L1), (L2), (L3), (L4), (L5), (L6), (L7) or (L8) or a salt thereof). In other embodiments, the kit may comprise an agent capable of detecting the compound of formula (I), (II), (III), or (IV), or a salt thereof, in a biological sample and means for determining the amount of the compound in the sample (e.g., an antibody against the compound of formula (I), (II), (III), or (IV), or a salt thereof).

In certain embodiments, the amount of the compound of formula (I), (II), (III), or (IV), or a salt thereof, in a biological sample can be determined by chromatography, mass spectrometry, enzyme-linked immunosorbent assay (ELISA), antibody linkage, immunoblotting, immunohistochemistry (IHC), other immunochemical methods, or a combination thereof using the kit of the present invention described herein. In certain embodiments, the amount of the compound of formula (I), (II), (III), or (IV), or a salt thereof, in a biological sample can be determined by chromatography, mass spectrometry, or a combination thereof. In certain embodiments, the amount of the compound of formula (I), (II), (III), or (IV), or a salt thereof, in a biological sample can be determined by LC-MS using the kit of the present invention.

The kit may also comprise, e.g., a buffering agent, a preservative, or a stabilizing agent. The kit may also contain a control sample or a series of control samples which can be assayed and compared to the test sample. Each component of the kit is usually enclosed within an individual container and all of the various containers are within a single package along with instructions for determining whether the tested subject is suffering from or is at risk of developing a disorder associated with the relevant compound.

In some embodiments, the kit of the present invention may include instructions for assessing or monitoring kidney function in a subject, determining predisposition to developing reduced kidney function, classifying a subject according to level of kidney function, diagnosing or monitoring CKD, diagnosing or monitoring AKI, or estimating GFR in a subject based on the level of the compound detected in a biological sample obtained from the subject.

In certain embodiments for the kit of the present invention, the compound of formula (I), (II), (III), or (IV) is isotopically labeled. In one embodiment, the compound of formula (I), (II), (III), or (IV), is radiolabeled, for example, with tritium ($^3H$) or carbon 14 ($^{14}C$). In another embodiment, the compound of formula (I), (II), (III), or (IV) is deuterated, labeled with carbon 13 ($^{13}C$), oxygen 17 ($^{17}O$), oxygen 18 ($^{18}O$), sulfur 33 ($^{33}S$), sulfur 34 ($^{34}S$), or any other known sulfur isotopes, or a combination thereof. In another embodiment, the labeled compound of formula (I), (II), (III), or (IV) is represented by formula (L1), (L2), (L3), (L4), (L5), (L6), (L7) or (L8) described above. In an example, the labeled compound of formula (I), (II), (III), or (IV) (e.g., compound of formula (L1), (L2), (L3), (L4), (L5), (L6), (L7) or (L8) or a salt thereof), can be used as an internal standard.

The present invention also provides kits comprising antibodies or antibody fragments that specifically bind to the compound of formula (I), (II), (III), or (IV), or a salt (e.g., a pharmaceutically acceptable salt) thereof described above. In certain embodiments, the kits of the present invention comprise antibody derivatives, such as a polypeptide comprising the $V_H$ and $V_L$ sequences of the antibody described above. In one embodiment, the polypeptide is a fusion protein.

In some embodiments, the kit of the present invention comprises antibodies or antibody fragments that specifically bind to the compound of formula (I), (II), (III), or (IV), or a salt (e.g., a pharmaceutically acceptable salt) thereof and instructions for measuring the level of the compound of formula (I), (II), (III), or (IV), or a salt thereof, in a biological sample.

In some embodiments, the kit of the present invention comprises an antibody, an antibody fragment or an antibody derivative described above, and instructions for assessing or monitoring kidney function, estimating GFR, determining predisposition to developing reduced kidney function, classifying a subject according to level of kidney function, diagnosing or monitoring chronic kidney disease (CKD), or diagnosing or monitoring acute kidney injury (AKI) in a subject based on the level of the compound detected in a biological sample obtained from the subject.

In certain embodiments, the kit described above comprises one or more additional biomarkers, wherein the one or more additional biomarkers are relevant to the assessment of kidney function. Any compounds described herein can be used in the kits of the present invention.

In various embodiments, the one or more additional compounds are selected from the group consisting of pseudouridine, N-acetylthreonine, 2-C-mannopyranosyl tryptophan, N-acetylserine, N-acetylalanine, N6-carbamoyl-threonyl adenosine, 4-acetamidobutanoate, erythritol, myo-inositol, erythronate, urea, arabitol, N2,N2-dimethylguanosine, N1-methyladenosine, 3-methylglutarylcarnitine, S-adenosylhomocysteine, N-acetylmethionine, N6-acetyllysine, kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate, p-cresol sulfate, and N,N,N-trimethyl-L-alanyl-L-proline betaine (TMAP), and combinations thereof. In one embodiment, the additional compounds are selected from the group consisting of pseudouridine, N-acetylthreonine, tryptophan, phenylacetylglutamine, 2-C-mannopyranosyl tryptophan, kynurenine, myo-inositol, N,N,N-trimethyl-L-alanyl-L-proline betaine (TMAP), and creatinine. In another embodiment, the additional compounds are selected from the group consisting of pseudouridine, N-acetylthreonine, tryptophan, phenylacetylglutamine, and creatinine.

In certain embodiments, the kits of the present invention comprise a compound of the present invention described above (compound of formula (I), (II), (III), or (IV), or a salt thereof), pseudouridine, N-acetylthreonine, tryptophan, and phenylacetylglutamine.

In certain embodiments, the kits of the present invention comprise a compound of the present invention described above (compound of formula (I), (II), (III), or (IV), or a salt thereof), pseudouridine, N-acetylthreonine, tryptophan, phenylacetylglutamine, and creatinine.

Methods of Preparation

One can refer to the following references for suitable methods of synthesis as described in March, *Advanced Organic Chemistry*, 3rd edition, John Wiley & Sons, 1985 or Wuts *Greene's Protective Groups in Organic Synthesis*, 5th edition, John Wiley & Sons 2014 and as in Richard Larock, *Comprehensive Organic transformations*, 4th edition, VCH publishers Inc, 1989.

In a first embodiment, the compound of formula (I) or formula (II) can be prepared by a method comprising the steps of:

a) reacting a compound of formula (V):

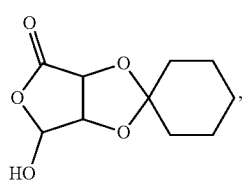

(V)

or a salt thereof, with a Wittig reagent such as R'$_3$P=CHSMe (also can be represented by its resonance structure R'$_3$P$^+$C$^-$HSMe), wherein R' is Ph or an electron-withdrawing group to form a compound of formula (Va):

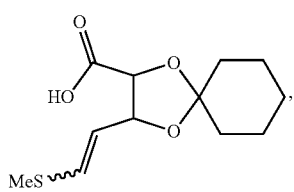

(Va)

or a salt thereof; and b) deprotecting the compound of formula (Va) or a salt thereof to form a compound of formula (I) or a salt thereof.

In certain embodiments, the method of the first embodiment further comprises purifying the compound of formula (Va) to yield a compound of formula (Vb):

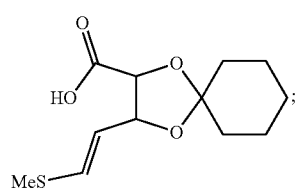

(Vb)

followed by deprotecting the compound of formula (Vb) to form the compound of formula (II) or a salt thereof.

In certain embodiments, the method of the first embodiment further comprises purifying the compound of formula (I) or a salt thereof to separate the trans-isomer and the cis-isomer to yield the compound of formula (II) or a salt thereof.

In a second embodiment, the present invention provides a method of preparing a compound of formula (III), comprising the steps of:

a) reacting a compound of formula (VI):

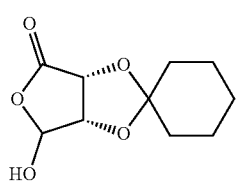

(VI)

or a salt thereof, with a Wittig reagent R'$_3$P=CHSMe, wherein R' is Ph or an electon-withdrawing group, to form a compound of formula (VIa):

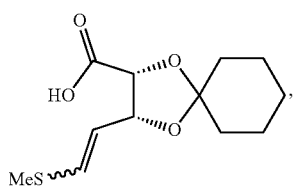

(VIa)

or a salt thereof;

b) purifying the compound of (VIa) or a salt thereof to yield a compound of formula (VIb):

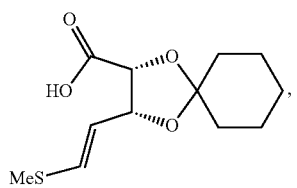

(VIb)

or a salt thereof; and c) deprotecting the compound of formula (VIb) or a salt thereof to form the compound of formula (III) or a salt thereof.

Alternatively, in a third embodiment, the compound of formula (III) or a salt thereof can be prepared by a method comprising the steps of:

a) reacting a compound of formula (VI):

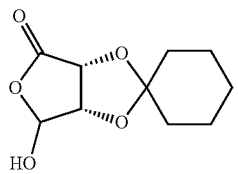
(VI)

or a salt thereof, with a Wittig reagent R'₃P=CHSMe, wherein R' is Ph or an electon-withdrawing group, to form a compound of formula (VIa):

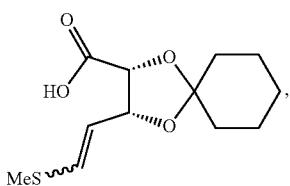
(VIa)

or a salt thereof;

b) deprotecting the compound of formula (VIa) or a salt thereof to form a compound of formula (VIc):

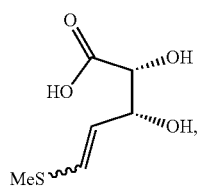
(VIc)

or a salt thereof; and c) purifying the compound of formula (VIc) or a salt thereof to yield the compound of formula (III) or a salt thereof.

In certain embodiments, the deprotection reaction in the methods of the first, second or third embodiment can be carried in the presence of an acid. Any suitable acid can be used. Exemplary acids include, but are not limited to, hydrochloric acid, acetic acid, trifluoroacetic acid, pyridinium p-toluensulfonate, p-toluenesulfonic acid (p-TsOH), formic acid, or strong or weak cation exchange resins in the hydrogen form. In certain embodiments, the acid is Dowex® 50WX8 resins.

In certain embodiments, the compound of formula (IV) or a salt thereof can be prepared according to a method as described in the second or third embodiment, wherein the compound of formula (VI) is replaced with the compound of formula (VI'):

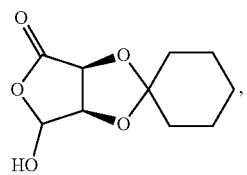
(VI')

In certain embodiments, isotopically labeled compound of formula (I), (II), (III) or (IV) can be prepared using isotopically labeled starting materials and/or reagent. In one embodiment, isotopically labeled Wittig reagent can be used in the methods described in the first, second or third embodiments to prepare isotopically labeled compounds of formula (I), (II), (III) or (IV). In one embodiment, the isotopically labeled Wittig reagent is Ph₃P=CH₂SCD₃ (also can be represented by its resonance structure Ph₃P⁺C⁻HSCD₃). In another embodiment, the isotopically labeled Wittig reagent is Ph₃P=CH₂S¹³CD₃ (also can be represented by its resonance structure Ph₃P⁺C⁻HS¹³CD₃).

In yet another embodiment the isotopically labeled 2,3-cyclohexylidene-erythruronic acid can be used to prepare isotopically labeled compound of formula (I), (II), (III) or (IV). In one embodiment, the isotopically labeled 2,3-cyclohexylidene-erythruronic acid is represented by the following formula:

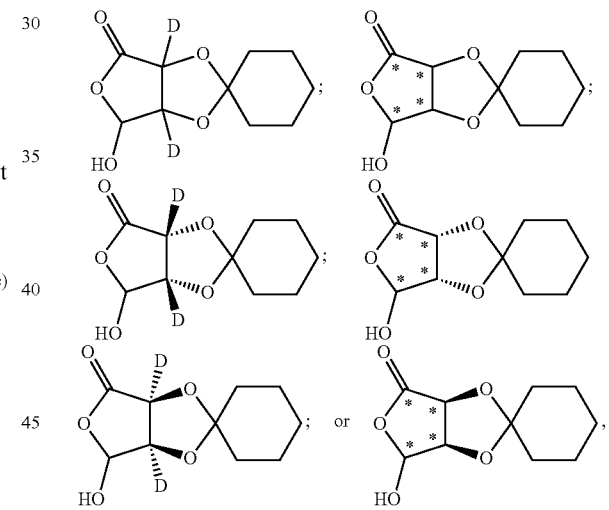

wherein * indicates ¹³C.

In a fourth embodiment, the compound of formula (III) can be prepared by a method comprising the steps of:

a) reacting a compound of formula (VII):

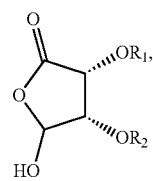
(VII)

or a salt thereof, with a Wittig reagent such as R'₃P=CHSMe, to form a compound of formula (VIIa) or a salt thereof,

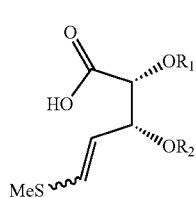

(VIIa)

wherein R' is Ph or an electon-withdrawing group, and $R_1$ and $R_2$ are each independently a silyl group;

b) purifying the compound of formula (VIIa) or a salt thereof to yield a compound of formula (VIIb) or a salt thereof:

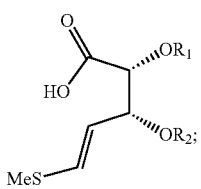

(VIIb)

and c) deprotecting the compound of formula (VIIb) or a salt thereof to form the compound of formula (III).

Alternatively, in a fifth embodiment, the compound of formula (III) can be prepared by a method comprising the steps of:

a) reacting a compound of formula (VII):

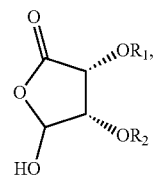

(VII)

or a salt thereof, with a Wittig reagent such as $R'_3P=CHSMe$, to form a compound of formula (VIIa) or a salt thereof,

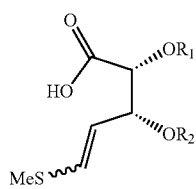

(VIIa)

wherein R' is Ph or an electon-withdrawing group, and $R_1$ and $R_2$ are each independently a silyl group;

b) deprotecting the compound of formula (VIIa) or a salt thereof to form a compound of formula (VIIc) or a salt thereof:

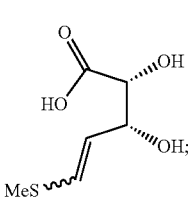

(VIIc)

and c) purifying the compound of formula (VIIc) or a salt thereof to yield the compound of formula (III) or a salt thereof.

In certain embodiments, the compound of formula (IV) or a salt thereof can be prepared according to a method as described in the fourth or fifth embodiment, wherein the compound of formula (VII) is replaced with the compound of formula (VII'):

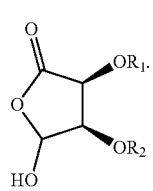

(VII')

In certain embodiments, the compound of formula (I) or (II) can be prepared by a method as described in the fourth or fifth embodiment, wherein the compound of formula (VII) is replaced with the compound formula (VII"):

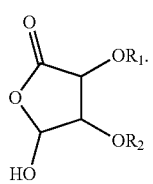

(VII")

In a sixth embodiment, the compound of formula (III) or a salt thereof can be prepared by a method comprising the steps of:

a) reacting a compound of formula (VIII):

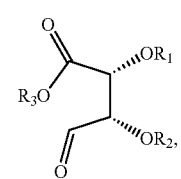

(VIII)

or a salt thereof, with a Wittig reagent $R'_3PCH_2SMe$, to form a compound of formula (VIIIa) or a salt thereof,

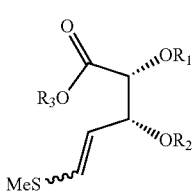

(VIIIa)

wherein R' is Ph or an electon-withdrawing group; $R_1$ and $R_2$ are silyl groups and $R_3$ is a t-butyl group or $R_3$ is a silyl group;

b) purifying the compound of formula (VIIIa) or a salt thereof to yield a compound of formula (VIIb) or a salt thereof:

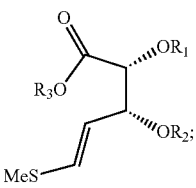

(VIIIb)

and c) deprotecting the compound of formula (VIIIb) or a salt thereof to form a compound of formula (III) or a salt thereof.

Alternatively, in a seventh embodiment, the compound of formula (III) or a salt thereof can be prepared by a method comprising the steps of:

a) reacting a compound of formula (VIII):

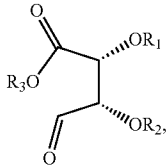

(VIII)

or a salt thereof, with a Wittig reagent $R'_3P=CHSMe$, to form a compound of formula (VIIIa) or a salt thereof,

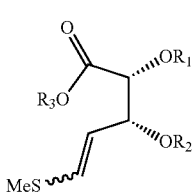

(VIIIa)

wherein R' is Ph or an electon-withdrawing group; $R_1$ and $R_2$ are silyl groups and $R_3$ is a t-butyl group or $R_3$ is a silyl group;

b) deprotecting the compound of formula (VIIIa) or a salt thereof to form a compound of formula (VIIIc) or a salt thereof:

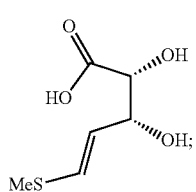

(VIIIc)

and c) purifying the compound of formula (VIIIc) or a salt thereof to yield the compound of formula (III) or a salt thereof.

In certain embodiments, the compound of formula (IV) or a salt thereof can be prepared according to a method as described in the sixth or seventh embodiment, wherein the compound of formula (VIII) is replaced with the compound of formula (VIII'):

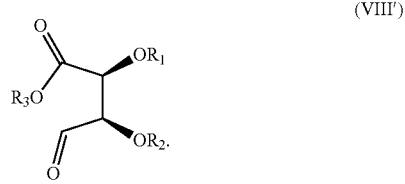

(VIII')

In certain embodiments, the compound of formula (I) or (II) can be prepared by a method as described in the fourth or fifth embodiment, wherein the compound of formula (VIII) is replaced with the compound formula (VIII"):

(VIII")

In certain embodiments, the Wittig reagent in the methods described above (e.g., in the first, second, third, fourth, fifth, sixth or seventh embodiment) is methylthiomethyl triphenyl phosphonium ylide ($Ph_3P=CHSMe$ (also can be represented by its resonance structure $Ph_3P^+C^-HSMe$)).

In certain embodiments, the Wittig reaction in the methods described above (e.g., in the first, second, third, fourth, fifth, sixth or seventh embodiment) is carried out in the presence of a base. Any suitable base can used. Exemplary bases include, but are not limited to, sodium bis(trimethylsilyl)amide, potassium bis(trimethylsilyl)amide, and n-butyllithium.

In one embodiment, the Wittig reaction in the methods described above (e.g., in the first, second, third, fourth, fifth, sixth or seventh embodiment) is carried out in the presence of sodium bis(trimethylsilyl)amide.

In certain embodiments, the Wittig reaction for the methods described above (e.g., in the first, second, third, fourth, fifth, sixth or seventh embodiment) is carried out in an organic solvent. Any suitable organic solvents or a mixture of organic solvents can be used, which may include, but are not limited to, tetrahydrofuran, acetonitrile, dioxane, diethyl ether, methyl t-butyl ether, dichloromethane, etc. For example, the Wittig reaction is carried out in tetrahydrofuran.

In yet another embodiment, the compound of formula (III) or a salt thereof can be prepared by reacting a compound of formula (IX):

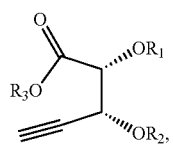
(IX)

or a salt thereof, with methanethiol or a salt thereof, wherein $R_1$ and $R_2$ are each independently a silyl group and $R_3$ is a t-butyl group or $R_3$ is a silyl group.

In an eighth embodiment, the compound of formula (III) can be prepared by a method comprising the steps of:
a) reacting a compound of formula (IX) with methanethiol to form a compound of formula (VIIIa) or a salt thereof:

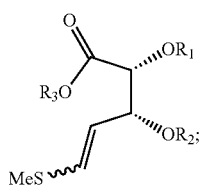
(VIIIa)

b) purifying the compound of formula (VIIIa) or a salt thereof to yield a compound of formula (VIIIb) or a salt thereof:

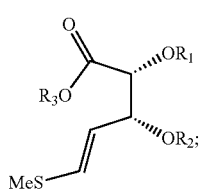
(VIIIb)

c) deprotecting the compound of formula (VIIIb) or a salt thereof to form the compound of formula (III) or a salt thereof.

In a ninth embodiment, the compound of formula (III) can be prepared by a method comprising the steps of:
a) reacting a compound of formula (IX) with methanethiol to form a compound of formula (VIIIa) or a salt thereof:

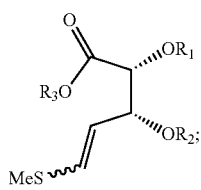
(VIIIa)

b) deprotecting the compound of formula (VIIIa) or a salt thereof to form the compound of formula (VIIIb) or a salt thereof:

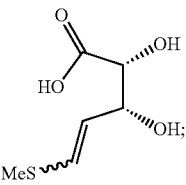
(VIIIb)

c) purifying the compound of formula (VIIIb) or a salt thereof to yield the compound of formula (III) or a salt thereof.

In certain embodiments, the compound of formula (IV) or a salt thereof can be prepared by a method as described in the seventh or eighth embodiment, wherein the compound of formula (IX) is replaced by the compound of formula (IX'):

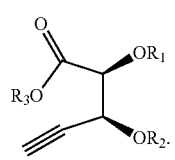
(IX')

In certain embodiments, the compound of formula (I) or (II) or a salt thereof can be prepared by a method as described in the seventh or eighth embodiment, wherein the compound of formula (IX) is replaced by the compound of formula (IX"):

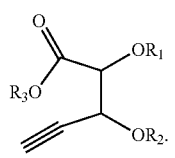
(IX")

In certain embodiments, an alkyne hydrothiolation reaction (i.e., reaction with methanethiol in the eight or ninth embodiment) may be used in the synthetic approach. Alkyne hydrothiolation may be catalyzed by, for example, UV irradiation, a radical initiator, such as azobisisobutyronitrile (AIBN), cationic rhodium and iridium complexes, thorium and uranium complexes, rhodium complexes, caesium carbonate and/or gold.

In certain embodiment, the silyl group described above (e.g., in the fourth, fifth, sixth, seventh, eighth or ninth embodiment) includes, but is not limited to, a triakylsilyl (e.g., dimethylisopropylsilyl, diethylisopropylsilyl, dimethylhexylsilyl, trimethylsilyl, or triisopropylsilyl), tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl). In certain embodiments, the silyl groups is a triakylsilyl group. In certain embodiments, the silyl group is trimethylsilyl or tris(trimethylsilyl)silyl.

Removal of the protecting groups, $R_1$, $R_2$ and $R_3$, depends on the nature of the protecting groups. In one embodiment, the protecting group can be removed by the treatment with a deprotecting reagent that is fluoride and/or an acid. In certain embodiments, the deprotecting reagents, include, but are not limited to, tetra-n-butylammonium fluoride, tris (dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, or periodic acid. In certain embodiment the deprotecting reagent is hydrochloric acid or tetra-n-butylammonium fluoride (TBAF). In certain embodiments, the deprotecting reagent is hydrogen fluoride-pyridine (HF-pyridine).

In certain embodiments, the purification step described in the methods described above (e.g., in the first, second, third, fourth, fifth, sixth, seventh, eighth or ninth embodiment) can be carried out by any suitable purification methods. In certain embodiments, the purification step result in the separation of the corresponding trans-isomer (trans configuration for the double bond) from the cis-isomer. In certain embodiment, the separation of the trans-isomer and cis-isomer can be achieved by chromatography or crystallization. In certain embodiments, the separation of the trans-isomer and cis-isomer can be achieved by HPLC.

EXAMPLES

Material and Methods
Reagents and Instruments

Mass spectrometric grade formic acid (~98%), HPLC grade trifluoroacetic acid (≥99.0%), palladium on activated charcoal (10%), (methylthiomethyl)triphenylphosphonium chloride, anhydrous tetrahydrofuran, sodium bis(trimethylsilyl)amide (1.0 M in tetrahydrofuran), 2,3-cyclohexylidene-L-erythruronic acid, Dowex® 50WX8 (hydrogen form, 100-200 mesh), and sodium phosphate monobasic were obtained from Sigma-Aldrich; HPLC grade methanol, acetonitrile, ethyl acetate, concentrated ammonium hydroxide, and water from Fisher Scientific; Deuterium oxide (99.8%) from Acros. A Fisher Scientific vortex mixer was used for mixing. A Thermo Scientific Sorvall ST 40R centrifuge was used for centrifugation of 50 mL tubes and a Sorvall Legend Micro 21R microcentrifuge for centrifugation of 1.5 mL Eppendorf tubes. A Corning Laboratory magnetic stirrer was used for mixing chemical reactions. Human plasma ($K_2$-EDTA) was obtained from Bioreclamation and stored at −80° C. Human urine was collected in house. An Argonaut SPE DRY™ 96 DUAL evaporator was used for solvent evaporation. All NMR experiments were carried out on a Bruker DRX 500 or 700 MHz instrument.
Chromatography Unless otherwise noted, a Waters Acquity UPLC system equipped with a binary solvent manager, a refrigerated sample manager (set at 12° C.), and a column manager (set at 40° C.) was used for liquid chromatography with a reversed phase column (Waters ACQUITY UPLC® BEH C18, 1.7 μm, 2.1×100 mm). A loop fixed aliquot of 5.0 μL of the final sample solution was injected for each sample. The eluent was directly introduced into the electrospray source of a mass spectrometer. The flow rate was 350 μL/min, and eluent was directly introduced into the electrospray source of a mass spectrometer. Strong needle wash (200 μL) was neat methanol and weak needle wash (600 μL) was a mixture of methanol and water (0.5:99.5). Seal wash was a mixture of methanol and water (10:90).
Chromatography: Basic Conditions Mobile phase A was 6.5 mM ammonium bicarbonate in water and mobile phase B was 6.5 mM ammonium bicarbonate in methanol/water (95:5). Linear gradient elution was carried out with an initial condition of 0% mobile phase B, which was held for 1.50 min. Mobile phase B was then increased to 98% in 0.50 min and maintained for 0.90 min. Mobile phase B reverted to 0% in 0.10 min for equilibration for next injection. The total run time was 4.00 min.

Chromatography: Conditions for Hydrogenated Product, Acidic Conditions

Mobile phase A was 0.1% formic acid in water and mobile phase B was 0.1% formic acid in acetonitrile. Linear gradient elution was carried out with an initial condition of 2% mobile phase B, which was held for 3.00 min. Mobile phase B was then increased to 98% in 0.40 min and maintained for 0.50 min. Mobile phase B reverted to 2% in 0.10 min for equilibration for next injection. The total run time was 5.00 min.
Chromatography: Conditions for Hydrogenated Product, Deuterated Acidic Conditions Mobile phase A was 0.1% formic acid in deuterated water and mobile phase B was 0.1% formic acid in acetonitrile. Linear gradient elution was carried out with an initial condition of 2% mobile phase B, which increased to 7% in 3.00 min. Mobile phase B was then increased to 98% in 0.40 min and maintained for 0.50 min. Mobile phase B reverted to 2% in 0.10 min for equilibration for next injection. The total run time was 5.00 min.
Chromatography: Conditions for Wittig Reaction Products Mobile phase A was 0.1% formic acid in water and mobile phase B was 0.1% formic acid in acetonitrile. Linear gradient elution was carried out with an initial condition of 38% mobile phase B, which was increased to 45% in 3.00 min. Mobile phase B was then increased to 98% in 0.40 min and maintained for 0.50 min. Mobile phase B reverted to 38% in 0.10 min for equilibration for next injection. The total run time was 5.00 min.
Chromatography: Conditions for Double Bond Determination (Sulfoxides)

Mobile phase A was 0.1% formic acid in water and mobile phase B was 0.1% formic acid in acetonitrile. Linear gradient elution was carried out with an initial condition of 20% mobile phase B, which was increased to 30% in 3.00 min. Mobile phase B was then increased to 98% in 1.40 min and maintained for 0.50 min. Mobile phase B reverted to 20% in 0.10 min for equilibration for next injection. The total run time was 6.00 min.
Mass Spectrometry A Thermo Scientific Orbitrap Elite mass spectrometer equipped with a heated electrospray ionization (HESI-II) probe was used in negative mode. The instrument was controlled by Orbitrap Elite™ 2.7 and XCalibur™ 2.2 software (later upgraded 3.0). The heated electrospray source was set with heater temperature at 430° C., sheath gas at 65, auxiliary gas flow rates at 15, sweep gas at 0, ion spray voltage at 3.25 kV, capillary temperature at 350° C., and S-lens RF level at 60%. A resolution of 30,000 was used to collect full scan FTMS spectra with mass range between m/z 100 and 600. All fragmentation experiments were set with scan range between m/z 50 and 200, resolution of 15,000, isolation width of 1.0, activation Q of 0.250, and activation time of 10.0 ms. All mass spectroscopic data were acquired and processed without any lock mass and external mass calibration was used.

The normalized collision energy for $MS^2$ experiment was 28.0 eV for CID $MS^2$ experiment of m/z 177.02 (or 179.03 for deuterium exchange) and 100 eV for the corresponding HCD $MS^2$ experiments. For the CID $MS^3$ experiment of m/z 177.02/159.01 (or 179.03/160.02 and 179.03/161.02 for deuterium exchange), normalized collision energy was 26.0 and 25.0 eV for first and second stage fragmentation, respectively. For the HCD $MS^3$ experiment of m/z 177.02/159.01, normalized collision energy was 26.0 and 100 eV for first (CID) and second (HCD) stage fragmentation, respectively. For the CID $MS^3$ experiment of m/z 177.02/129.02 (or 179.03/130.03 and 179.03/131.03 for deuterium exchange), normalized collision energy was 28.0 and 25.0 eV for first and second stage fragmentation, respectively. For the CID $MS^3$ experiment of m/z 177.02/115.02 (or 179.03/116.03 for deuterium exchange), normalized collision energy was 28.0 and 30.0 eV for first and second stage fragmentation, respectively. For the CID MS³ experiment of m/z 177.02/85.03 (or 179.03/86.04 and 179.03/87.04 for deuterium exchange), normalized collision energy was 28.0 and 21.0 eV for first and second stage fragmentation, respectively. For the HCD MS³ experiment of m/z 177.02/85.03, normalized collision energy was 28.0 and 200 eV for first (CID) and second (HCD) stage fragmentation, respectively.

For the hydrogenated product, the normalized collision energy was 28.0 eV for CID MS² experiment of m/z 179.04 (or 181.05 for deuterium exchange). For the CID MS³ experiment of m/z 179.04/131.03 (or 181.05/132.04 and 181.05/133.05 for deuterium exchange), normalized collision energy was 28.0 and 25.0 eV for first and second stage fragmentation, respectively. For the HCD MS³ experiment of m/z 179.04/131.03, normalized collision energy was 28.0 and 120 eV for first (CID) and second (HCD) stage fragmentation, respectively.

For Wittig reaction products (a mixture of cis and trans protected thioenolethers), the normalized collision energy was 26.0 eV for CID MS² experiment of m/z 257.09 with scan range between m/z 70 and 280.

For sulfoxides and determining the double bond configuration of cis and trans protected thioenolethers, the normalized collision energy was 26.0 eV for CID MS² experiment of m/z 273.08 with scan range between m/z 75 and 280.

Example 1. Structure Elucidation of Plasma and Urine Metabolite Compound A

Sample Preparation

In a 50 mL plastic centrifuge tube were added 6 mL of pooled human plasma and 30 mL of methanol. The mixture was vortexed for about 1 minute and centrifuged at 4° C. for 15 min at 4000 rpm. The supernatant was transferred to a 96-well plate with 500 µL in each well and dried under a gentle stream of nitrogen at 40° C. The residues in five wells were sequentially reconstituted in water (200 mL) with vortexing (1 min each). The mixture was then transferred to a 1.5 mL Eppendorf tube and centrifuged at room temperature for 10 min at 14,000 rpm. The supernatant was then transferred to a sample vial for LC/MS analysis. The urine sample was centrifuged at room temperature for 10 min at 14,000 rpm and the supernatant (diluted with water if needed) was transferred to a sample vial for LC/MS analysis. For retention time comparison of compound A in plasma and urine samples, the injection solutions were adjusted to pH ~3.0 with 1.0 N hydrochloric acid.

Hydrogenation of Compound A

In a 20 mL reaction vial 4 mL urine, 30 mg of palladium on activated charcoal (10%) and a magnetic stir bar were added. The vial was flushed with hydrogen and then equipped with a balloon filled with hydrogen. The reaction mixture was stirred overnight at room temperature and then slowly passed through a syringe filter (0.45 µm). The clear filtrate was transferred to a sample vial for LC/MS analysis.

Structure Elucidation

Figure 2:
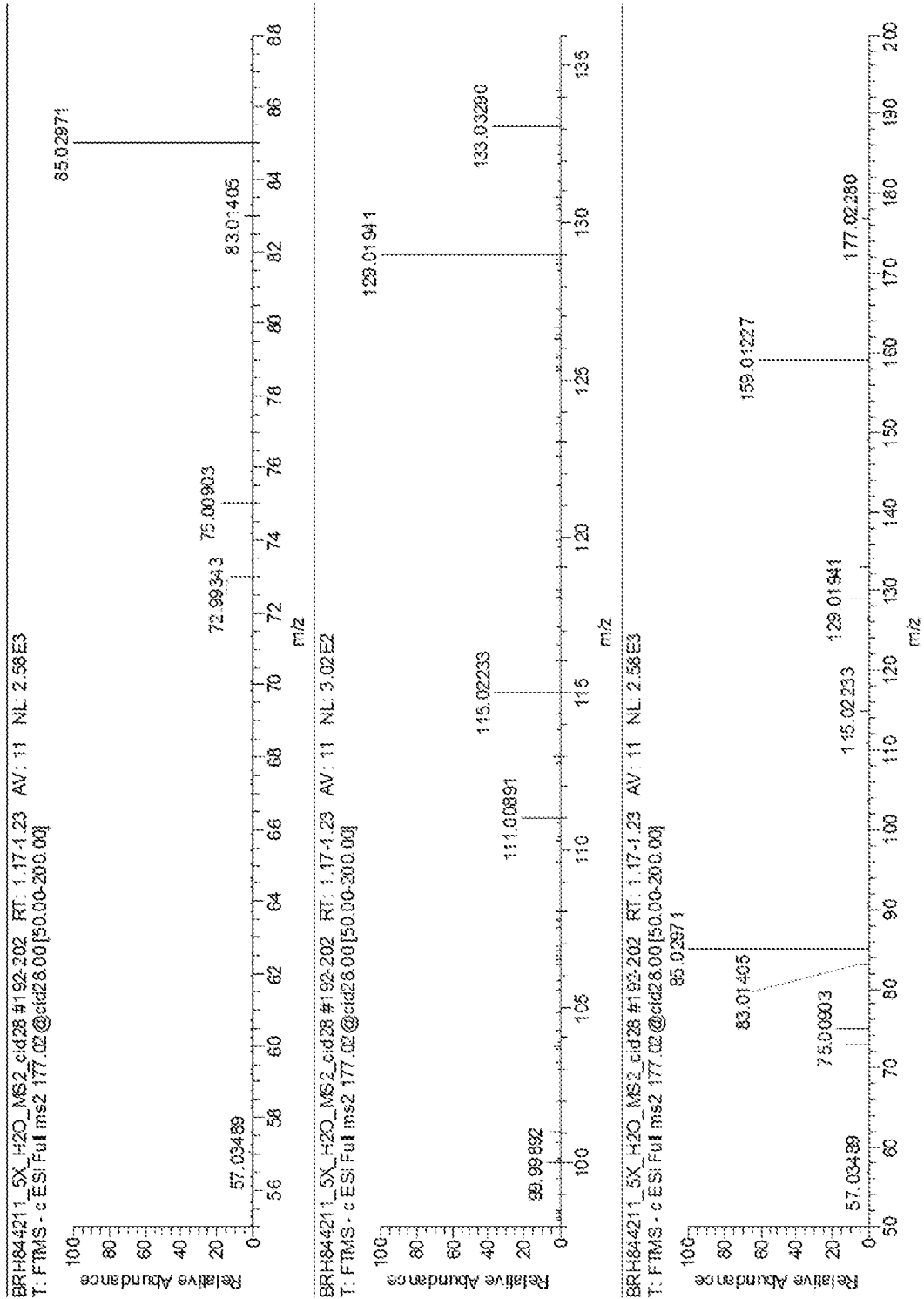
FIG. 2 shows product ion spectrum ($MS^2$) of compound A in a plasma sample with expansions.
Figure 3A:
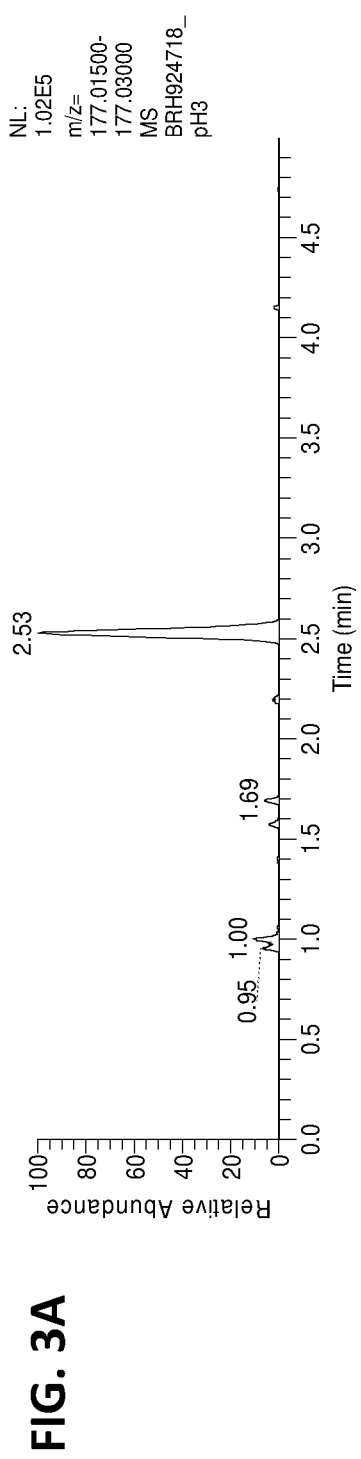
FIG. 3 shows LC/MS chromatograms of compound A in a human plasma sample (A), a human urine sample (B), and in a mixture of human plasma and urine (C) under acidic chromatographic conditions.

An Orbitrap Elite mass spectrometer was used for acquisition of high resolution mass spectra. The formula of the protonated pseudo molecular ion was previously determined to be $C_6H_9O_4S^-$ by accurate mass measurement with a calculated monoisotopic mass of 177.02270. The current study started by optimizing the chromatography conditions using a plasma extract. Compound A retained only slightly on a reversed phased column (1.19 min, FIG. 1) under basic mobile phase conditions using 100% aqueous ammonium bicarbonate. Collision induced dissociation (CID) of the pseudo molecular ion produced many daughter ions across the mass range as shown in FIG. 2. When acidic mobile phase conditions were used, compound A was better retained (2.53 min, FIG. 3A) on the same reversed phase column at 98% water with 0.1% formic acid and 2% acetonitrile with 0.1% formic acid. This method was selected for further investigation.

Figure 3B:
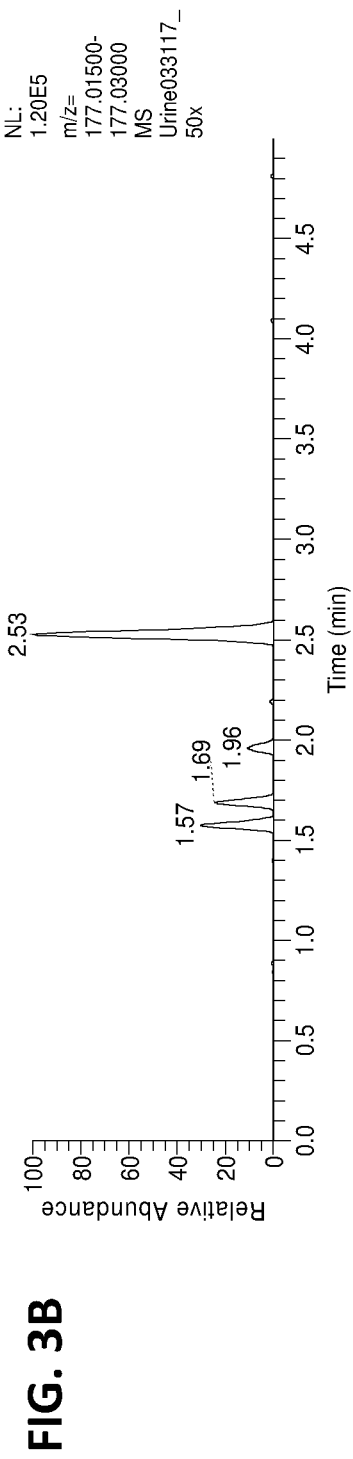
Figure 3C:
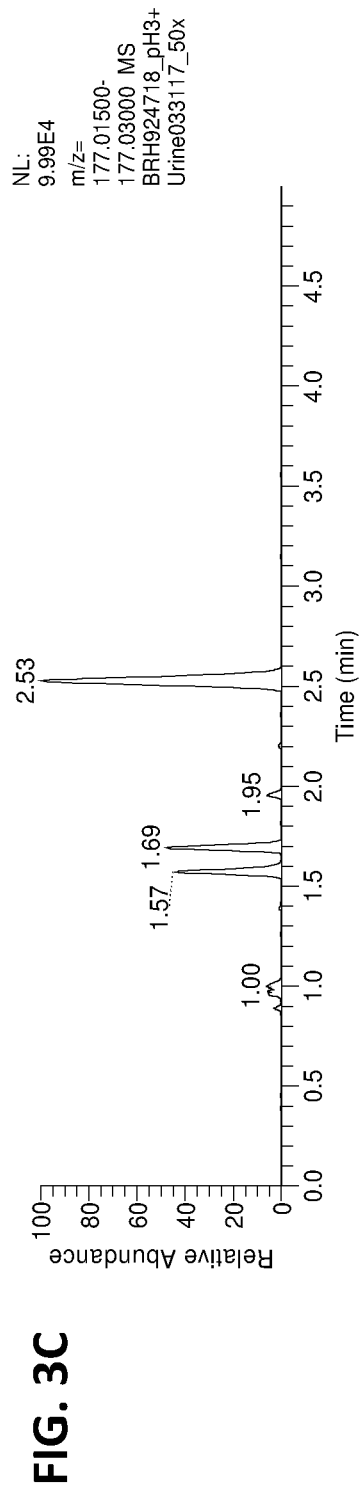

Compound A was found to be present at a low level in plasma. Urine samples were tested, and the peak that matched the retention time of compound A in a plasma extract was stronger in urine (FIG. 3B). The compound in urine co-eluted with compound A in plasma when a mixture of urine and plasma extract was injected (FIG. 3C). Product ion spectrum of the compound in urine (FIG. 4) also matched that of compound A in plasma extract (FIG. 2) very well. These results established that compound A was present in urine at a higher concentration than in plasma. Further analyses were conducted using urine samples.

Figure 4A:
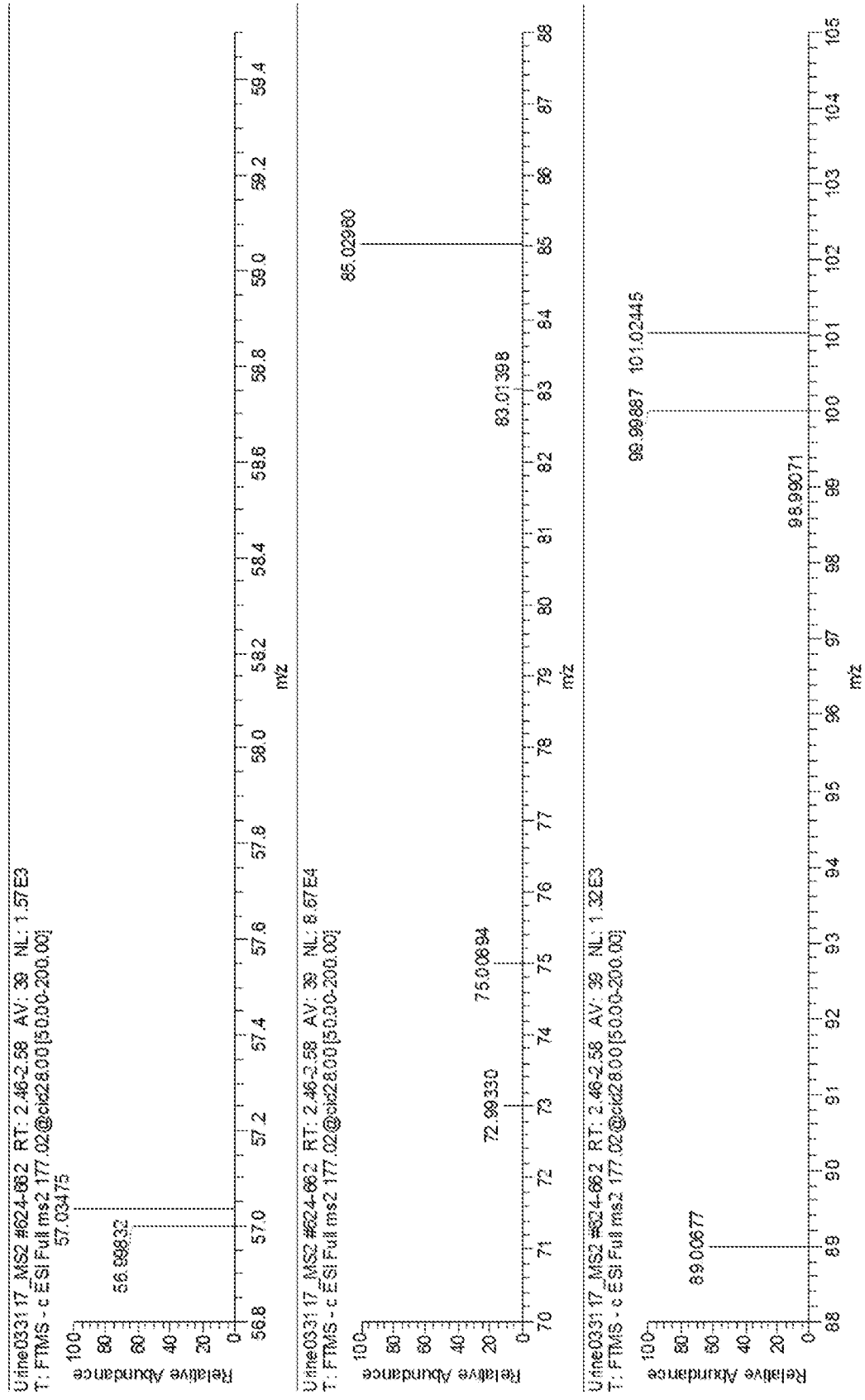
FIGS. 4A and 4B show product ion spectrum ($MS^2$) of compound A with expansions produced using collision-induced dissociation (CID) in a urine sample.
Figure 4B:
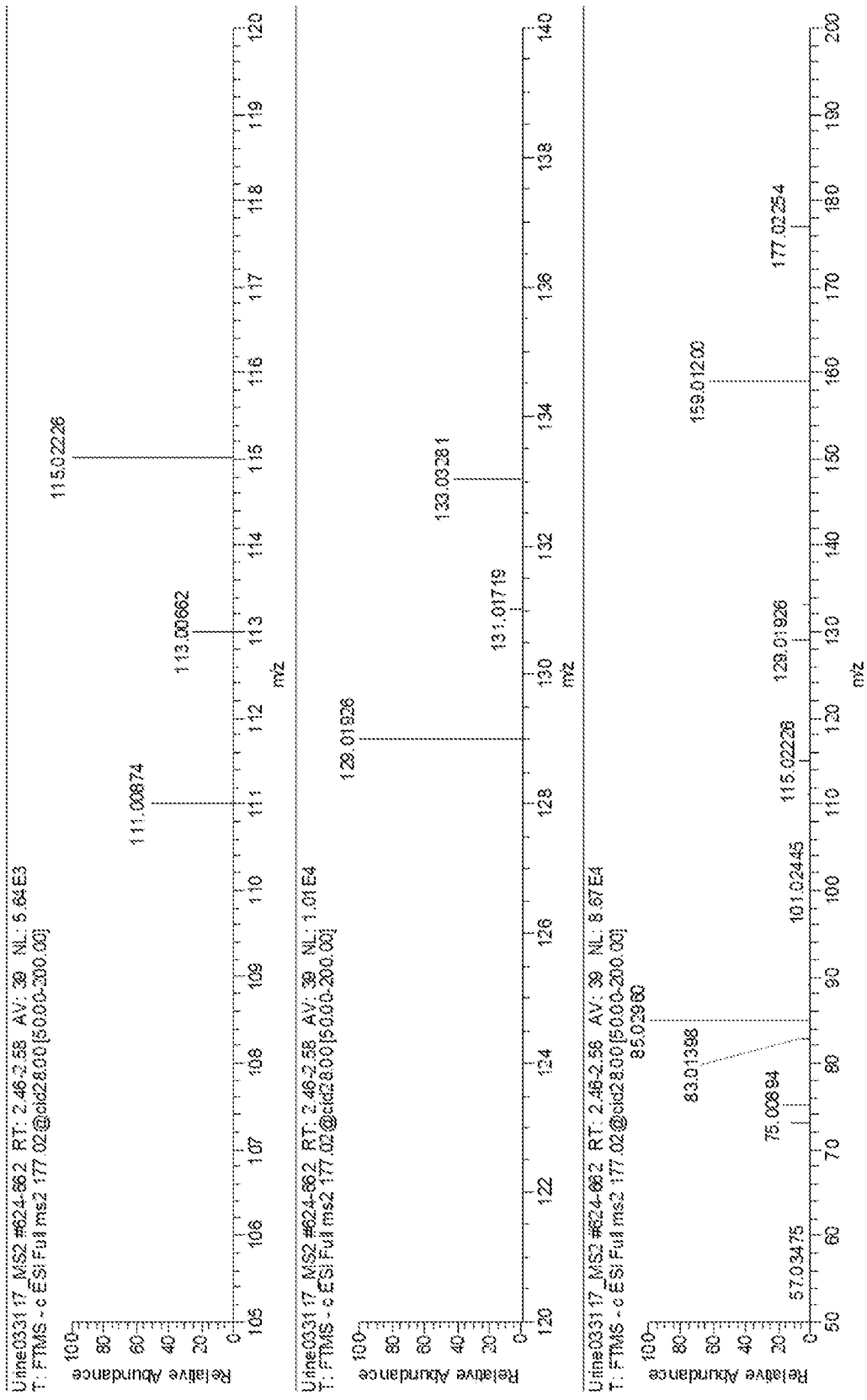
Figure 5A:
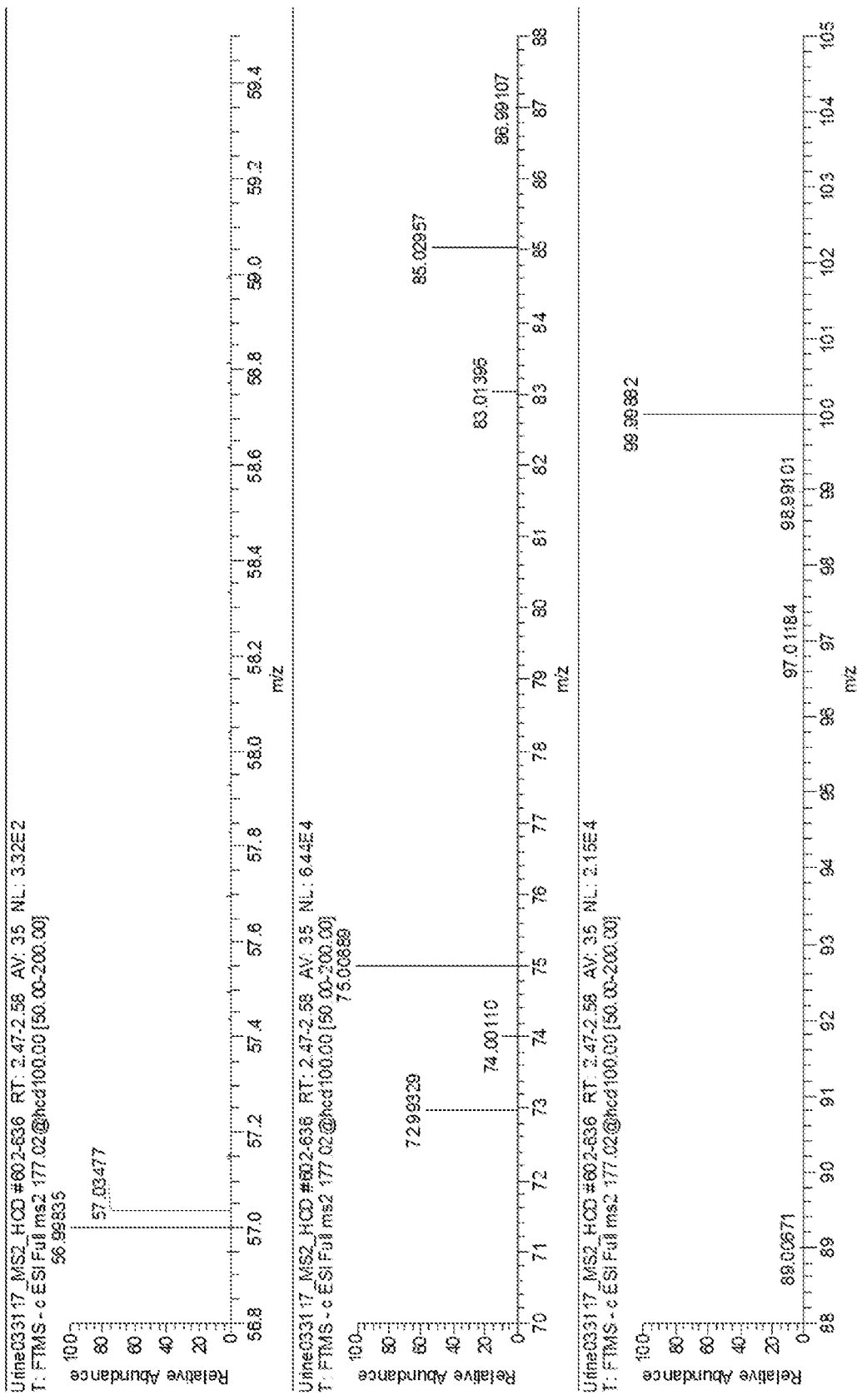
FIGS. 5A and 5B show product ion spectrum ($MS^2$) of compound A with expansions produced using high-energy collision-induced dissociation (HCD) in a urine sample.
Figure 5B:
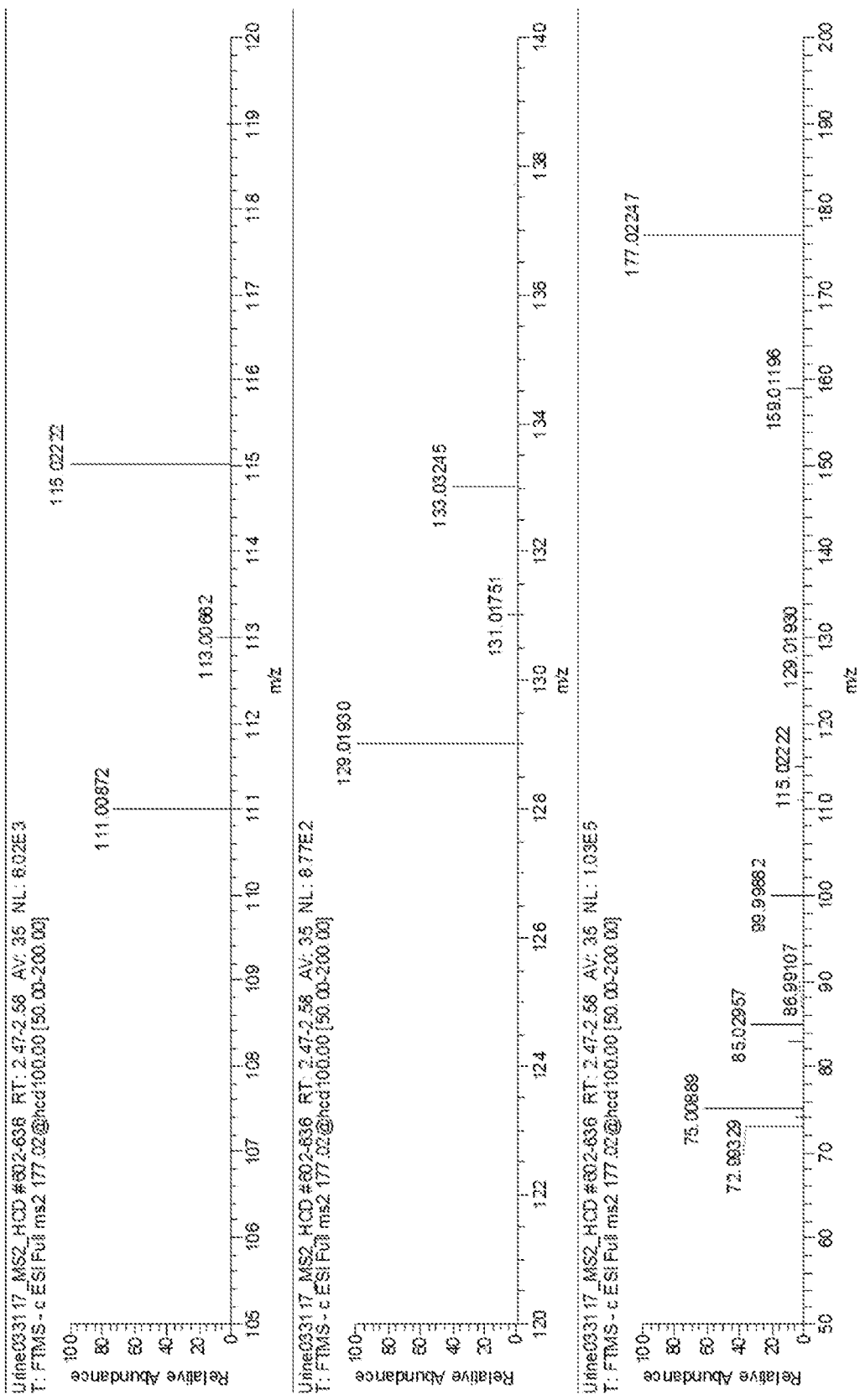
Figure 6A:
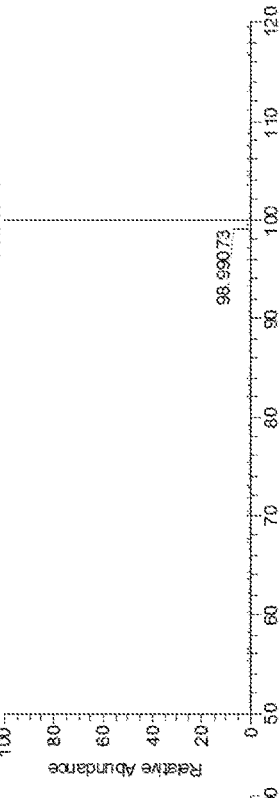
FIGS. 6A, 6B, 6C, 6E, 6D and 6F show $MS^3$ spectra of compound A of m/z 85 (A), 115 (B), 129 (C), 159 (D) using CID and of m/z 85 (E), 159 (F) using HCD in a urine sample.
Figure 6B:
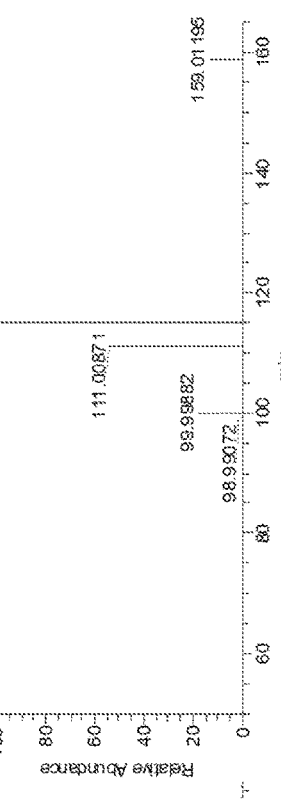
Figure 6C:
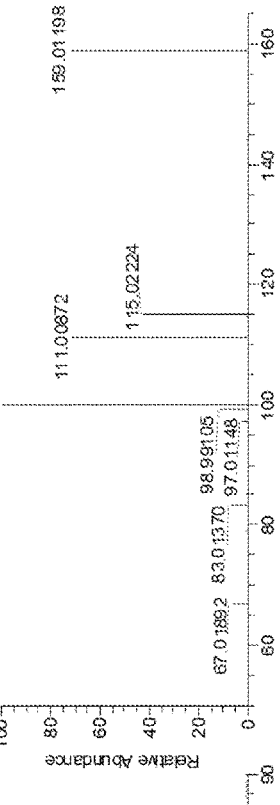
Figure 6D:
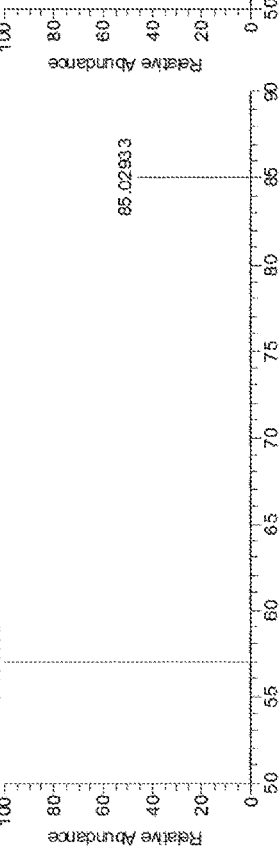
Figure 6E:
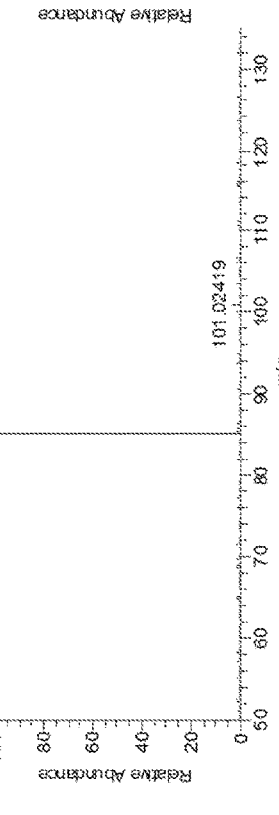
Figure 6F:
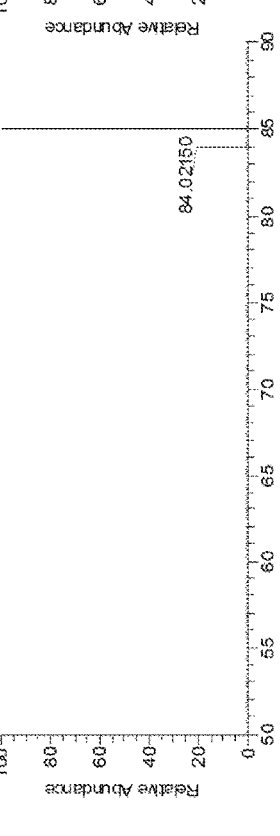

The CID product ion spectrum of the pseudo molecular ion produced 17 daughter ions with different intensities as shown in FIG. 4, which are m/z 159, 133, 131, 129, 115, 113, 111, 101, 100, 99, 89, 85, 83, 75, 73, 57.03, and 57.00. Another product ion spectrum (FIG. 5) by high-energy collision-induced dissociation (HCD) generated three additional daughter ions (m/z 97, 87, and 74). Further fragmentation spectra of the m/z 85, 115, 129, and 159 ions (CID MS³, FIG. 6 A-D) and m/z 85 and 159 ions (HCD MS³, FIG. 6 E-F) detected two more ions (m/z 84 and 67) and established the relationships of certain ions.

Based on the rationalization of these fragments and their formation pathways, a chemical structure for compound A was proposed. The proposed structure has an undetermined double bond configuration and undetermined stereochemistry as shown below:

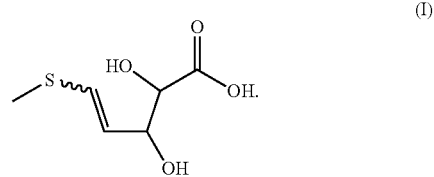

(I)

Compound A has close structural similarity to 5-methyl-thioribose (MTR), which is biosynthesized from 5'-methyl-thioadenosine (MTA).

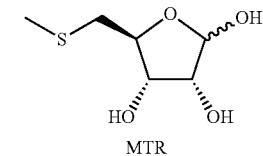

MTR

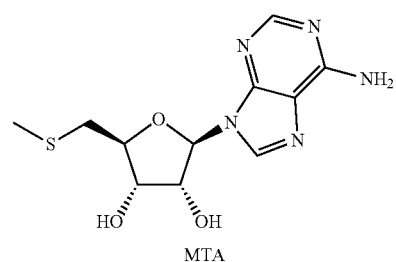

MTA

Stereochemistry of compound A was assigned based on its structural similarity to MTR and MTA, and the formula was determined to be represented by the following structure:

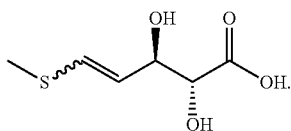

(B)

Determination of Double Bond Configuration

Figure 7:
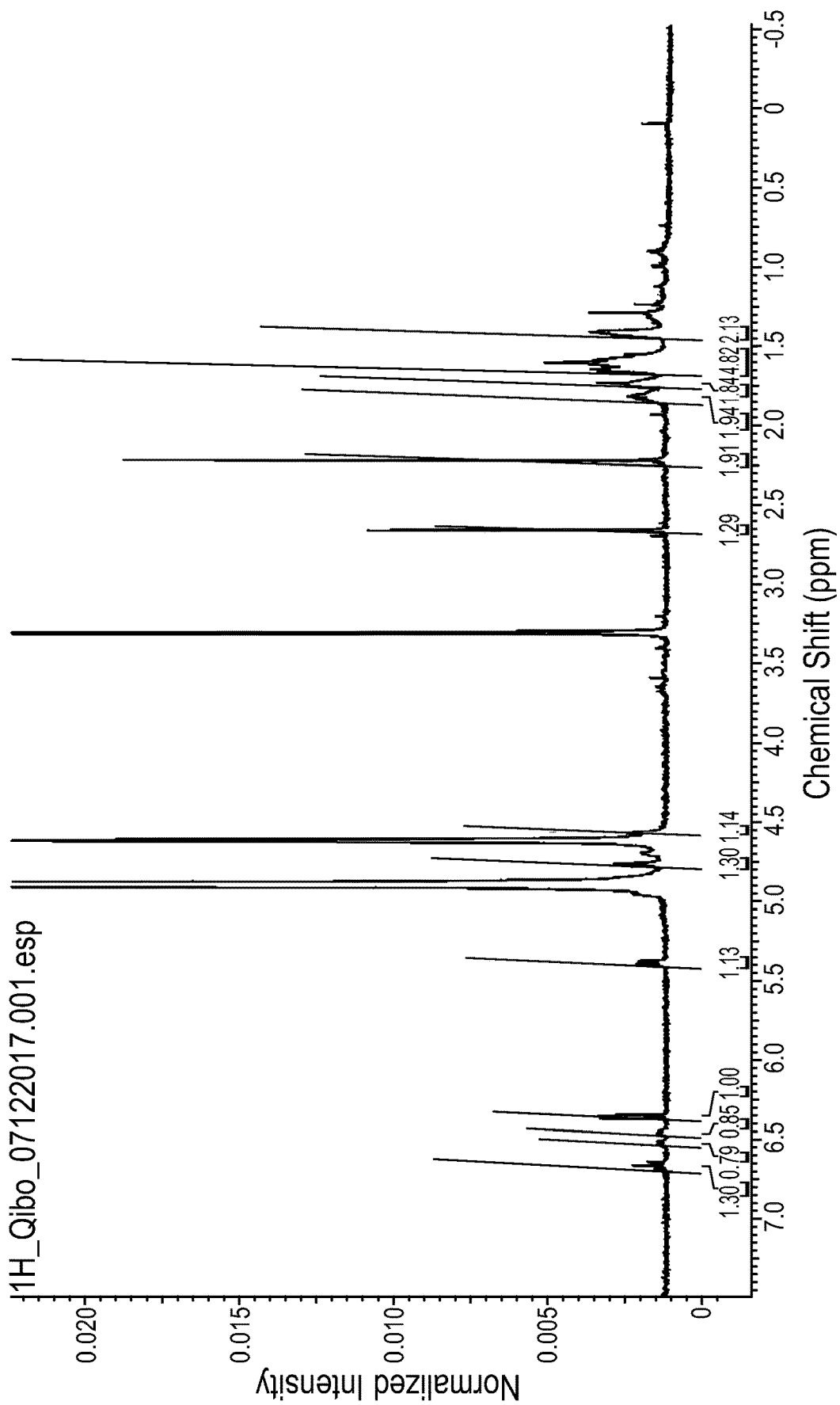
FIG. 7 shows $^1H$ NMR (700 MHz) of the concentrated residue of the collected fraction of the early eluting peak, showing the sulfoxides.
Figure 8:
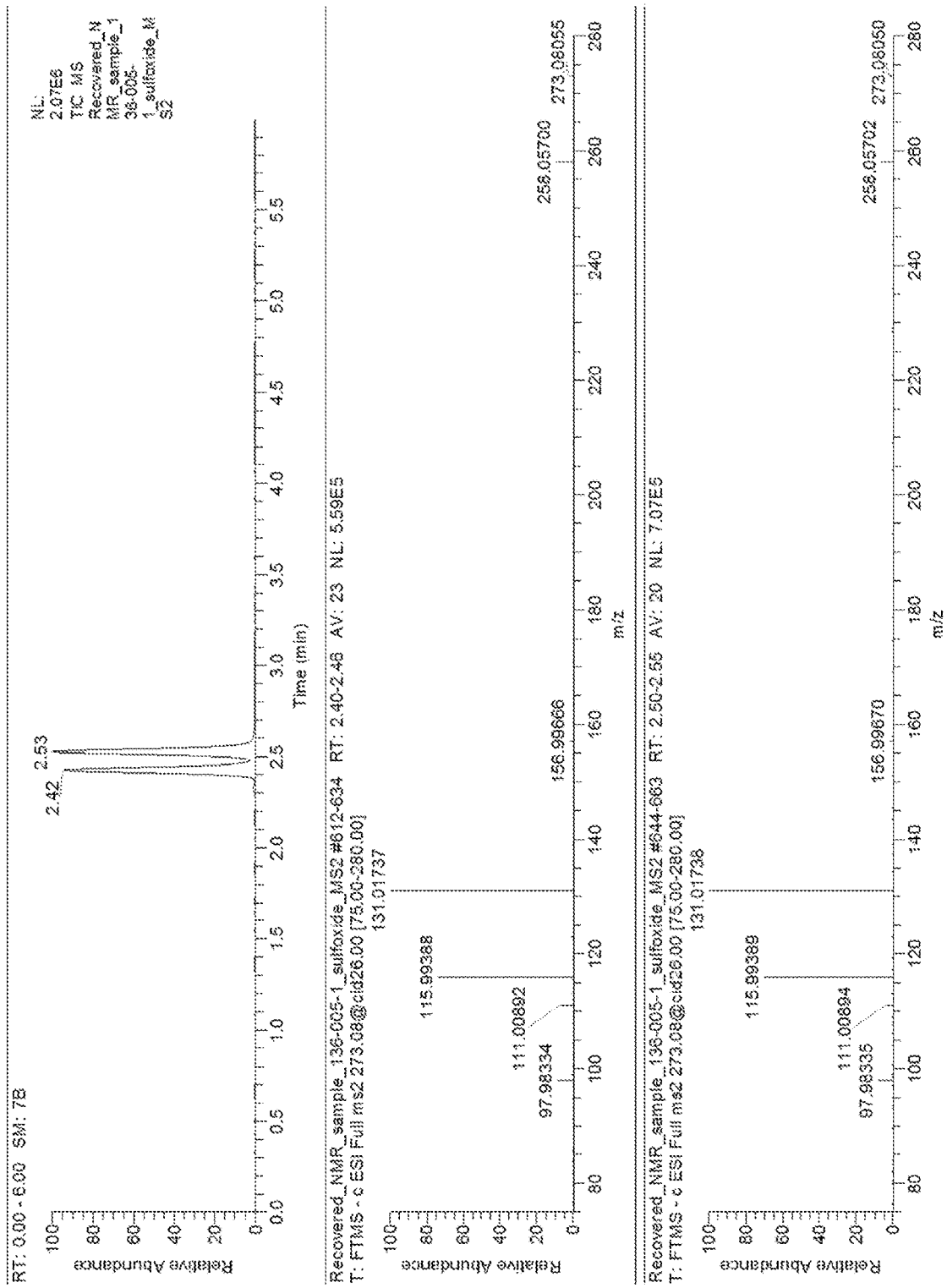
FIG. 8 shows LC/MS/MS chromatogram and spectra of the concentrated residue of the collected fraction, showing sulfoxides at 2.42 and 2.53 min and their corresponding $MS^2$ spectra.

A portion of the mixture of protected trans and cis thioenolethers as synthesized in Example 2, Method 1, was chromatographed semi-preparatively under neutral mobile phase conditions, and the eluent of the early eluting isomer was collected and evaporated to dryness (referred to as HPLC purified sample). When the resulting residue was analyzed by $^1$H NMR (FIG. 7), the spectrum unexpectedly did not match that of either isomer (cis or trans) of the protected thioenolethers. Further analysis using COSY, LC/MS, and LC/MS$^2$ spectra indicated that a pair of diastereomeric sulfoxides (2.42 and 2.53 min) was formed during the purification process of the early eluting isomer (LC/MS$^2$, FIG. 8). The $^1$H NMR spectrum showed a coupling constant of 15 Hz between the olefinic protons, indicating the configuration of the double bonds in the pair of diastereomeric sulfoxides was trans. Since the sulfoxides were formed from the early eluting protected thioenolether during the purification process, the double bond configuration of the early eluting isomer of the protected thioenolether was determined to be trans.

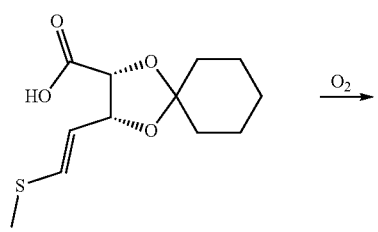

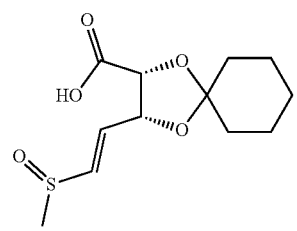

Figure 9:
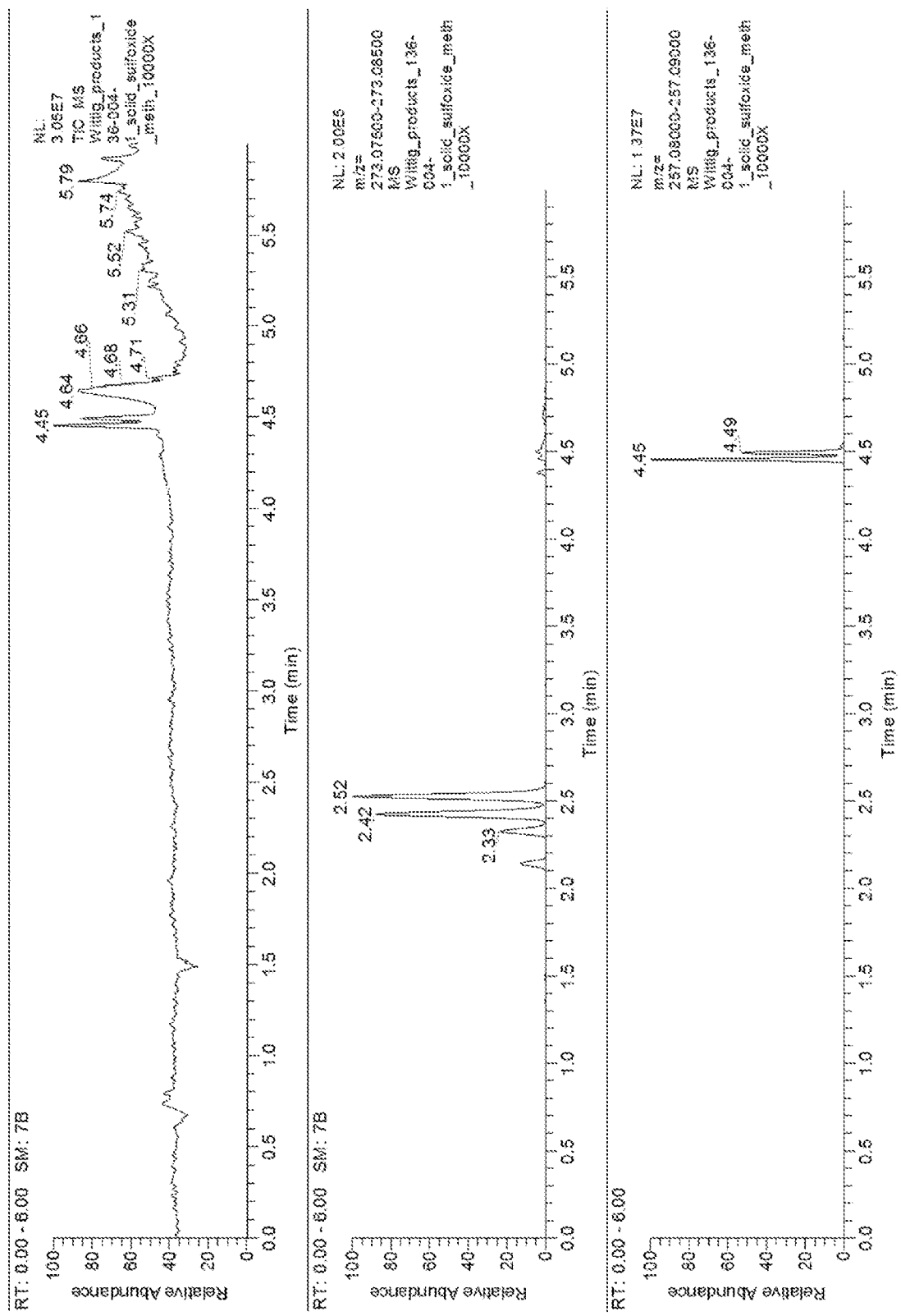
FIG. 9 shows LC/MS chromatograms of a mixture of Wittig products showing the presence of sulfoxides as trace components at 2.14, 2.32, 2.42, and 2.53 min and the protected trans and cis thioenolethers at 4.45 and 4.49 min, respectively.
Figure 10:
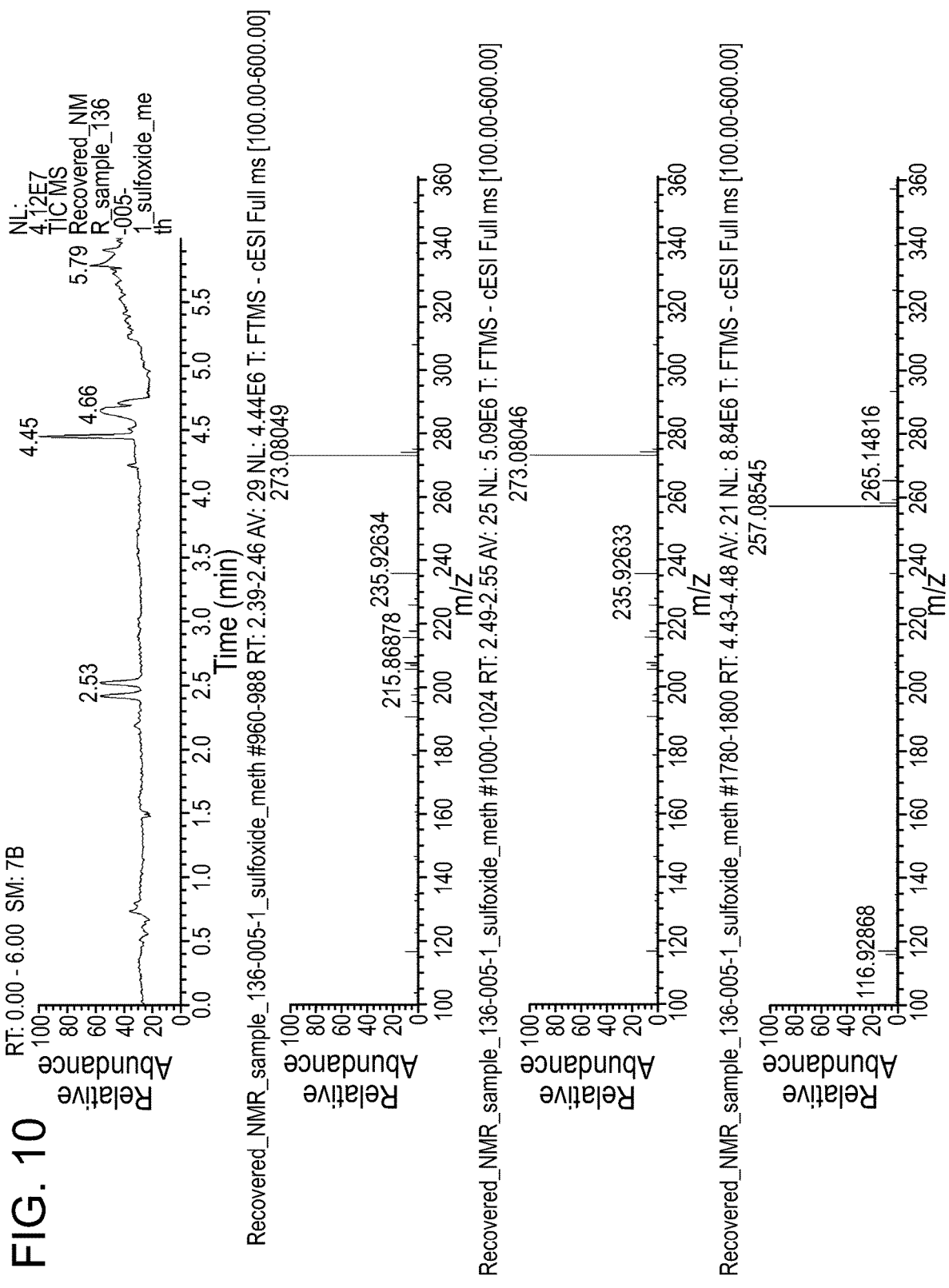
FIG. 10 shows LC/MS chromatogram and spectra of the concentrated residue of the collected fraction, showing sulfoxides at 2.42 and 2.53 min with m/z 273.08049 and 273.08046, respectively, and the protected trans thioenolether as a trace component at 4.45 min with m/z 257.08545.
Figure 11:
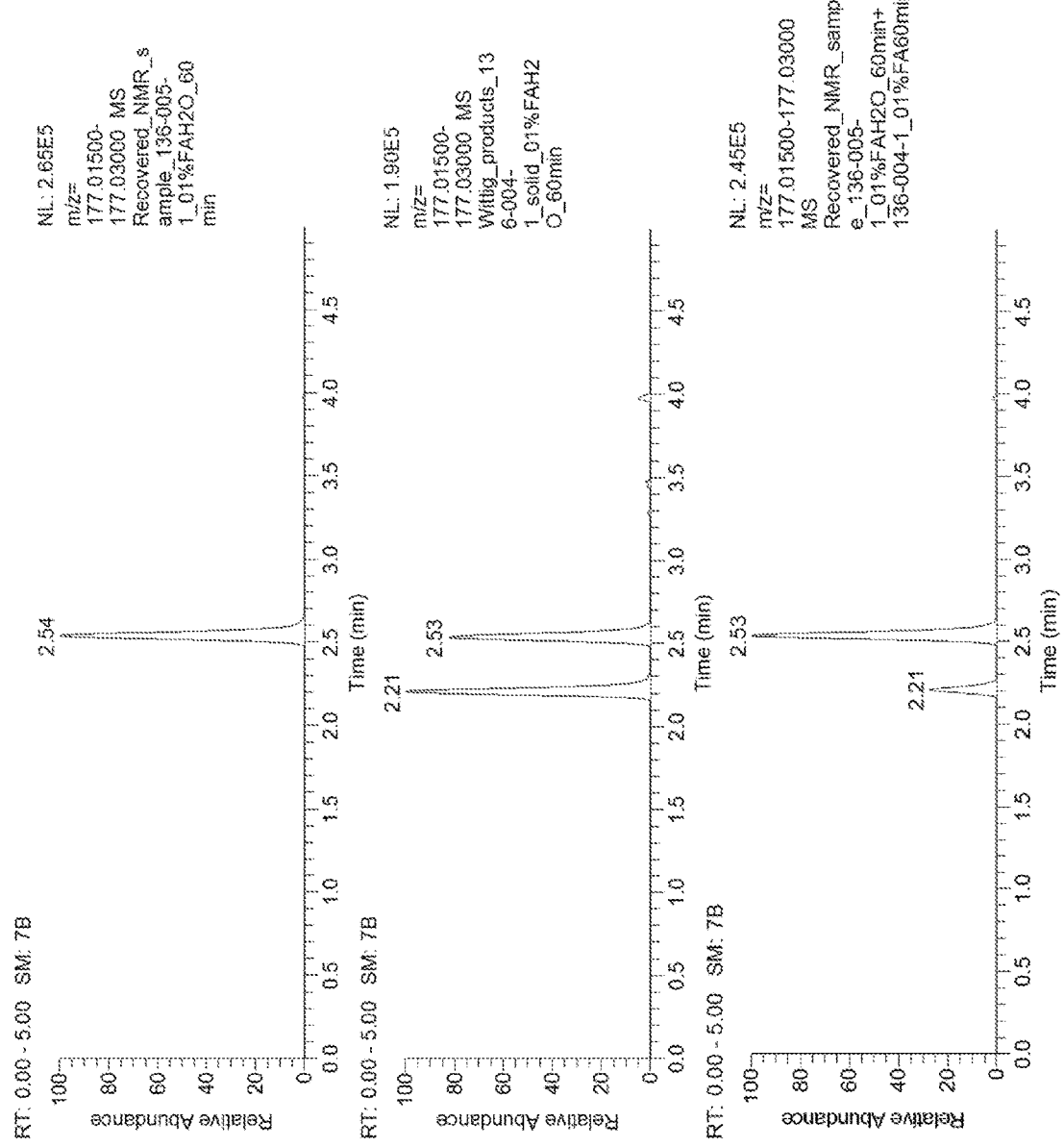
FIG. 11 shows LC/MS chromatograms of trans-DMTPA (2.54 min, top), a mixture of cis and trans DMTPAs (2.21 and 2.53 min, respectively, middle), and their co-injection (bottom).

The mixture of protected trans and cis thioenolethers as synthesized in Example 2, Method 1, was analyzed by LC/MS. As shown in FIG. 9, the protected trans and cis thioenolethers were detected at 4.45 and 4.49 min, respectively, by LC/MS. Although the protected trans thioenolether was not observed in the HPLC purified sample by $^1$H NMR, it was clearly detected at 4.45 min by LC/MS analysis (FIG. 10), indicating incomplete oxidation of the protected trans thioenolether to sulfoxides. The protected trans thioenolether was still present in the HPLC purified sample but at a much lower level relative to the sulfoxides. When the HPLC purified sample was treated under slightly acidic conditions, removal of the protection group from the protected trans thioenolether was achieved to form the trans-DMTPA, as detected by LC/MS at 2.54 min. The trans-DMTPA coeluted with the late eluting isomer of a mixture of cis and trans DMTPAs (FIG. 11). Therefore, the late eluting DMTPA isomer was determined to have the trans double bond configuration. Thus, compound A was determined to have the trans double bond configuration as it also coeluted with the late eluting isomer. The structure of compound A with stereochemistry assigned is shown below as formula (III).

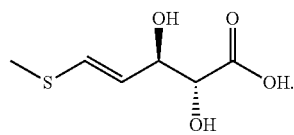

(III)

Possible fragmentation pathways from the deprotonated pseudo molecular ion of compound A are proposed as shown in Schemes 1 and 2.

Scheme 1. Possible fragmentation pathways

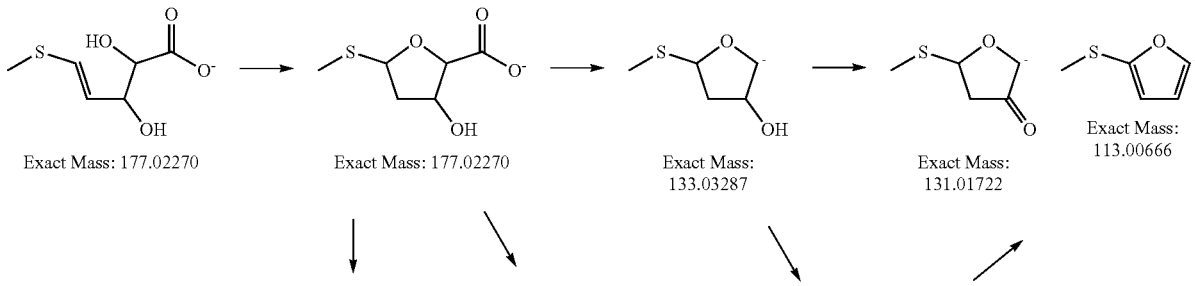

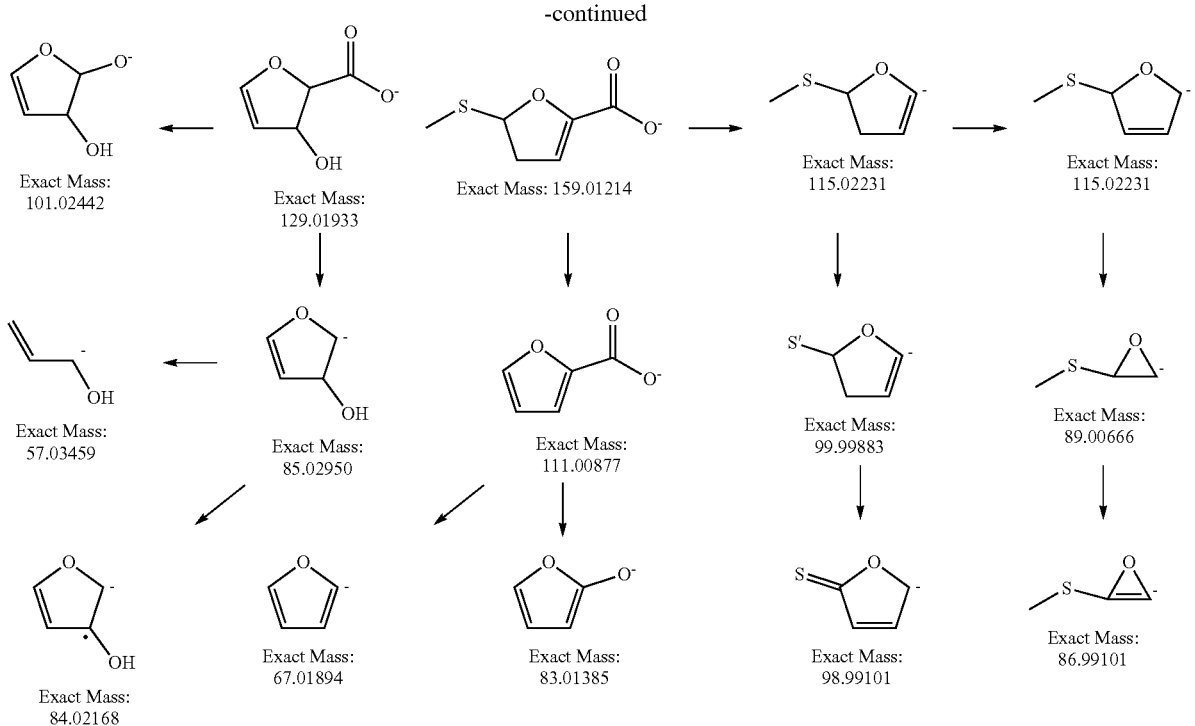
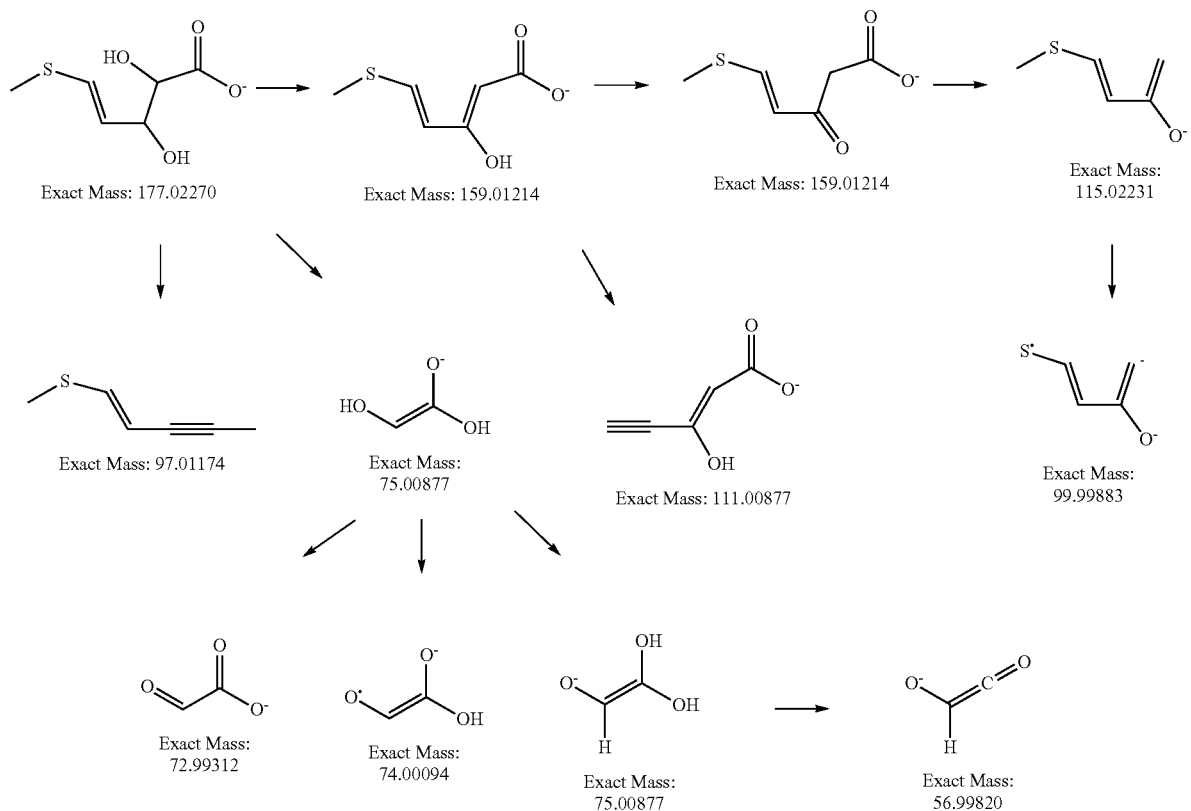
Scheme 2. Possible fragmentation pathways

Structure Verification by Deuterium Exchange

Figure 12:
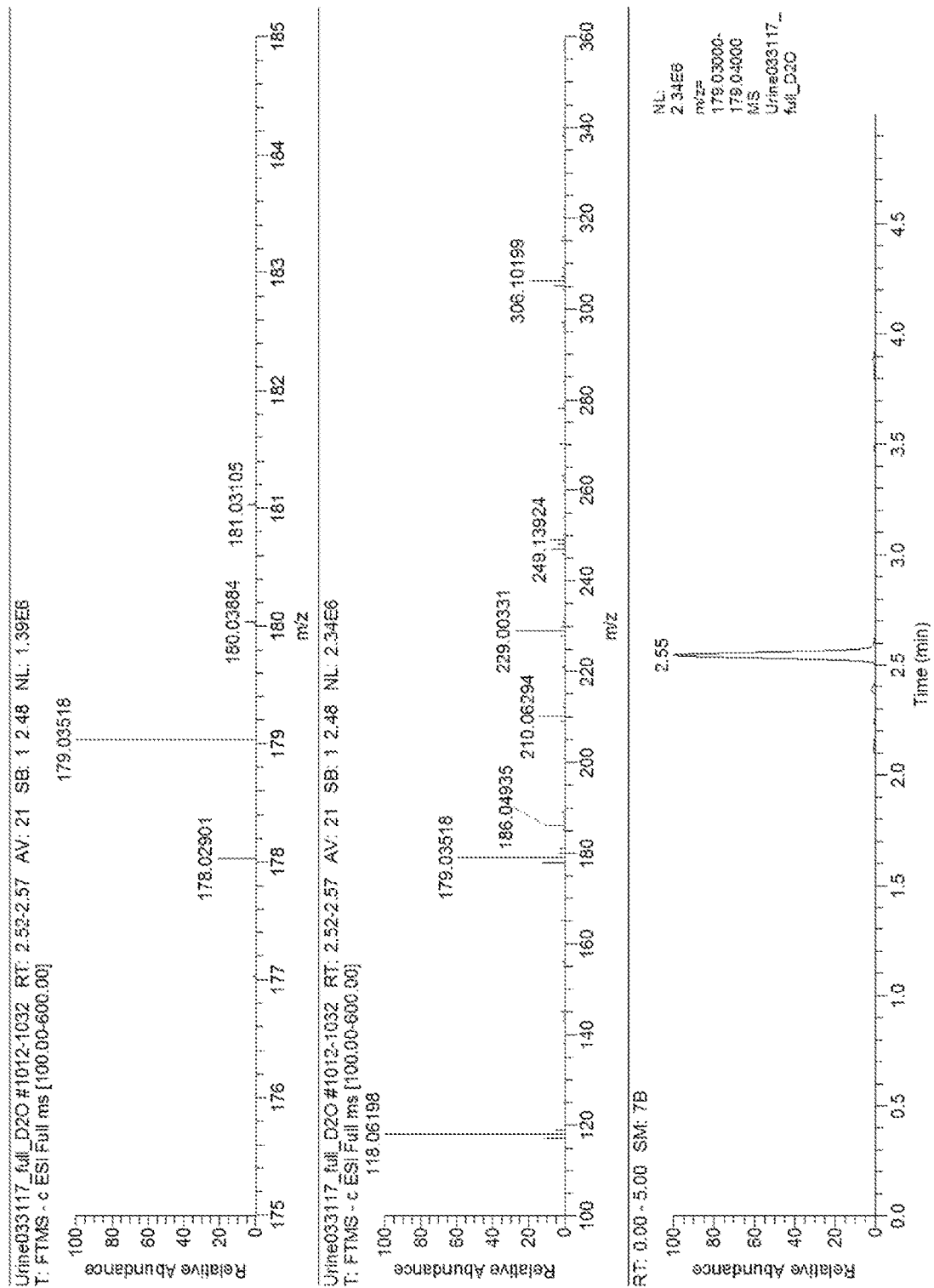
FIG. 12 shows full scan LC/MS chromatogram and mass spectrum of deuterium exchanged compound A in a urine sample.
Figure 13A:
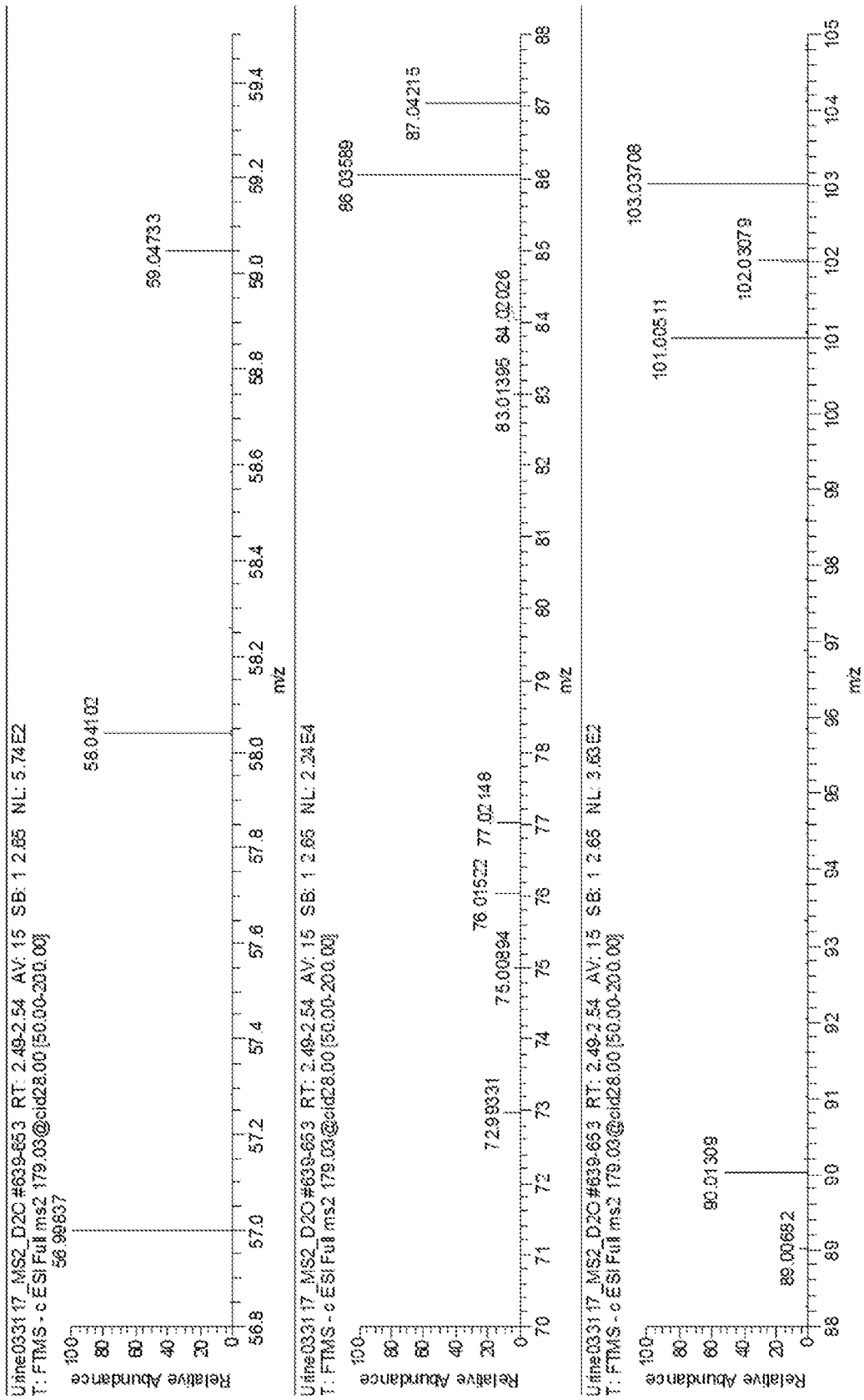
FIGS. 13A and 13B show $MS^2$ spectrum of deuterium exchanged compound A with expansions using CID in a urine sample.
Figure 13B:
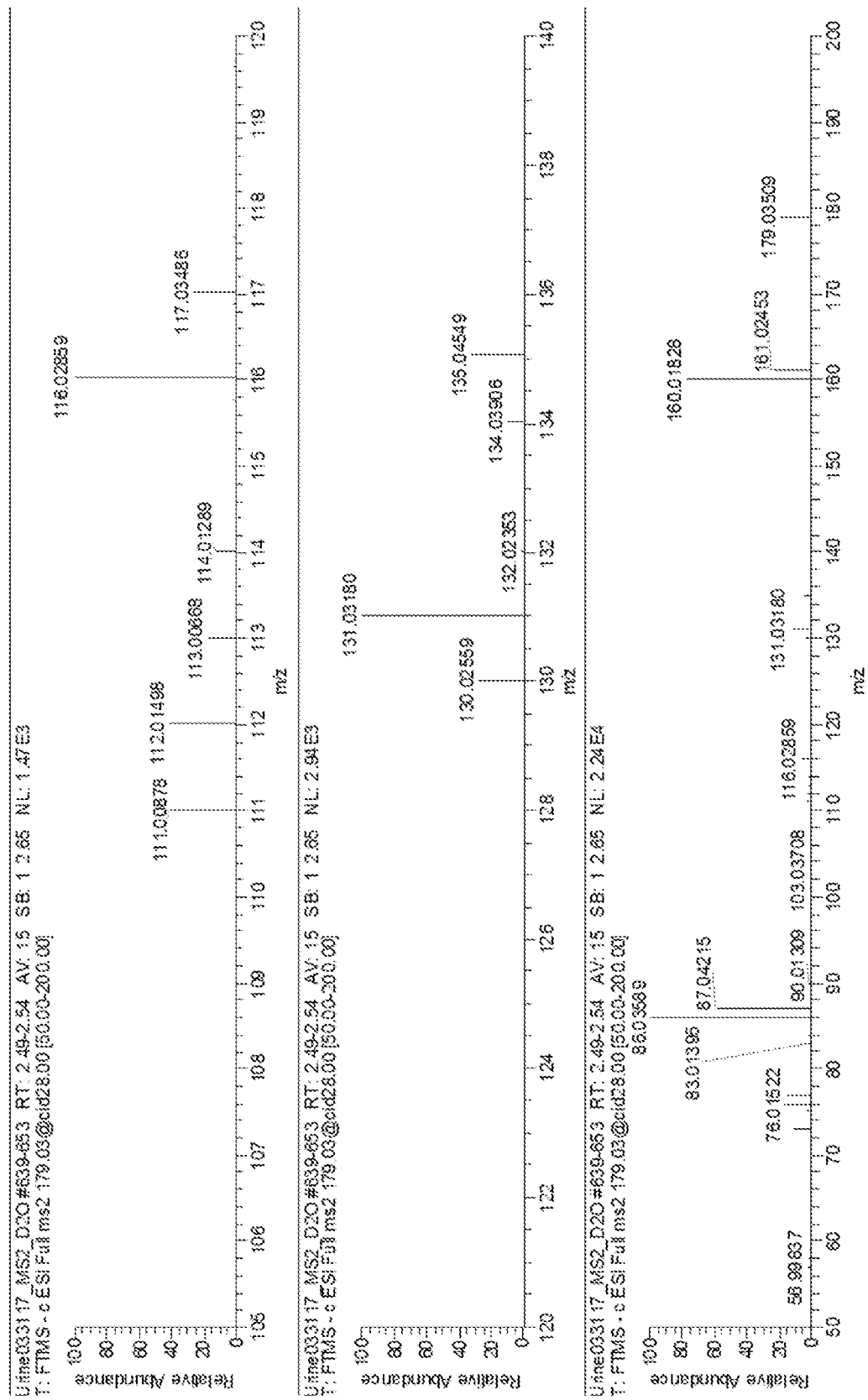
Figure 14A:
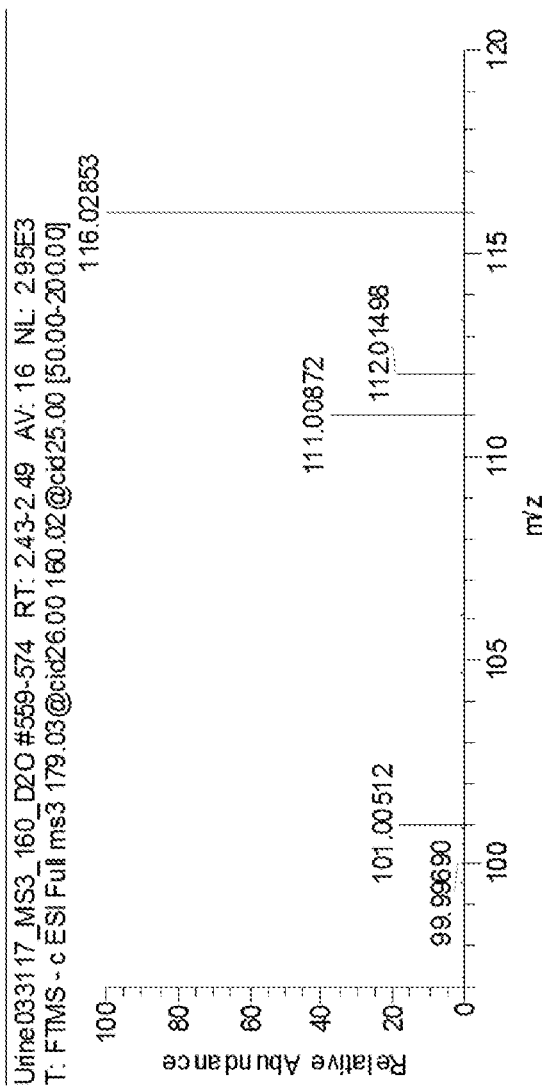
FIGS. 14A and 14B show $MS^3$ spectrum of m/z 160 of deuterium exchanged compound A using CID in a urine sample (A) with expansions (B).
Figure 14B:
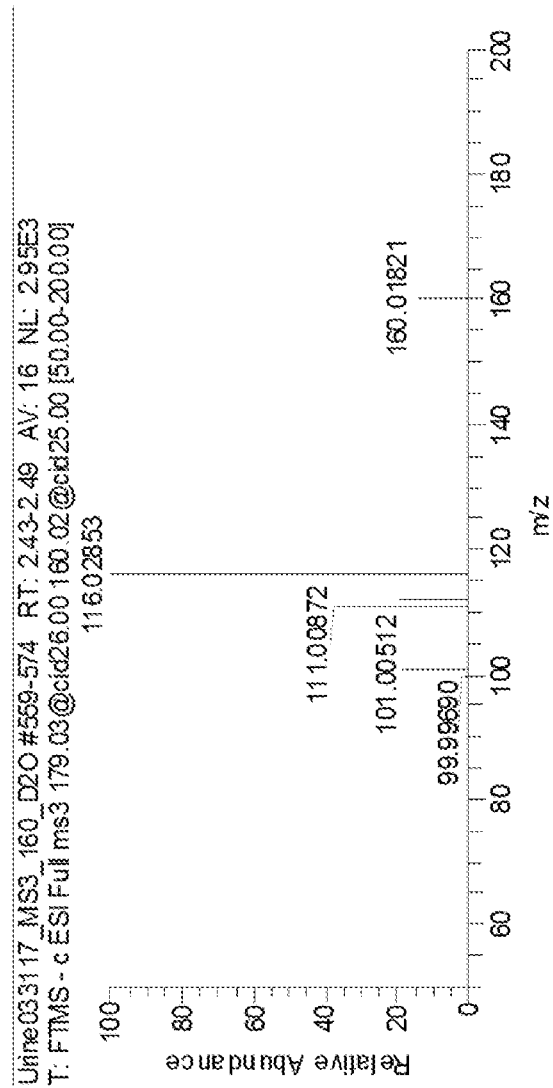
Figure 15A:
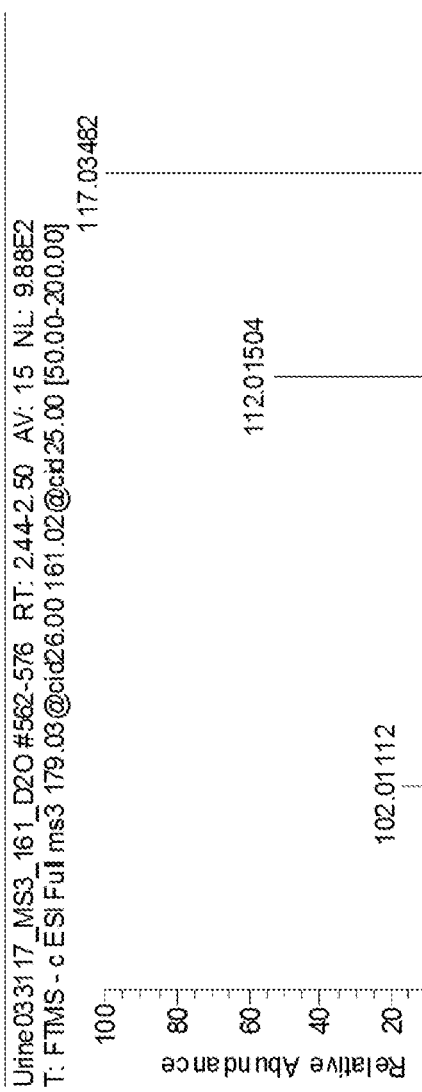
FIGS. 15A and 15B show $MS^3$ spectrum of m/z 161 of deuterium exchanged compound A using CID in a urine sample (A) with expansions (B).
Figure 15B:
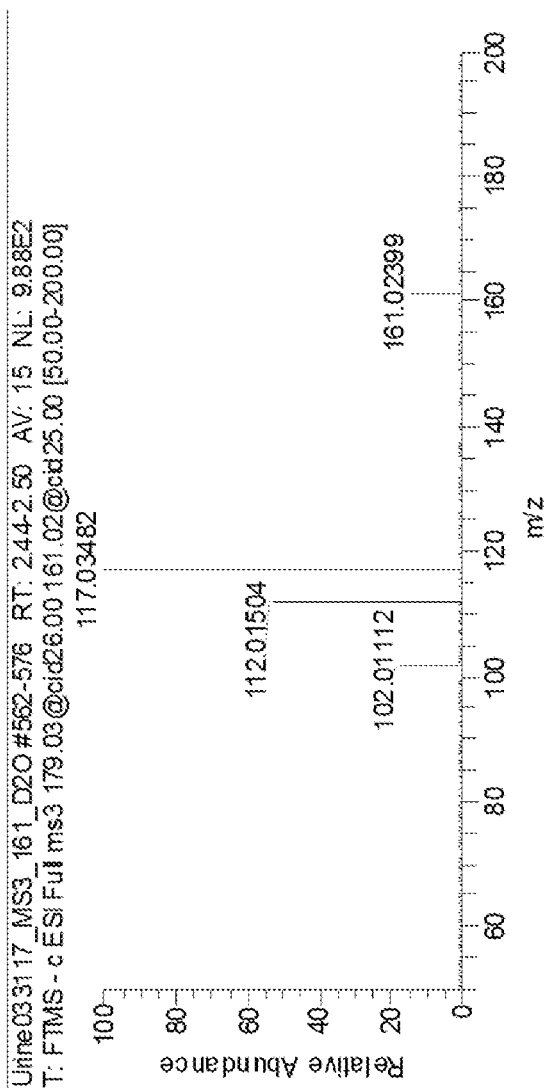
Figures 16A, 16B, 16C, 16D, 16E:
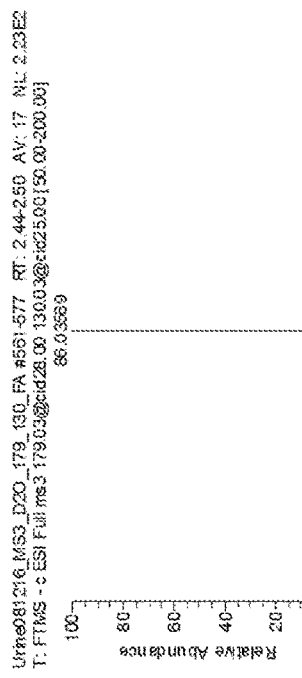
FIGS. 16A, 16B, 16C, 16D and 16E show $MS^3$ spectra of m/z 130 (A), 131 (B), 86 (C), 87 (D), and 116 (E) of deuterium exchanged compound A using CID in a urine sample.

The proposed structure for compound A was verified by a deuterium exchange experiment. Briefly, the mobile phase of chromatography was changed to deuterated solvent and the urine extract was analyzed again. Full scan mass spectrum was acquired and a new ion with m/z 179.03518 ion (−0.4 ppm off the calculated value for $C_6H_7D_2O_4S^-$) was detected as the major species of deuterated compound A (FIG. 12), consistent with the proposed structure. Product ion spectrum (MS$^2$) of the m/z 179 ion (FIG. 13) and MS$^3$ spectra of the corresponding m/z 160 (FIG. 14), 161 (FIG. 15), 130, 131, 86, 87, and 116 (FIG. 16 A-E) ions are shown. Doubly deuterated fragments were detected at m/z 161, 135, 131, 117, 103, 102, 87, 77, and 59, while a single deuterium was incorporated into m/z 160, 132, 130, 116, 114, 112, 102, 101, 100, 90, 86, 84, 76, and 58. Fragments without incorporated deuterium were observed at m/z 113, 111, 89, 83, 75, 72, and 57. The detection of the m/z 160 and 161 ions indicates the loss of HOD and $H_2O$, respectively, from the doubly deuterated parent ion. The formation of the m/z 161 ion may occur due to a deuteron on an oxygen exchanging with a proton on a carbon before the loss of $H_2O$. All these ions can be satisfactorily rationalized into the originally proposed fragmentation pathways (see Schemes 3-5), providing convincing evidence for validity of the proposed structure of compound A.

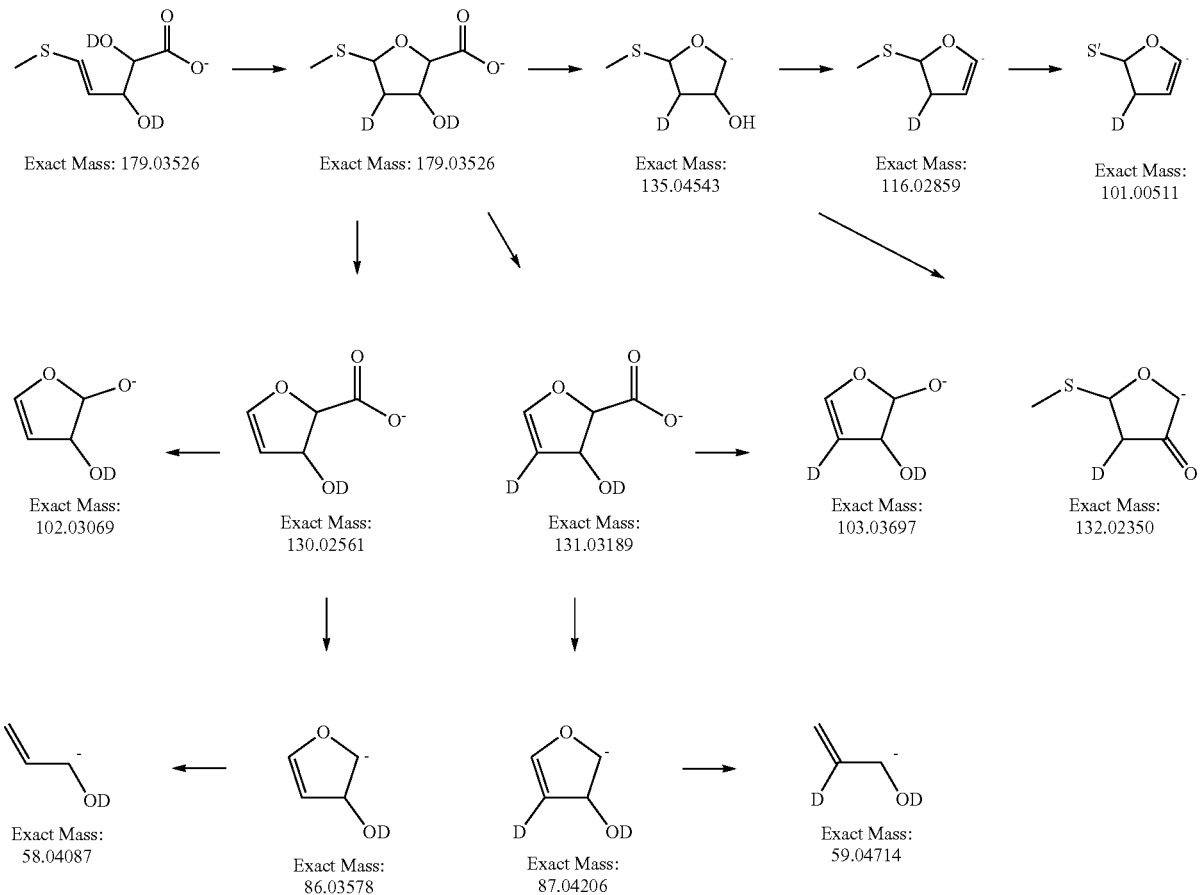

Scheme 3. Possible fragmentation of pathways of deuterated analog.

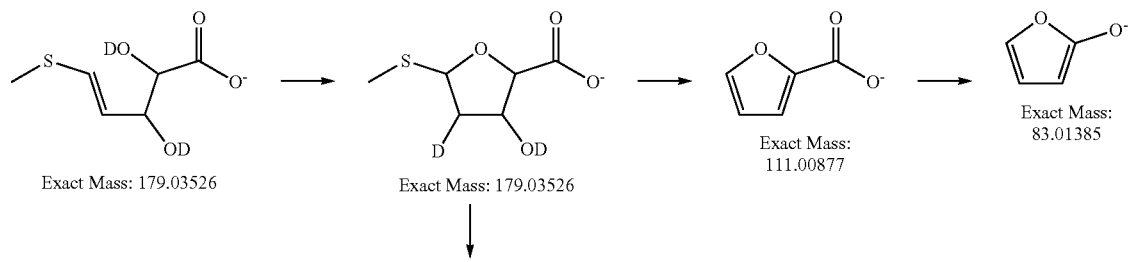

Scheme 4. Possible fragmentation pathways of deuterated analog.

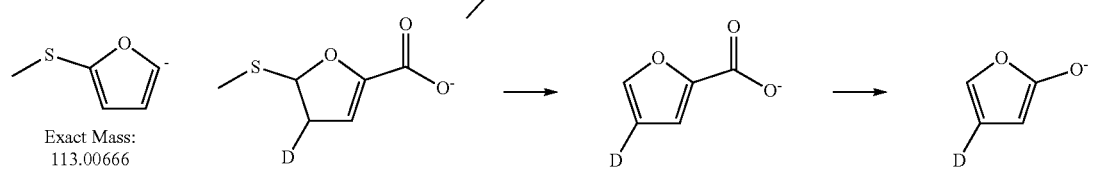
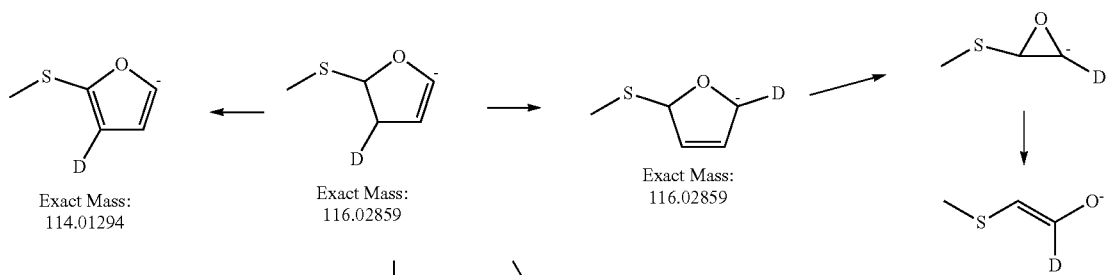
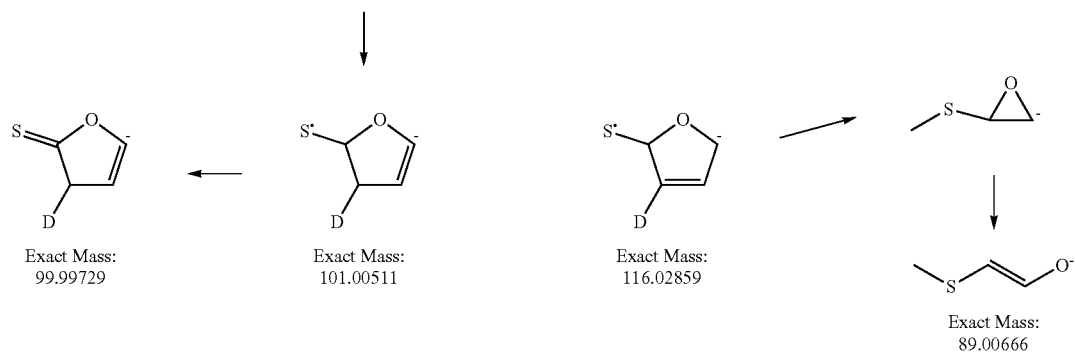
Scheme 5. Possible fragmentation pathways of deuterated analog.
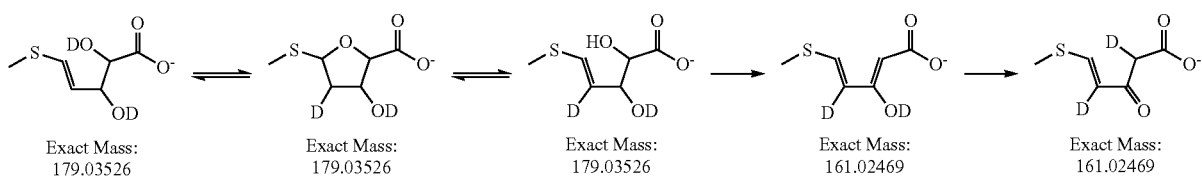

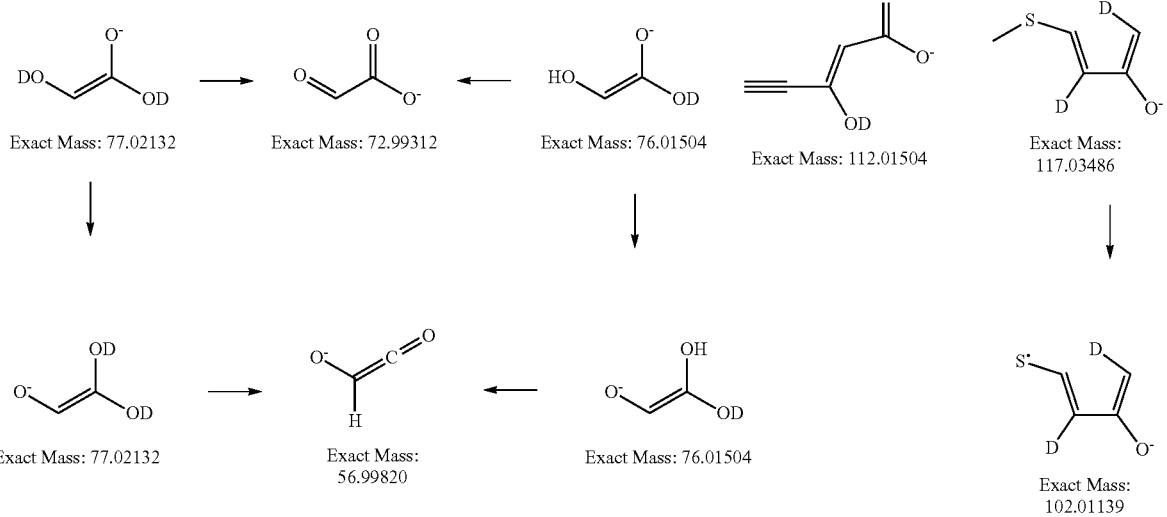

Structure Verification by Hydrogenation

Figure 18A:
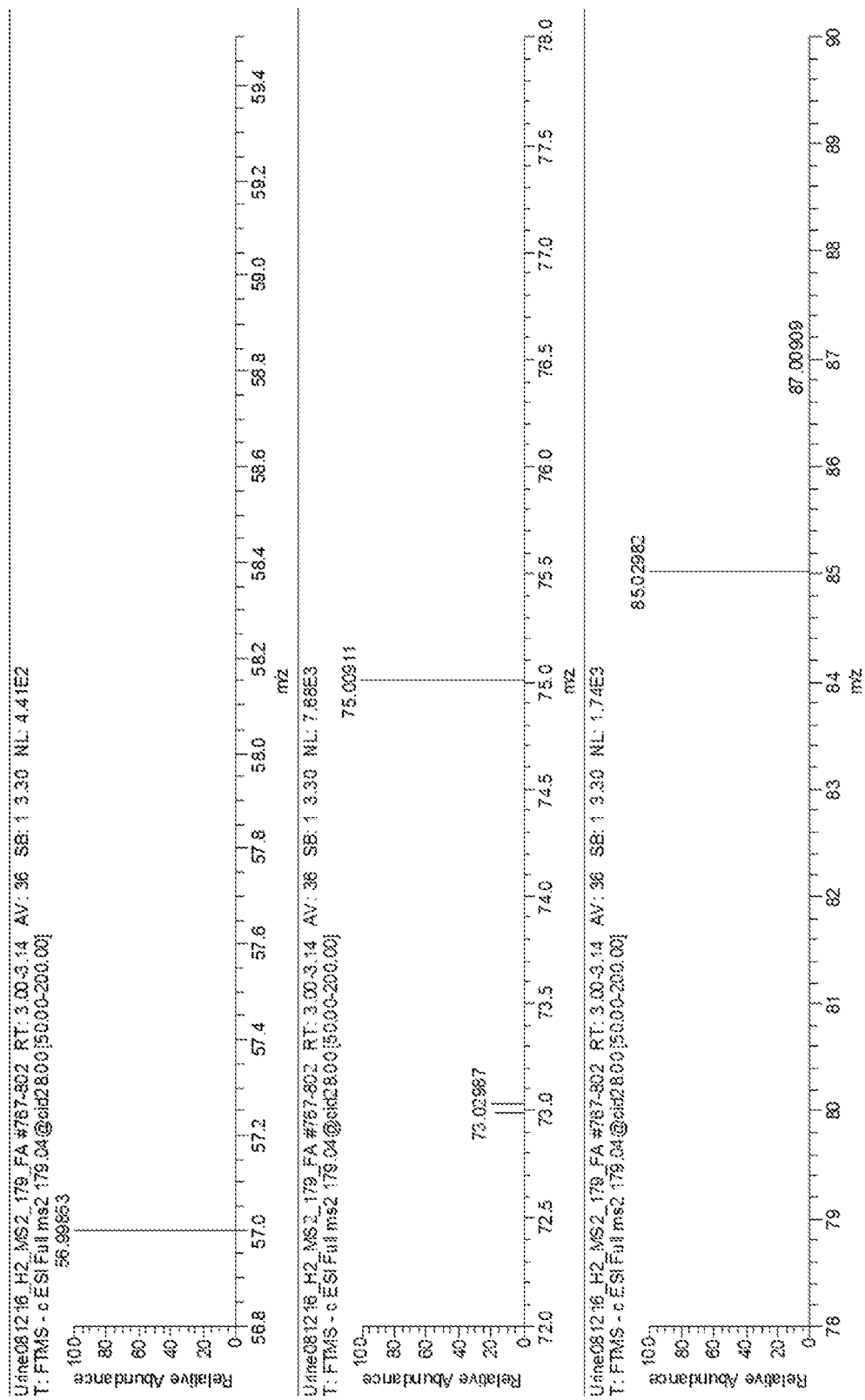
FIGS. 18A and 18B show product ion spectrum ($MS^2$) of hydrogenated compound A with expansions using CID in a urine sample.
Figure 18B:
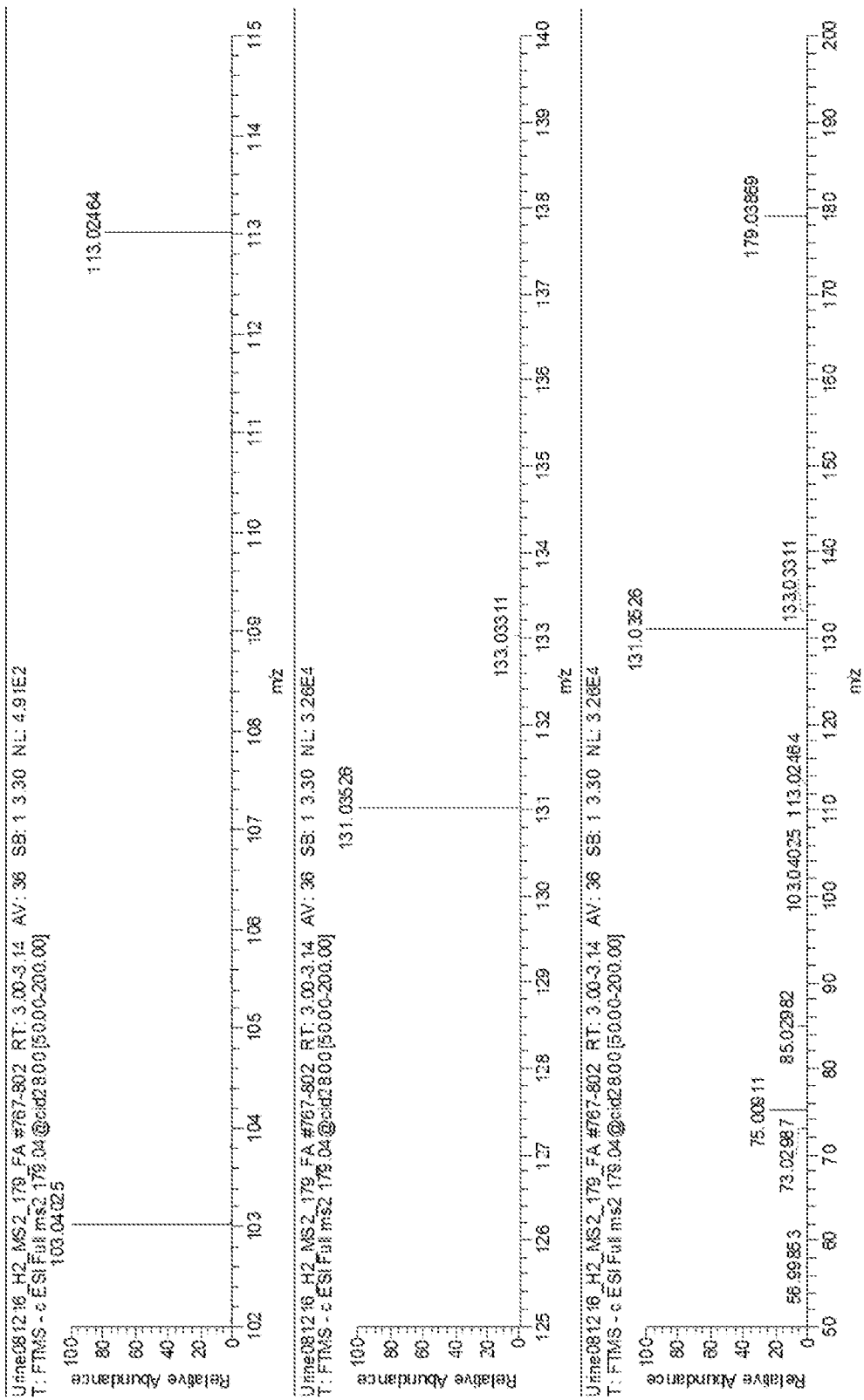
Figure 19A:
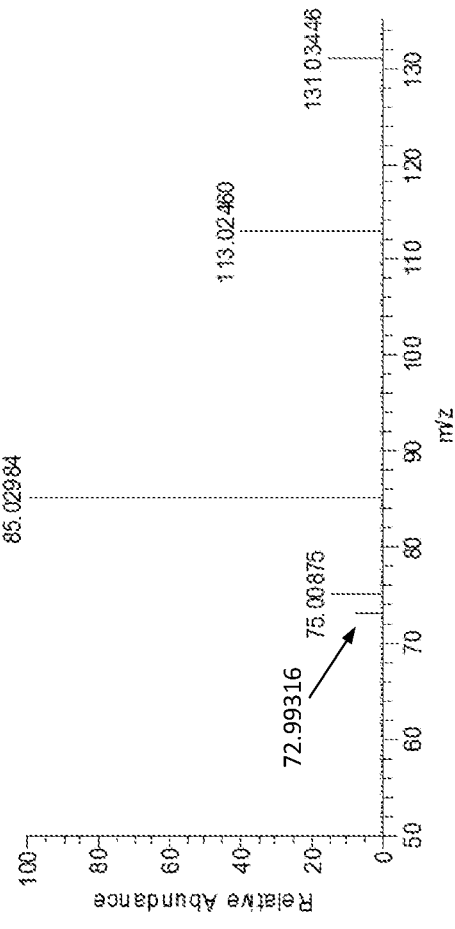
FIGS. 19A and 19B show $MS^3$ spectra of m/z 131 of hydrogenated compound A using CID (A) or HCD (B) in a urine sample.
Figure 19B:
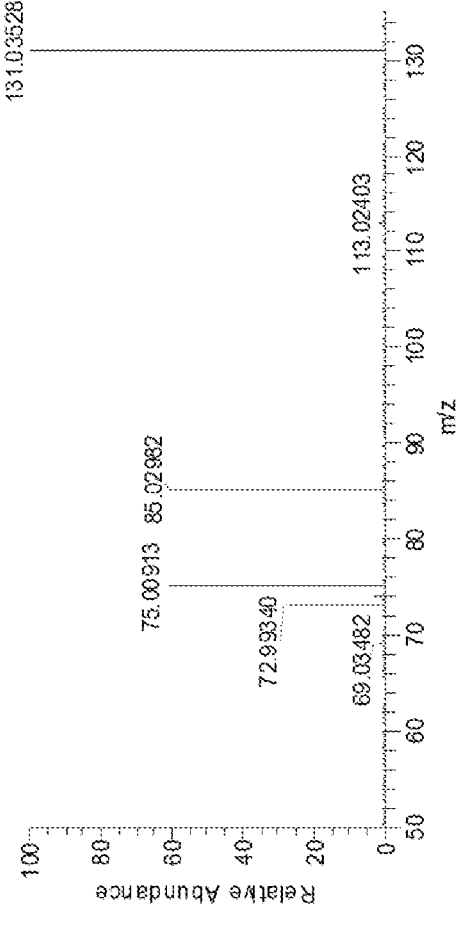

The proposed structure contains a carbon-carbon double bond and was further confirmed by a saturation experiment. A urine sample was subjected to catalytic hydrogenation, and LC/MS analysis of the reaction mixture showed the disappearance of the peak corresponding to compound A (~2.5 min) and the appearance of a peak at 3.17 minutes with m/z 179.03839 (FIG. 17), corresponding to a formula of $C_6H_{11}O_4S^-$ (0.2 ppm off the calculated value of 179.03835). Product ion spectrum ($MS^2$) (FIG. 18) and $MS^3$ spectra (CID and HCD) of the m/z 131 ion (FIG. 19) support the identity of the saturated structure of compound A as shown in Scheme 6 for the rationalization of the fragments.

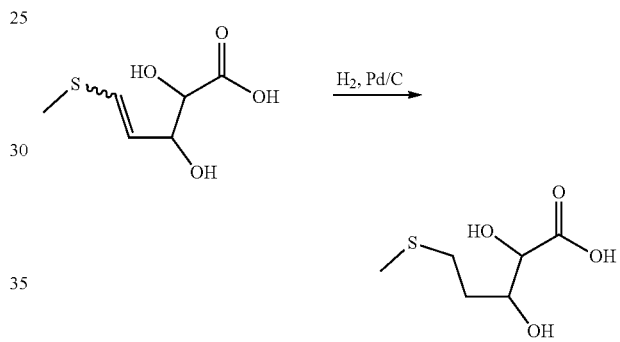

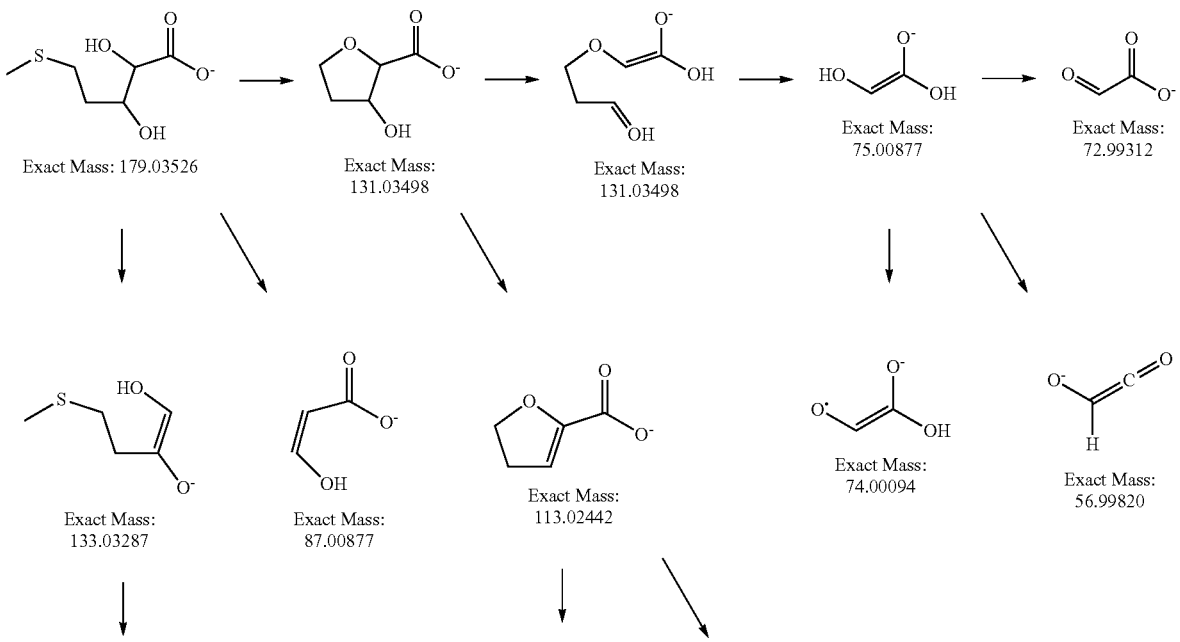

Scheme 6. Possible fragmentation pathways of hydrogenated analog.

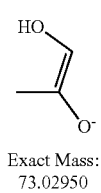

Exact Mass:
73.02950

-continued

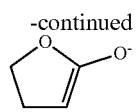

Exact Mass:
85.02950

Exact Mass:
69.03459

Figure 20:
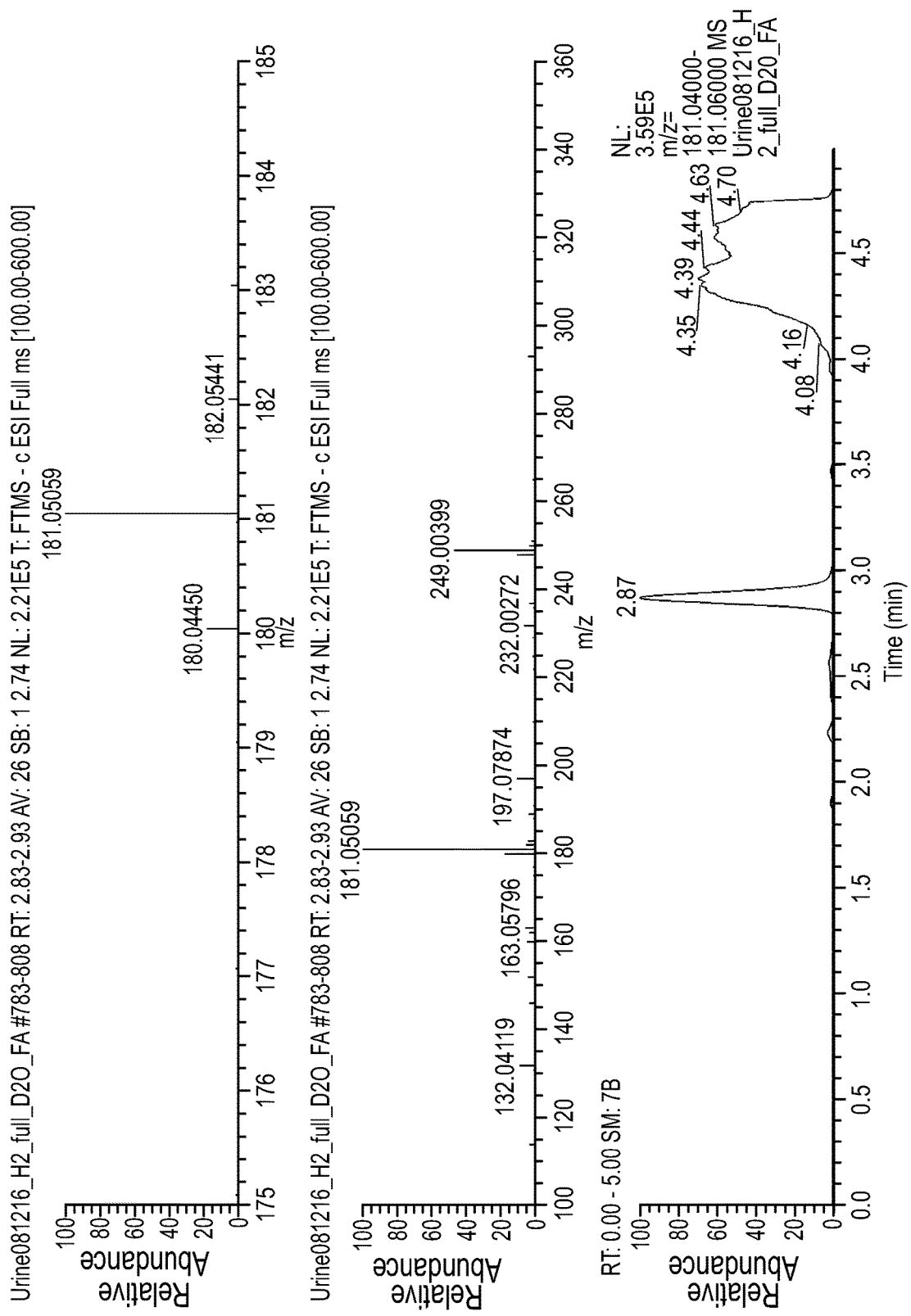
FIG. 20 shows LC/MS chromatogram and mass spectrum of the deuterated species of hydrogenated compound A in a urine sample.
Figure 21A:
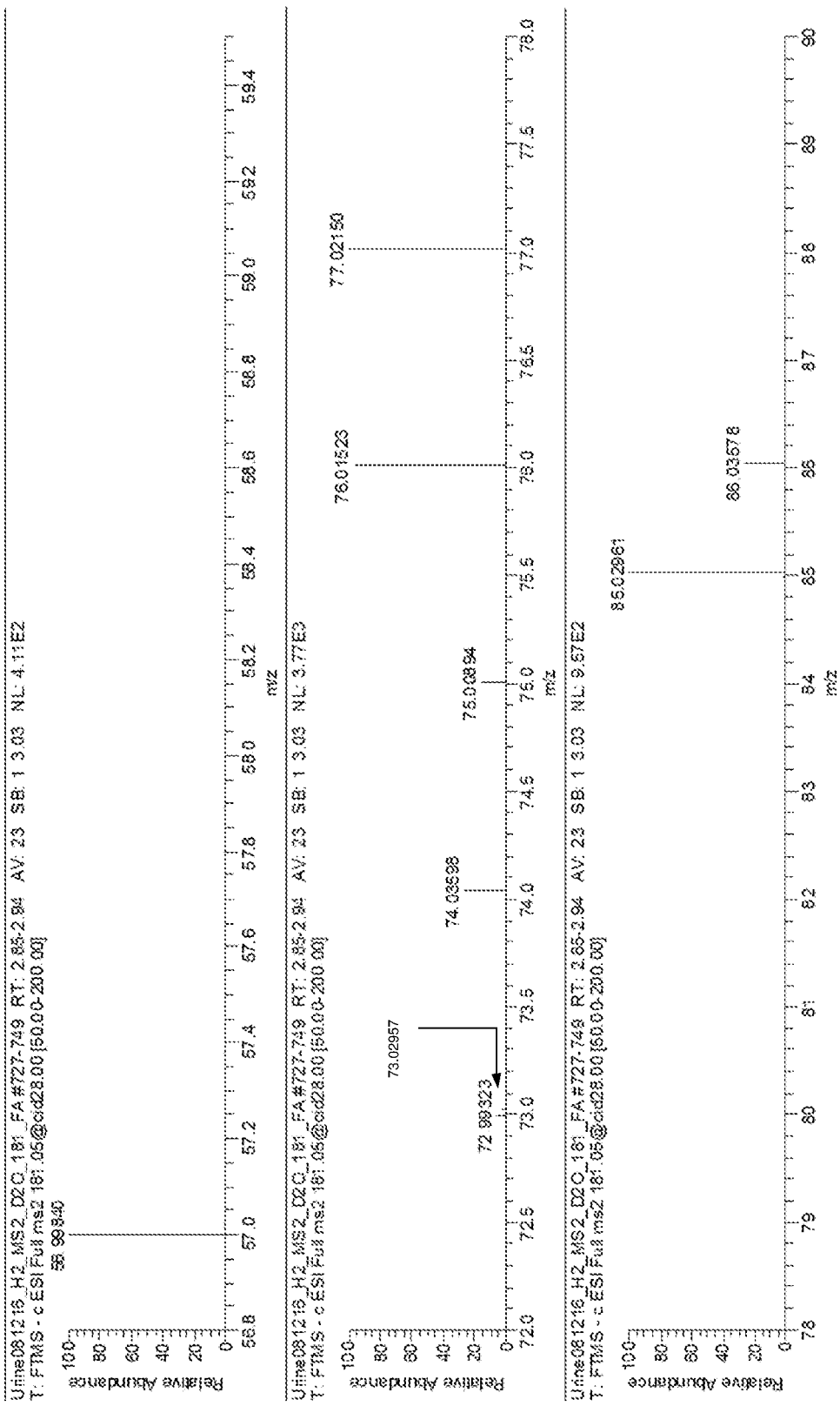
FIGS. 21A and 21B show product ion spectrum ($MS^2$) of the deuterated species of hydrogenated compound A with expansions using CID in a urine sample.
Figure 21B:
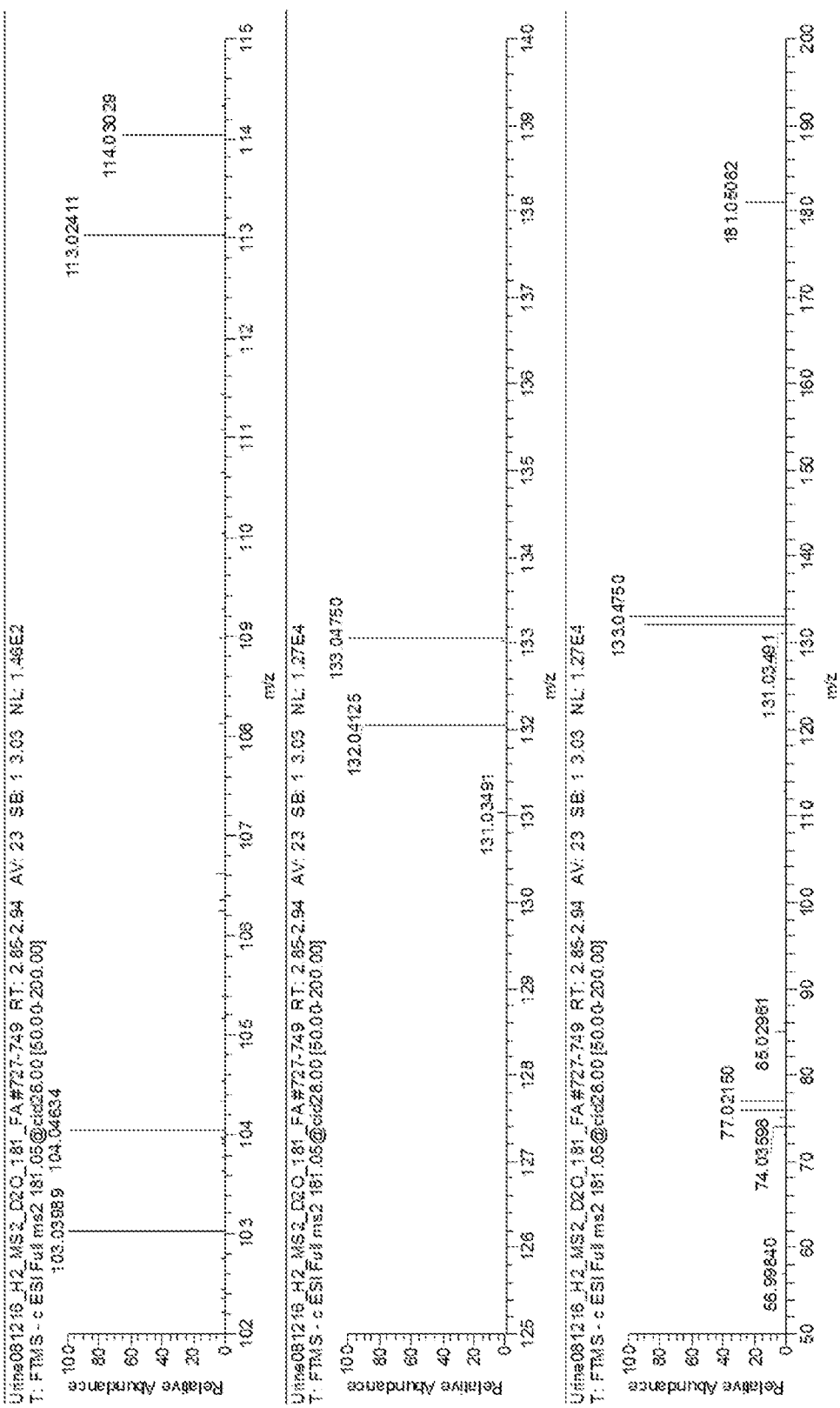
Figure 22:
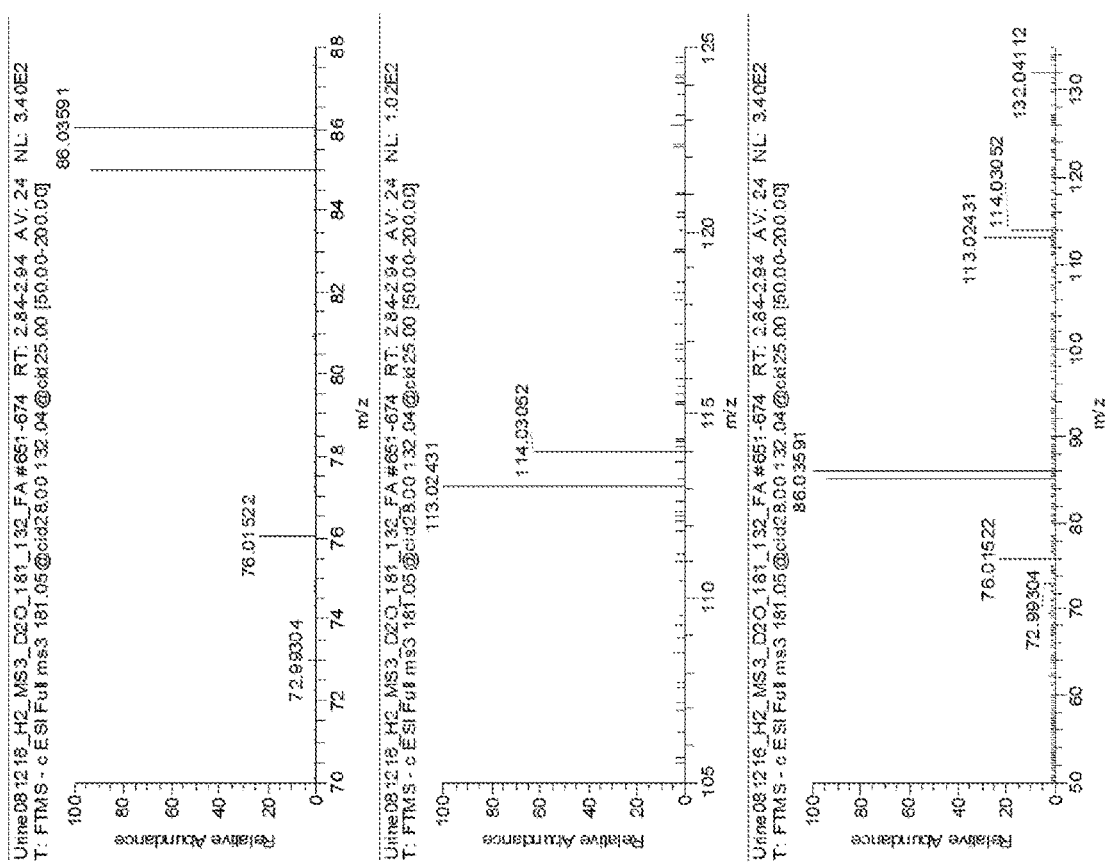
FIG. 22 shows $MS^3$ spectrum of m/z 132 of the deuterated species of hydrogenated compound A using CID in a urine sample.
Figure 23:
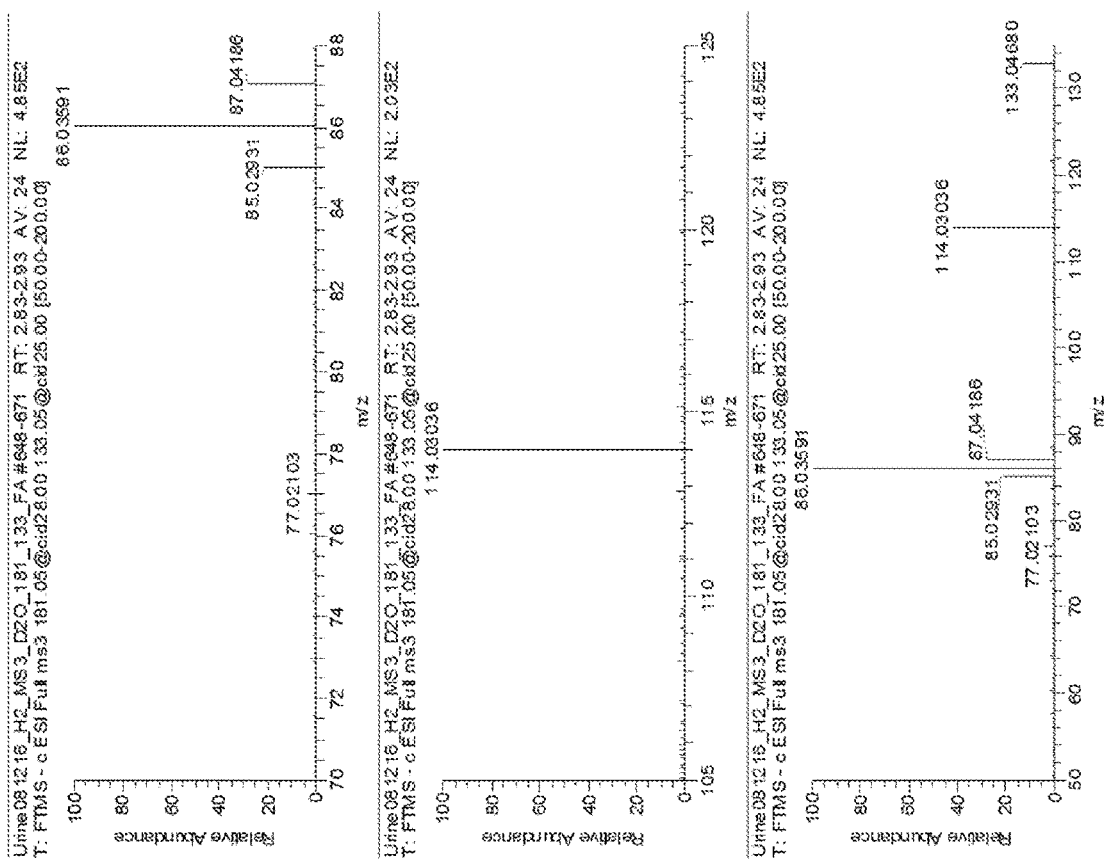
FIG. 23 shows MS³ spectrum of m/z 133 of the deuterated species of hydrogenated compound A using CID in a urine sample.

LC/MS analysis using deuterated mobile phase revealed that two deuterons were incorporated into the pseudo molecular ion with an m/z 181.05059 (FIG. 20), corresponding to a formula of $C_6H_9D_2O_4S^-$ (−1.77 ppm off the calculated value of 181.05191). Product ion spectrum (FIG. 21) and $MS^3$ spectra of the m/z 132 ion (FIG. 22) and the m/z 133 ion (FIG. 23) of the deuterated species are consistent with the expected saturation product. Possible fragmentation pathways are outlined in Scheme 7 for the deuterated species.

Scheme 7. Possible fragmentation pathways of the doubly deuterated species of hydrogenated analog.

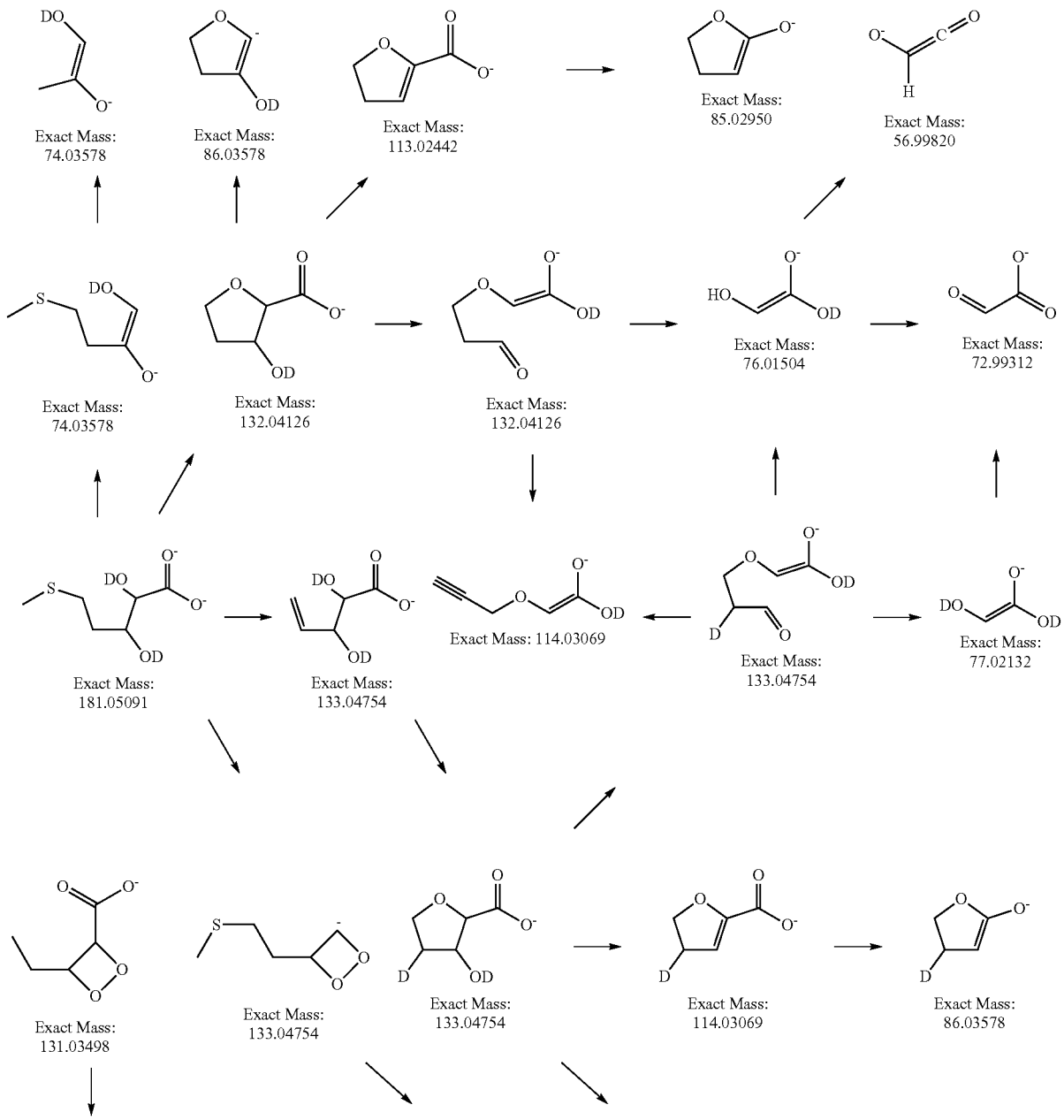

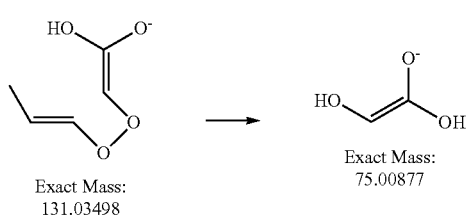

Exact Mass: 131.03498

Exact Mass: 75.00877

Exact Mass: 85.02950

Exact Mass: 87.04206

Figure 24:
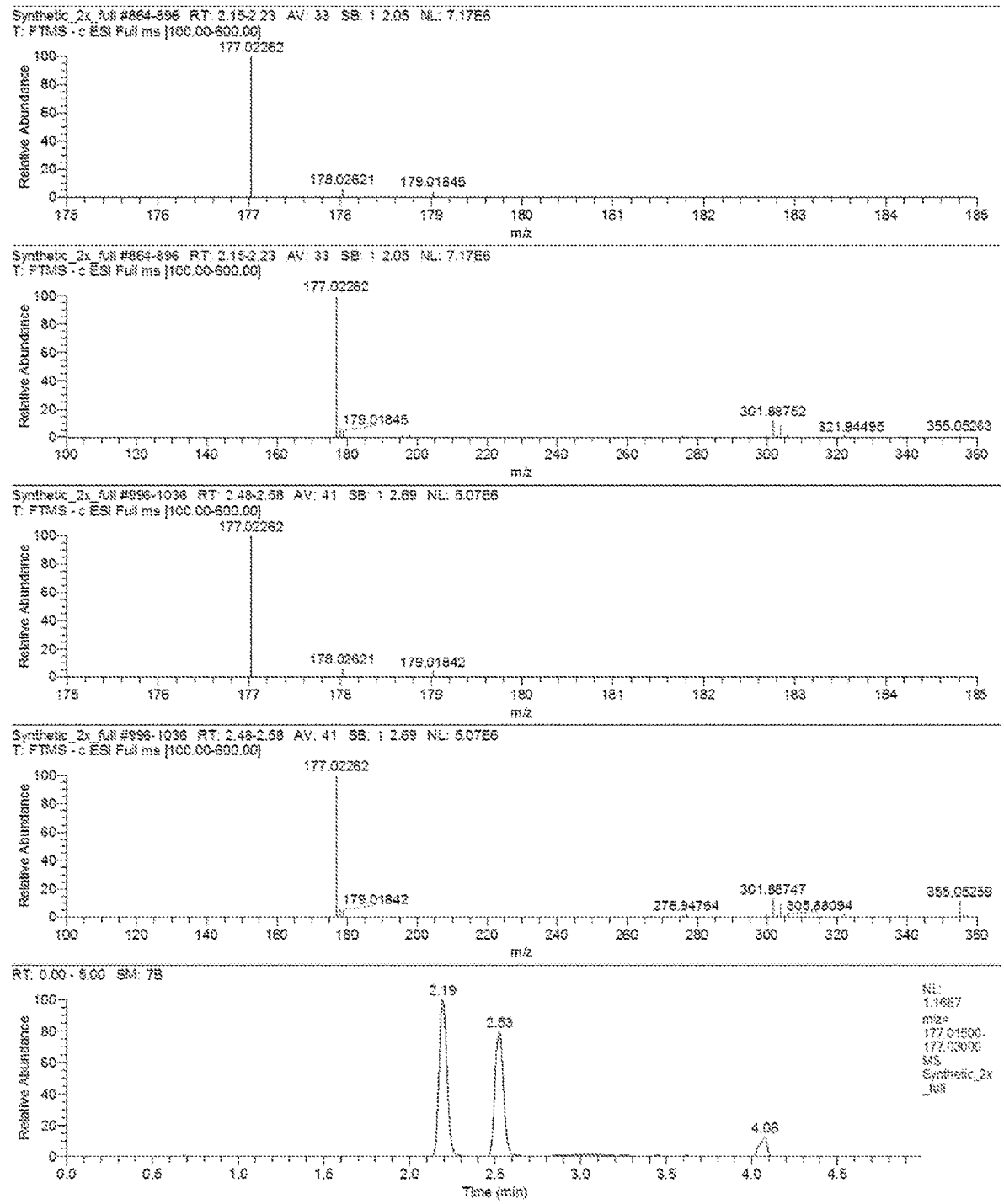
FIG. 24 shows LC/MS chromatograms and mass spectra of synthetic cis and trans DMTPAs.

The proposed structure was further confirmed by direct comparison to a synthetic standard (see Example 1). The synthetic cis and trans DMTPA mixture prepared by Example 2, Method 1 resulted in products at 2.19 and 2.53 minutes with a molecular ion of m/z 177.02262 (−0.5 ppm off calculated value), (FIG. 24) by LC/MS. The product prepared by Method 1 that elutes at 2.53 minutes (later determined to be trans DMTPA) was selected for further comparison to compound A.

Figure 25A:
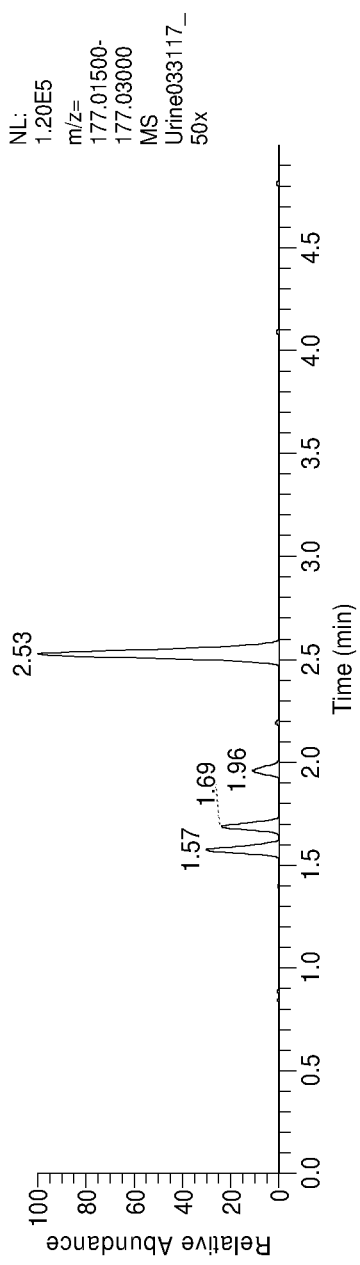
FIGS. 25A, 25B and 25C show LC-MS chromatograms for compound A (2.53 min) in urine sample (A), synthetic cis and trans DMTPAs, 2.20, and 2.53 min, respectively (B), and their co-injection (C).
Figure 25B:
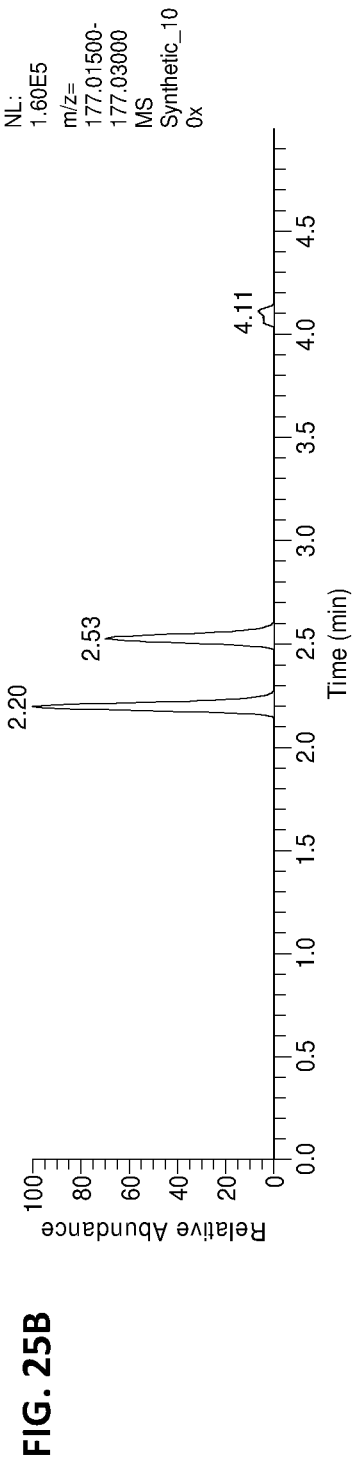
Figure 25C:
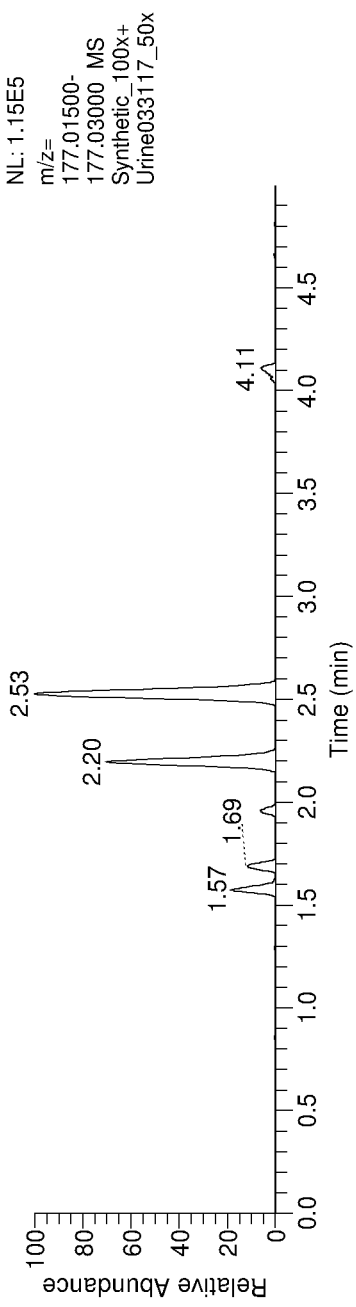
Figure 26A:
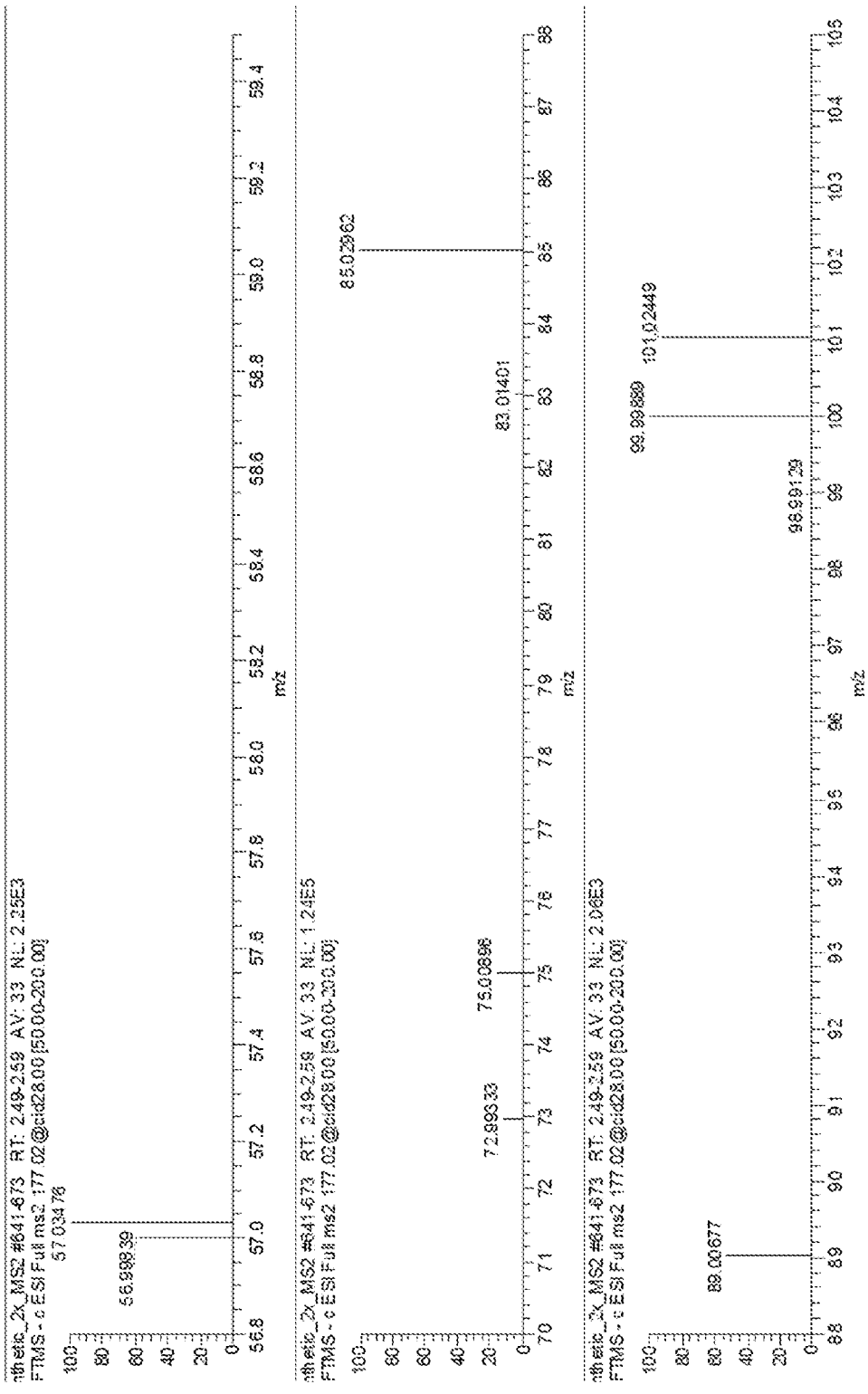
FIGS. 26A and 26B show product ion spectrum (MS²) of synthetic trans DMTPA with expansions using CID.
Figure 26B:
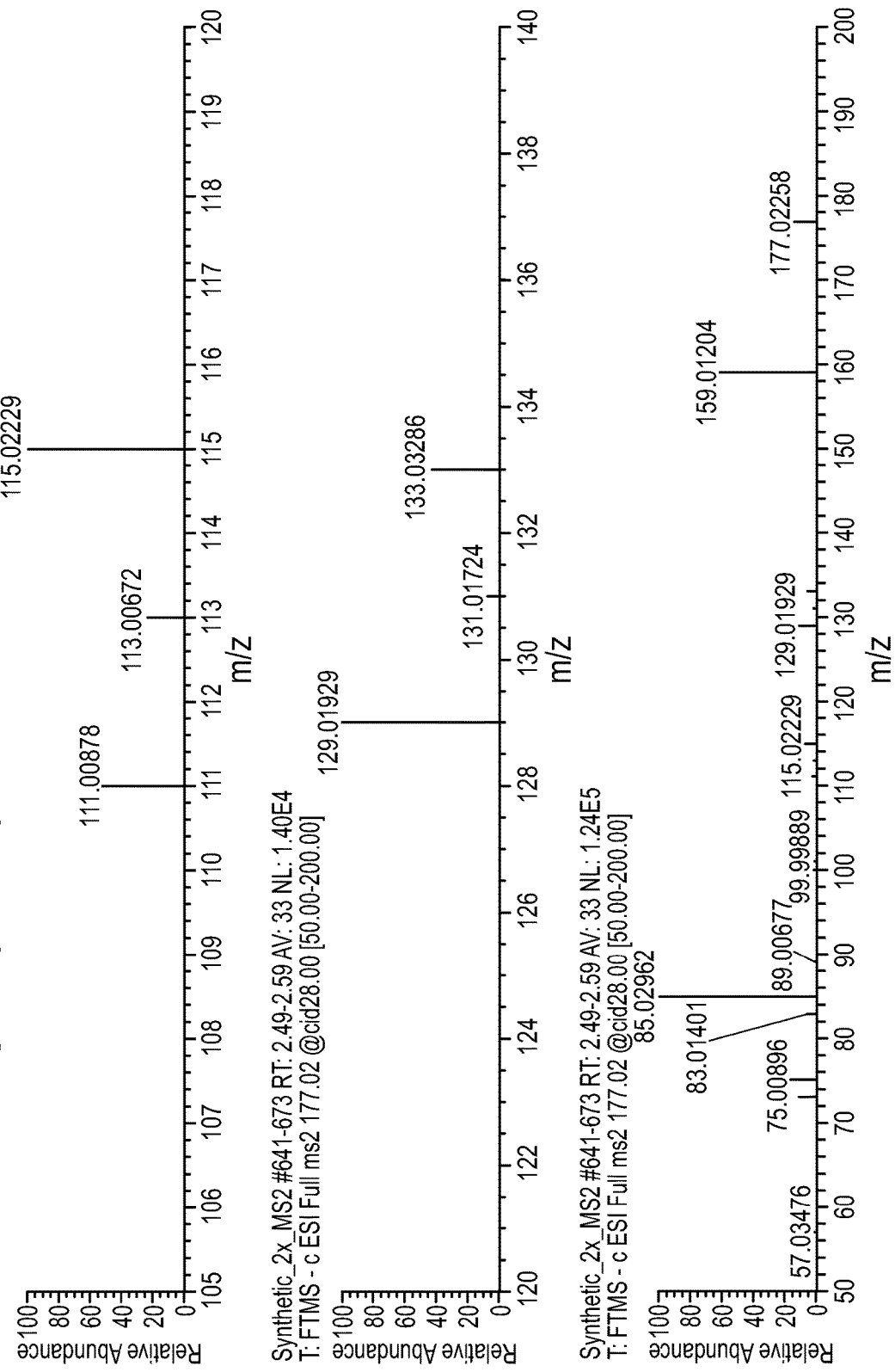
Figure 27A:
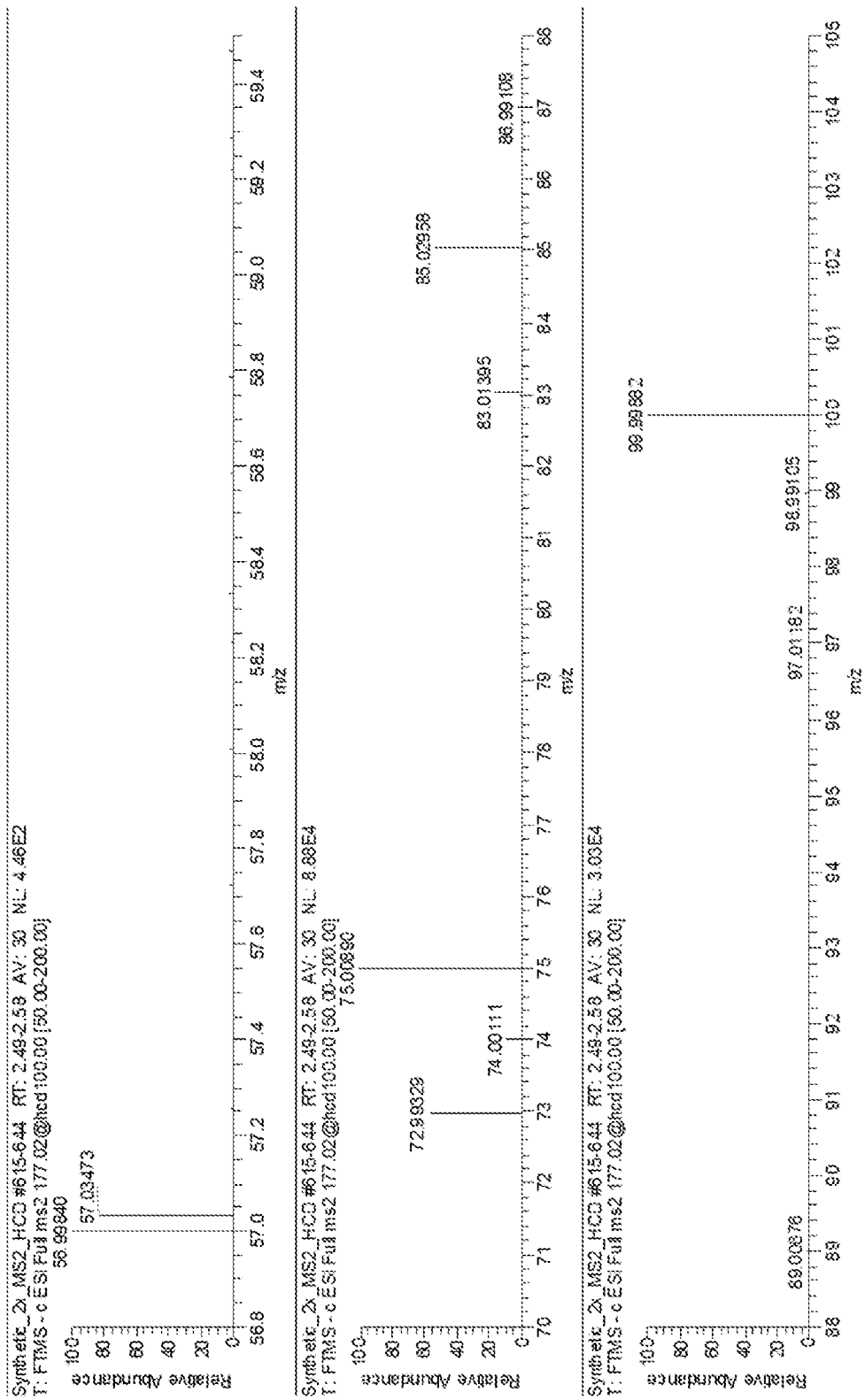
FIGS. 27A and 27B show product ion spectrum (MS²) of synthetic trans DMTPA with expansions using HCD.
Figure 27B:
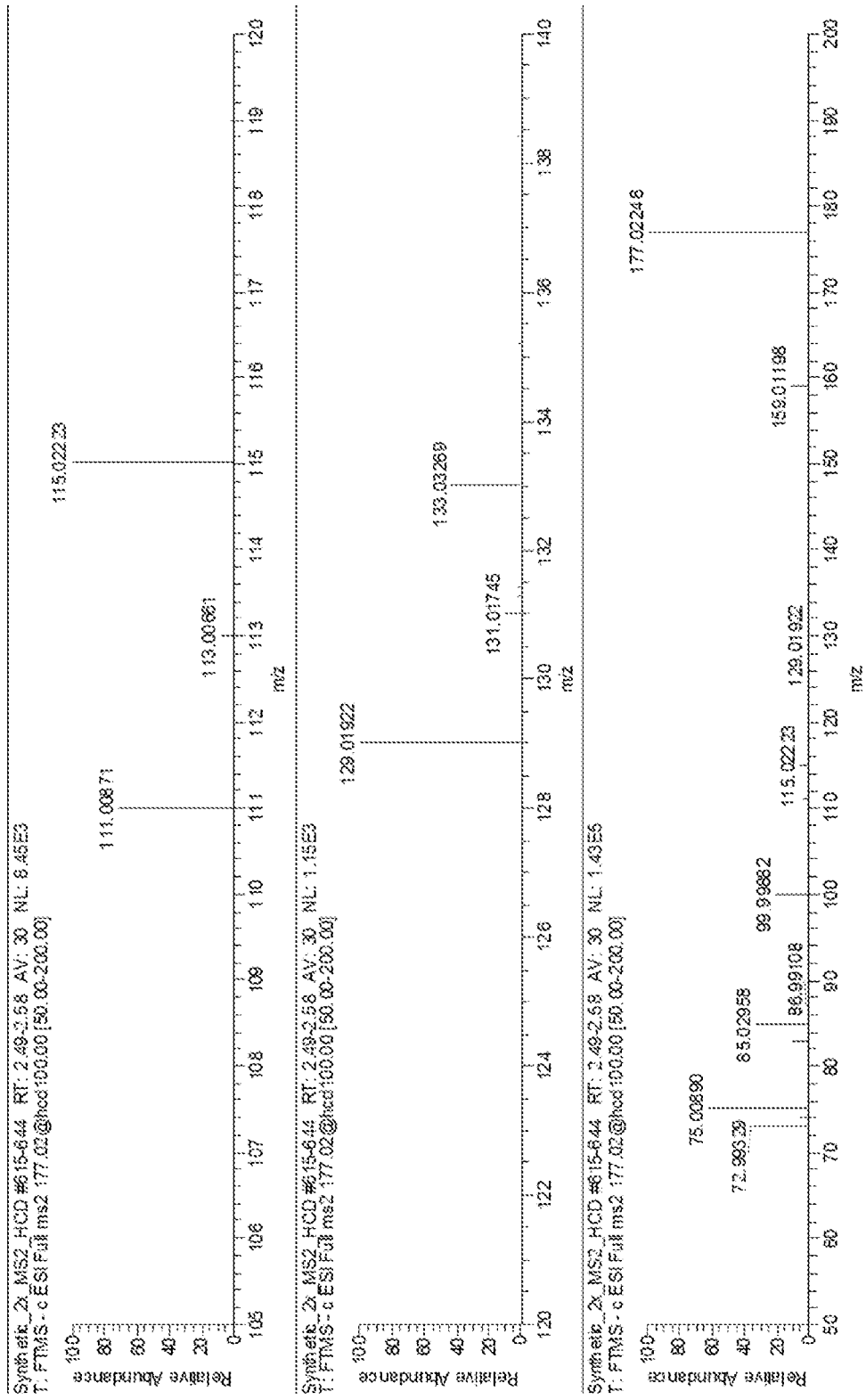
Figure 28A:
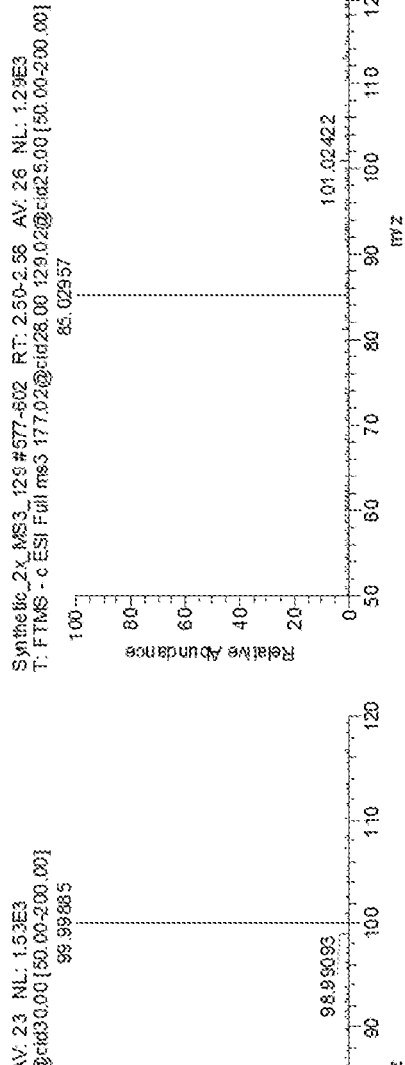
FIGS. 28A, 28B, 28C and 28D show MS³ spectra of m/z 115 (A), 129 (B), 159 (C), and 85 (D) of synthetic trans DMTPA using CID.
Figure 28B:
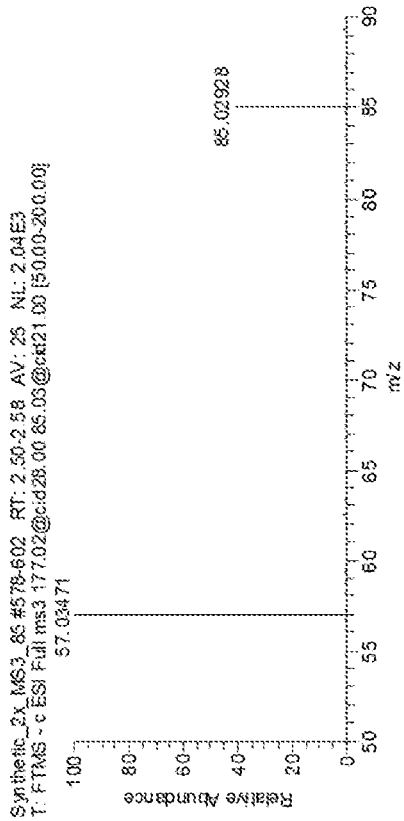
Figure 28C:
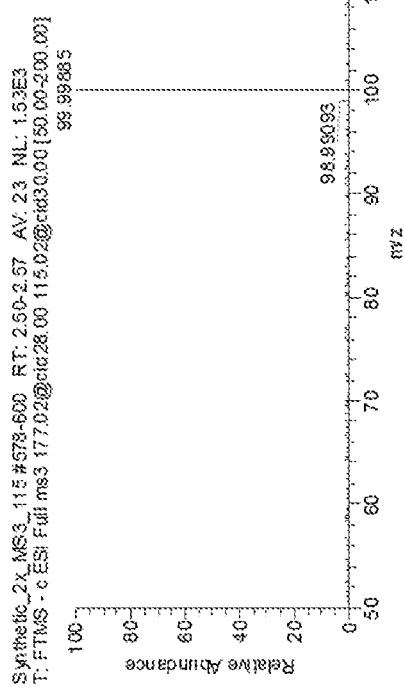
Figure 28D:
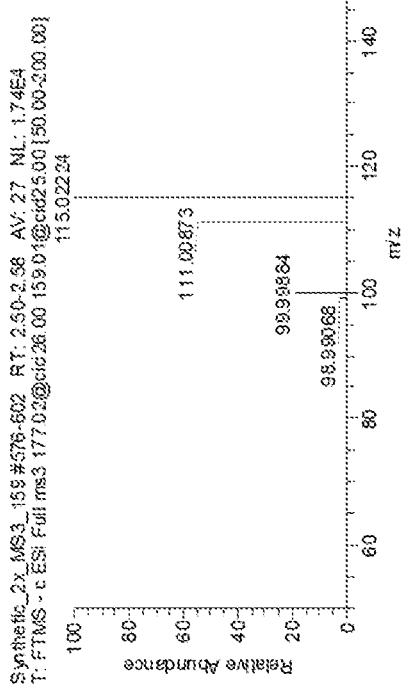
Figure 29A:
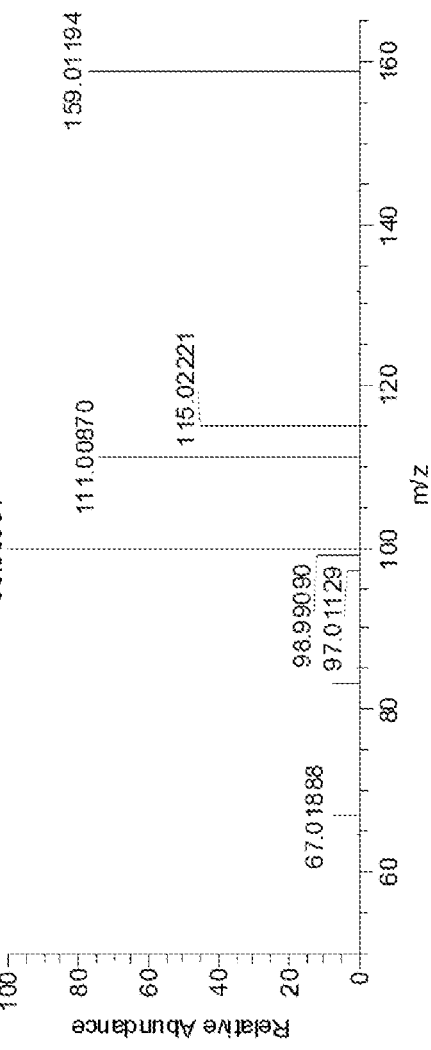
FIGS. 29A and 29B show MS³ spectra of m/z 159 (A) and 85 (B) of synthetic trans DMTPA using HCD.
Figure 29B:
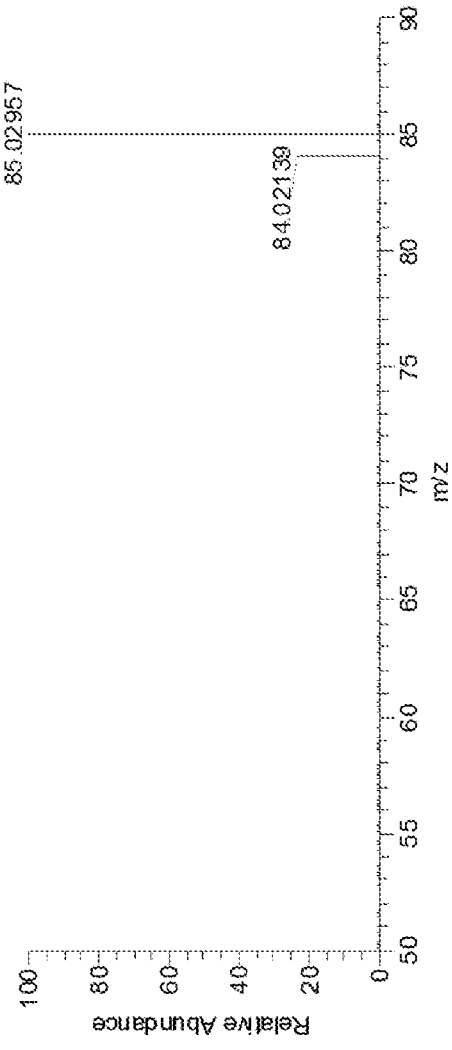
Figures 30A, 30B:
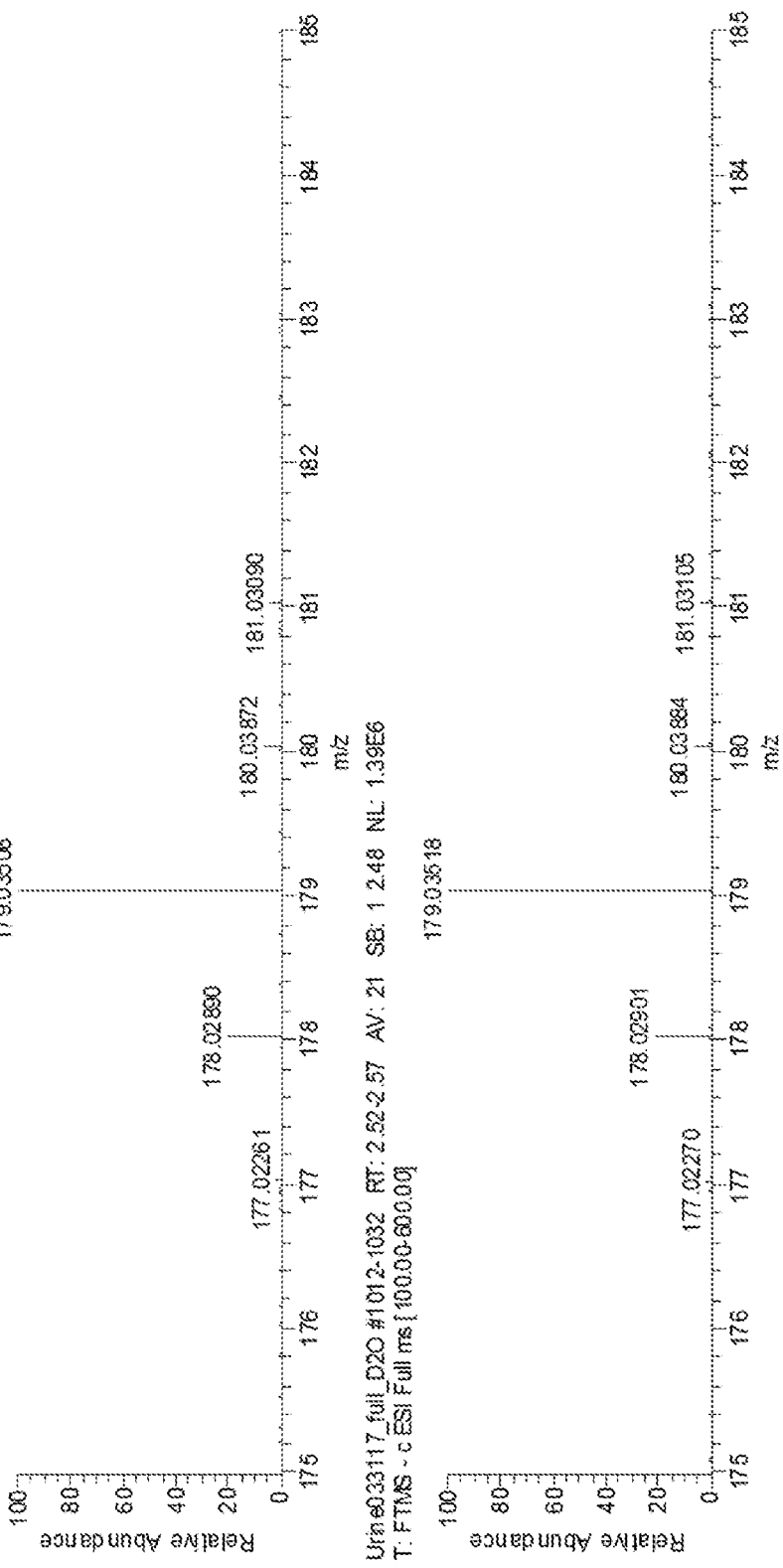
FIGS. 30A and 30B show full scan mass spectra of the deuterated species of synthetic trans DMTPA (A) and the deuterated species compound A in a urine sample (B).
Figure 31A:
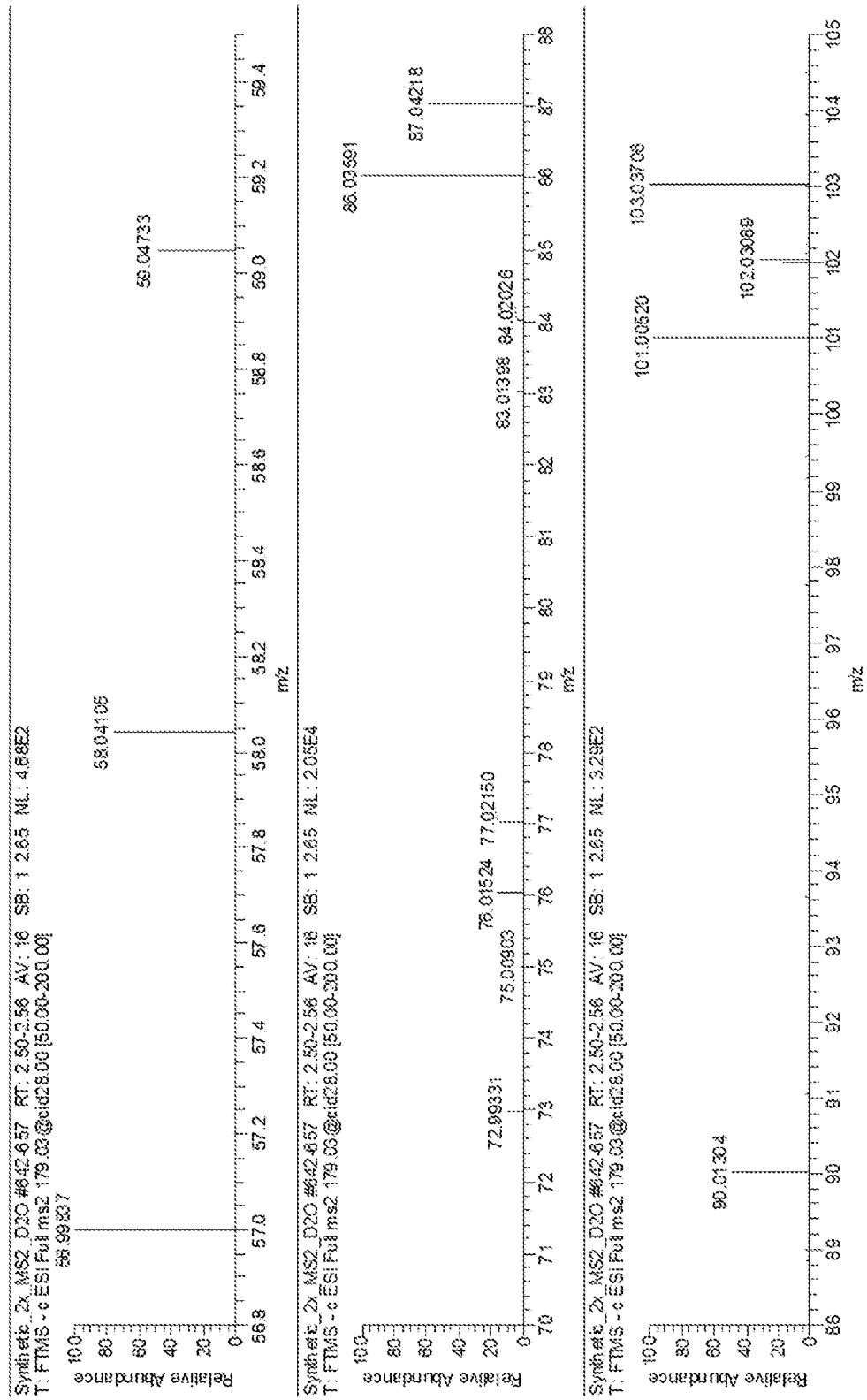
FIGS. 31A and 31B show product ion spectrum (MS²) of deuterated synthetic trans DMTPA with expansions using CID.
Figure 31B:
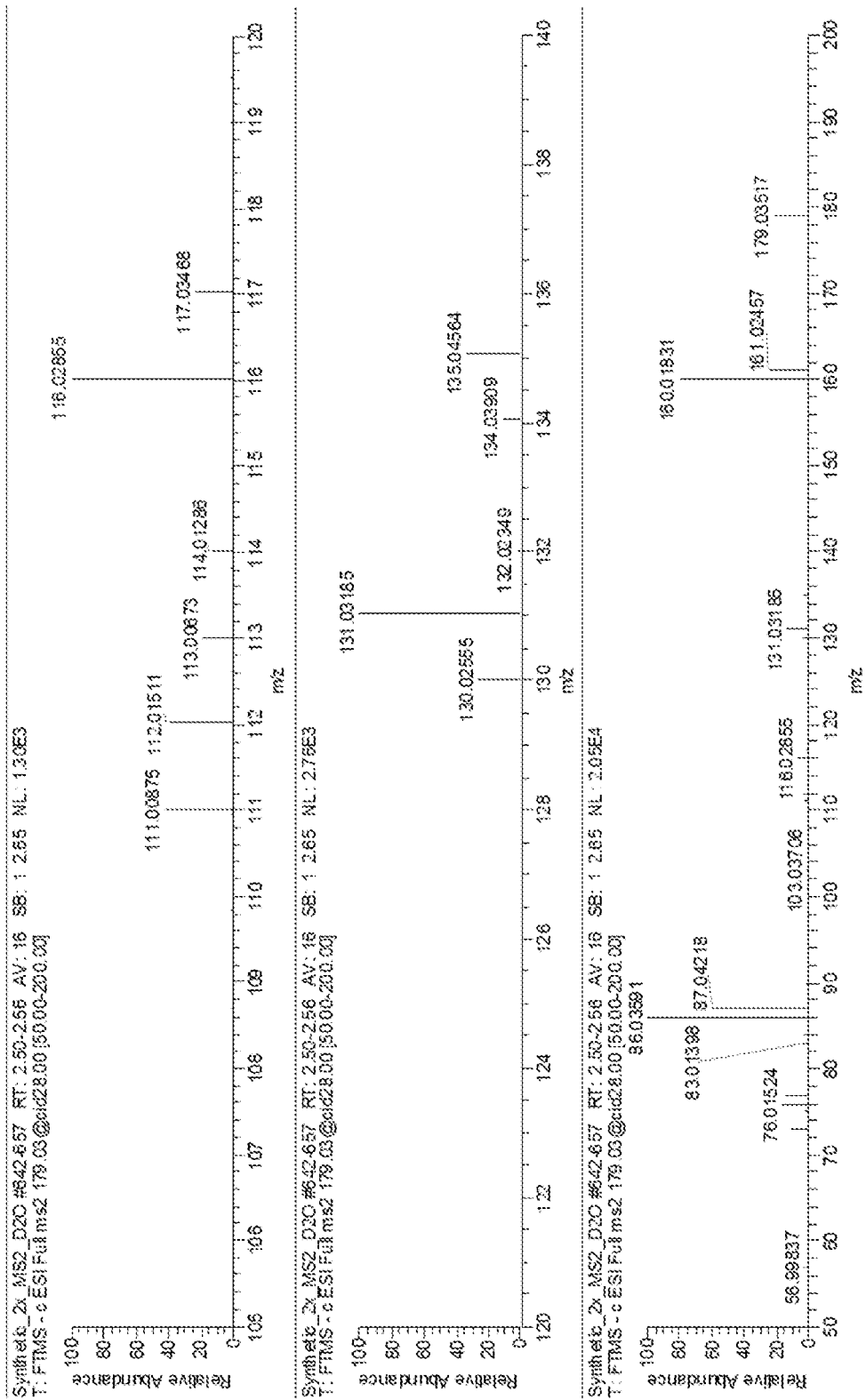
Figure 32:
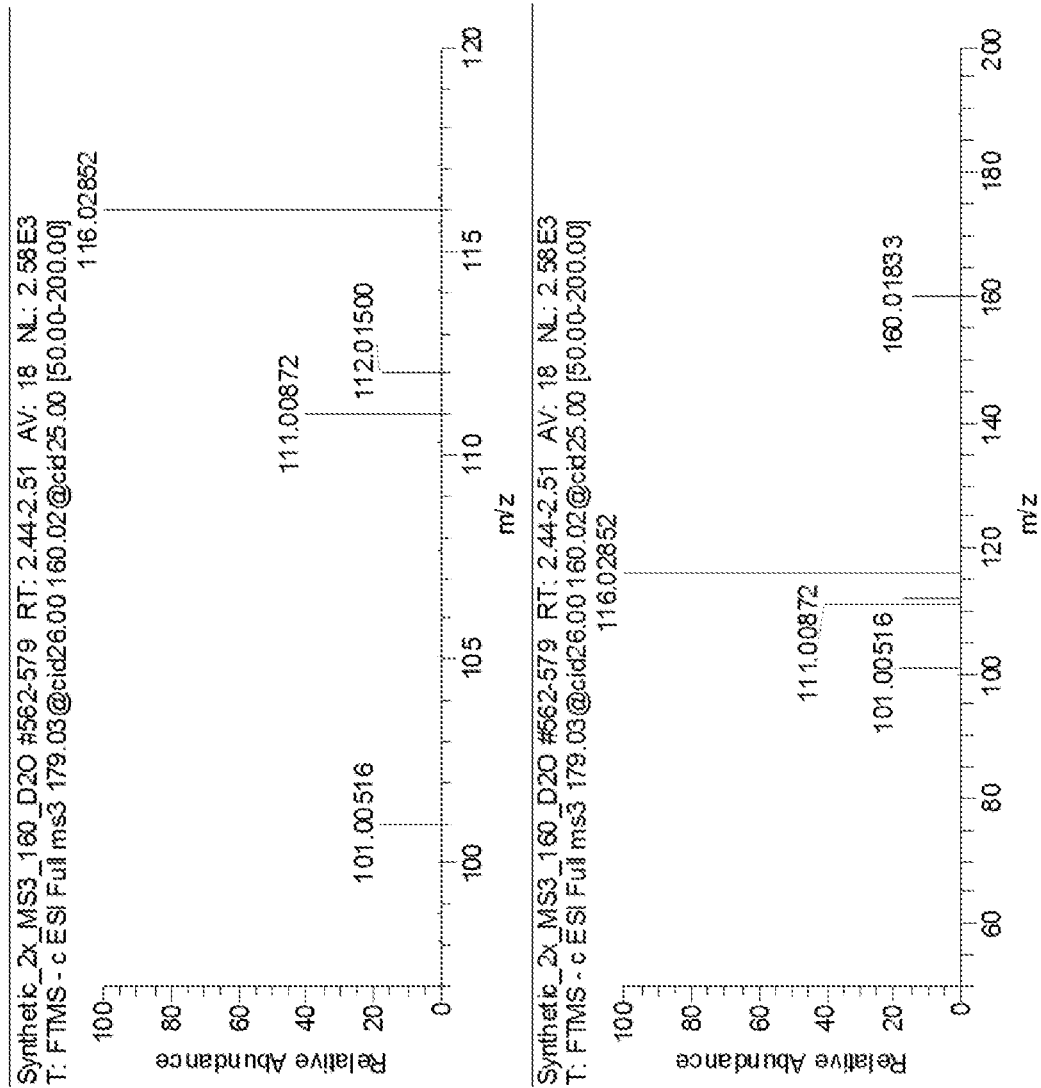
FIG. 32 shows MS³ spectrum of m/z 160 of deuterated synthetic trans DMTPA with expansions using CID.
Figure 33:
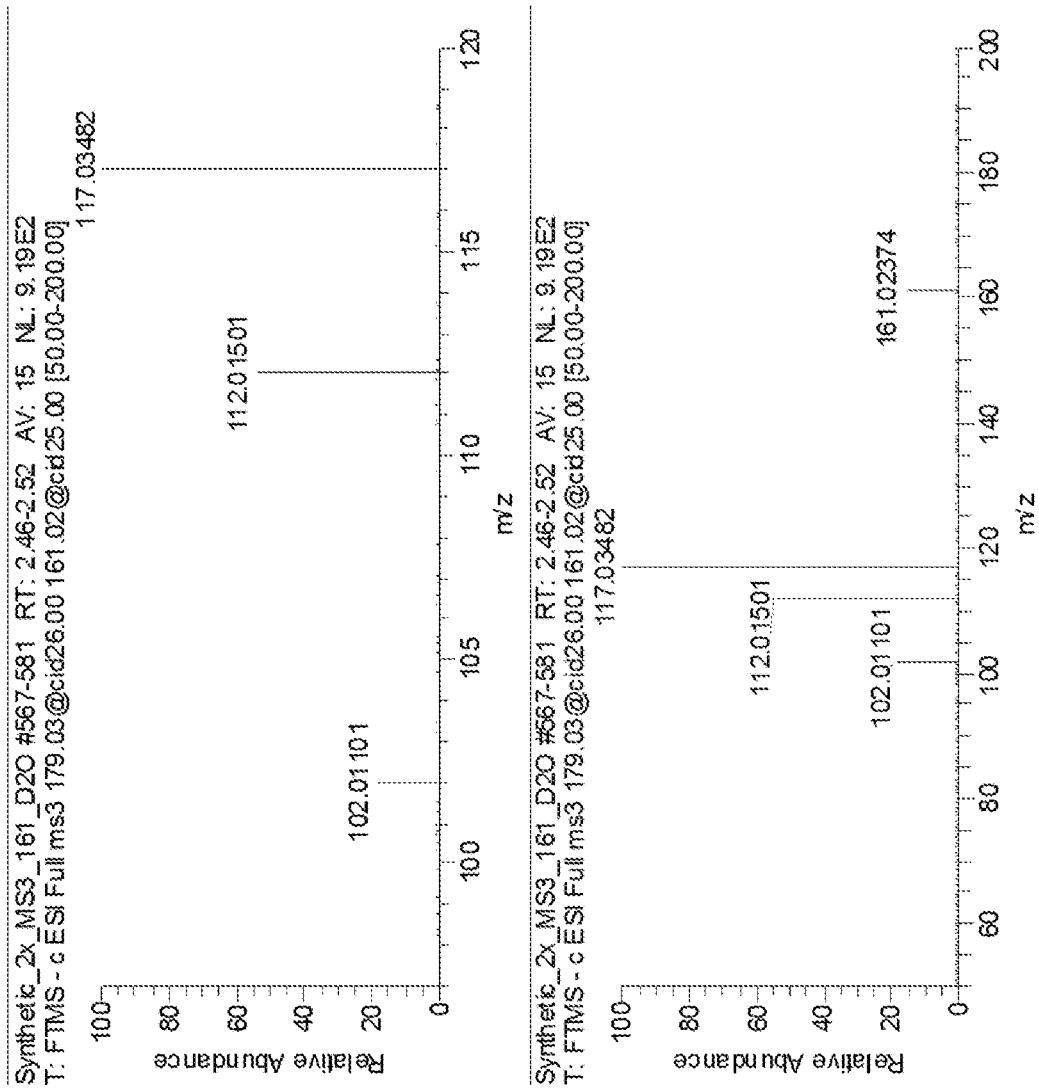
FIG. 33 shows MS³ spectrum of m/z 161 of deuterated synthetic trans DMTPA with expansions using CID.

The retention time of the synthetic trans DMTPA (FIG. 25B) matched that of compound A in urine (FIG. 25A) as they co-eluted (FIG. 25C) under the chromatographic conditions. Product ion spectrum (MS$^2$) of synthetic trans DMTPA by CID (FIG. 26) and HCD (FIG. 27) matched those compound A (FIGS. 4 and 5) by fragmentation patterns and intensity distributions. Further fragmentation by CID of the 115, 129, 159, and 85 daughter ions of synthetic trans DMTPA produced MS$^3$ spectra (FIG. 28A-D). MS$^3$ spectra of the 159 and 85 daughter ions were also produced by HCD (FIG. 29A-B). Resulting MS$^3$ spectra of synthetic trans DMTPA were essentially identical to those from compound A (FIG. 6). Furthermore, the synthetic trans DMTPA was analyzed after deuterium exchange and the resulting MS, MS$^2$, and MS$^3$ spectra also matched those of compound A very well as shown in FIGS. 30-33 as compared to FIGS. 13-15. All of these chromatographic and MS spectral data strongly support that compound A is trans DMTPA.

Example 2. Synthesis of (2R,3R)-2,3-dihydroxy-5-methylthio-trans-4-pentenoic Acid (Trans DMTPA)

Method 1.
Wittig Reaction (Methylthiomethyl)triphenylphosphonium chloride (500 mg, 1.39 mmole, 2.2 equiv.) was suspended in tetrahydrofuran under an argon atmosphere in a 25 mL round bottom flask. The mixture was cooled to 0° C. and sodium bis(trimethylsilyl)amide (1.0 M in tetrahydrofuran, 1.39 mL, 1.39 mmole, 2.2 equiv.) was slowly added while the mixture was stirring. The resulting mixture was stirred for an additional 30 min at 0° C. and 2,3-cyclohexylidene-L-erythruronic acid (136 mg in 1.0 mL of tetrahydrofuran, 0.633 mmole, 1.0 equiv.) was slowly added. After 5 min, the reaction mixture was allowed to warm to room temperature and stirred overnight. The reaction mixture was transferred to aqueous NaH$_2$PO$_4$ (1.0 M, 25 mL), and the resulting mixture (pH ~6.0) was extracted with ethyl acetate (2×40 mL). The combined organic extract was dried (MgSO$_4$), filtered, and evaporated to dryness to give a thick oil (402 mg). This crude extract was chromatographed on a silica gel column (2.5×18 cm), eluting with ethyl acetate/methanol (9:1). The corresponding fractions were pooled and concentrated to dryness to yield a mixture of E/Z (~5:4) isomers of protected thioenolethers as a brownish wax-like material (75 mg, 46%). $^1$H NMR (500 MHz, CD$_3$OD) δ 6.57 (1H, dd, J=14.9, 0.8 Hz, H-5 E), 6.37 (0.6H, dd, J=9.7, 1.0 Hz, H-5 Z), 5.49 (0.6H, dd, J=9.6, 8.7 Hz, H-4, Z), 5.26 (1H, dd, J=14.9, 8.0 Hz, H-4, E), 5.23 (0.8H, ddd, J=8.7, 7.2, 1.0 Hz, H-3, Z), 4.95 (1H, overlap DOH, ddd, J=8.3, 7.3, 1.0 Hz, H-3, E), 4.67 (1H, d, J=7.3 Hz, H-2, E), 4.66 (0.9H, d, J=7.3 Hz, H-2, Z), 2.32 (2H, s, CH$_3$), 2.26 (3H, s, CH$_3$), 1.35-1.95 (m, ring protons). $^{13}$C NMR (125 MHz, CD$_3$OD) δ 173.2, 173.1, 135.1, 132.6, 123.8, 119.9, 112.7, 112.5, 79.5, 78.4, 77.8, 75.6, 37.9, 36.01, 35.96, 26.4, 25.2, 25.0, 17.4, 14.3.

Figure 34:
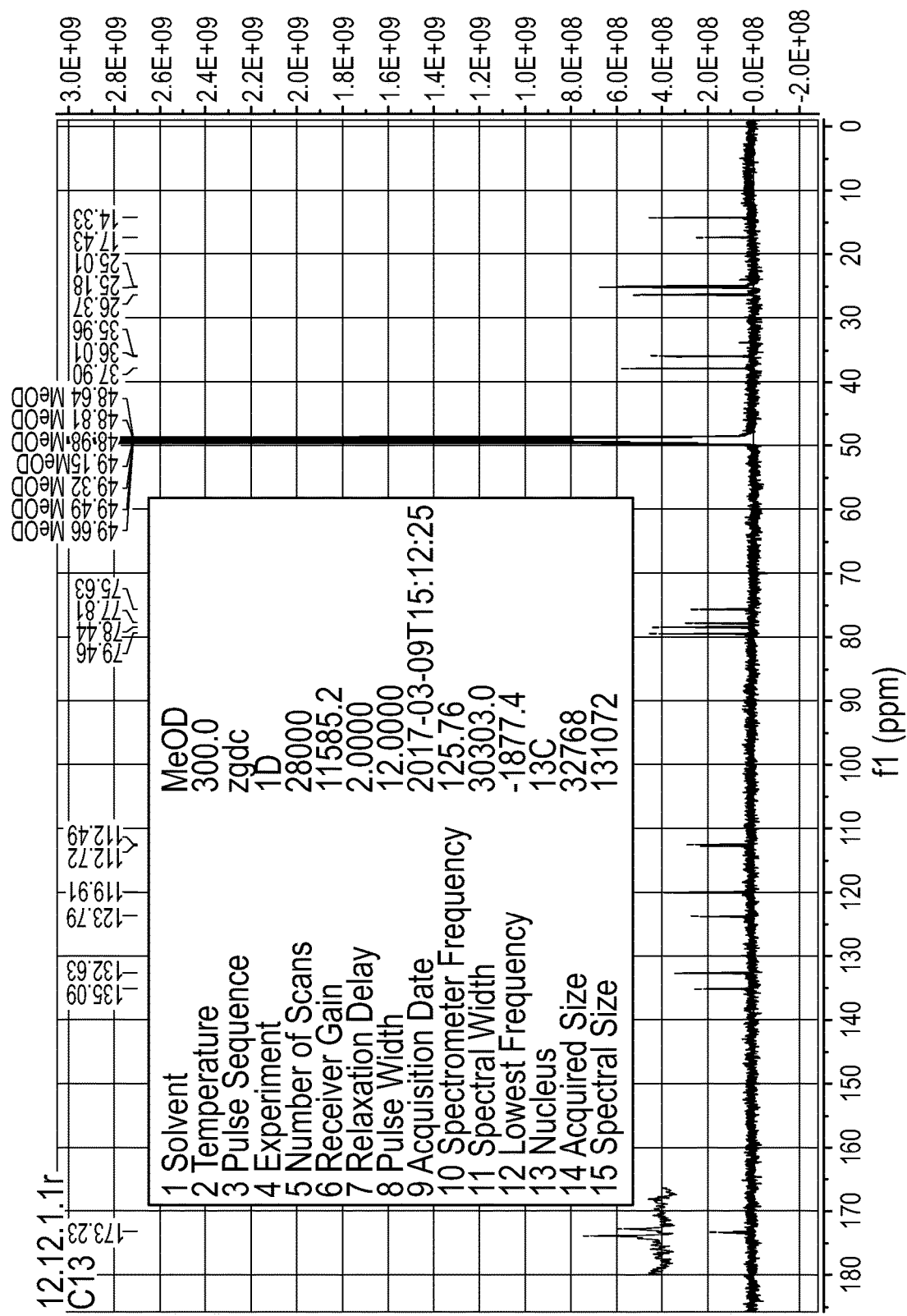
FIG. 34 shows a ¹³C NMR spectrum of purified Wittig reaction products (mixture of protected cis and trans thioenolethers).
Figure 35:
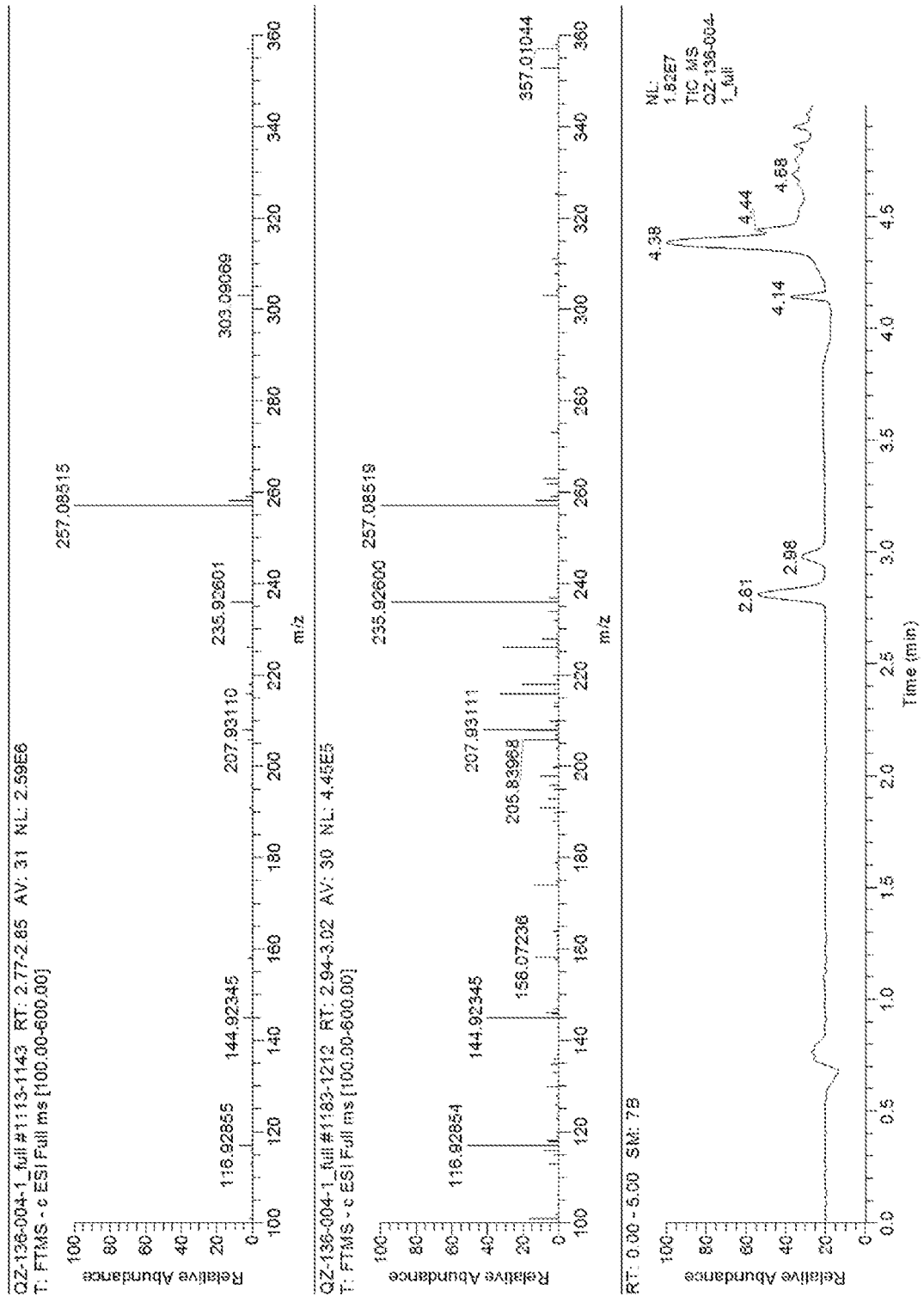
FIG. 35 shows LC/MS chromatogram and mass spectra of purified Wittig reaction products (mixture of protected cis and trans thioenolethers).
Figure 36:
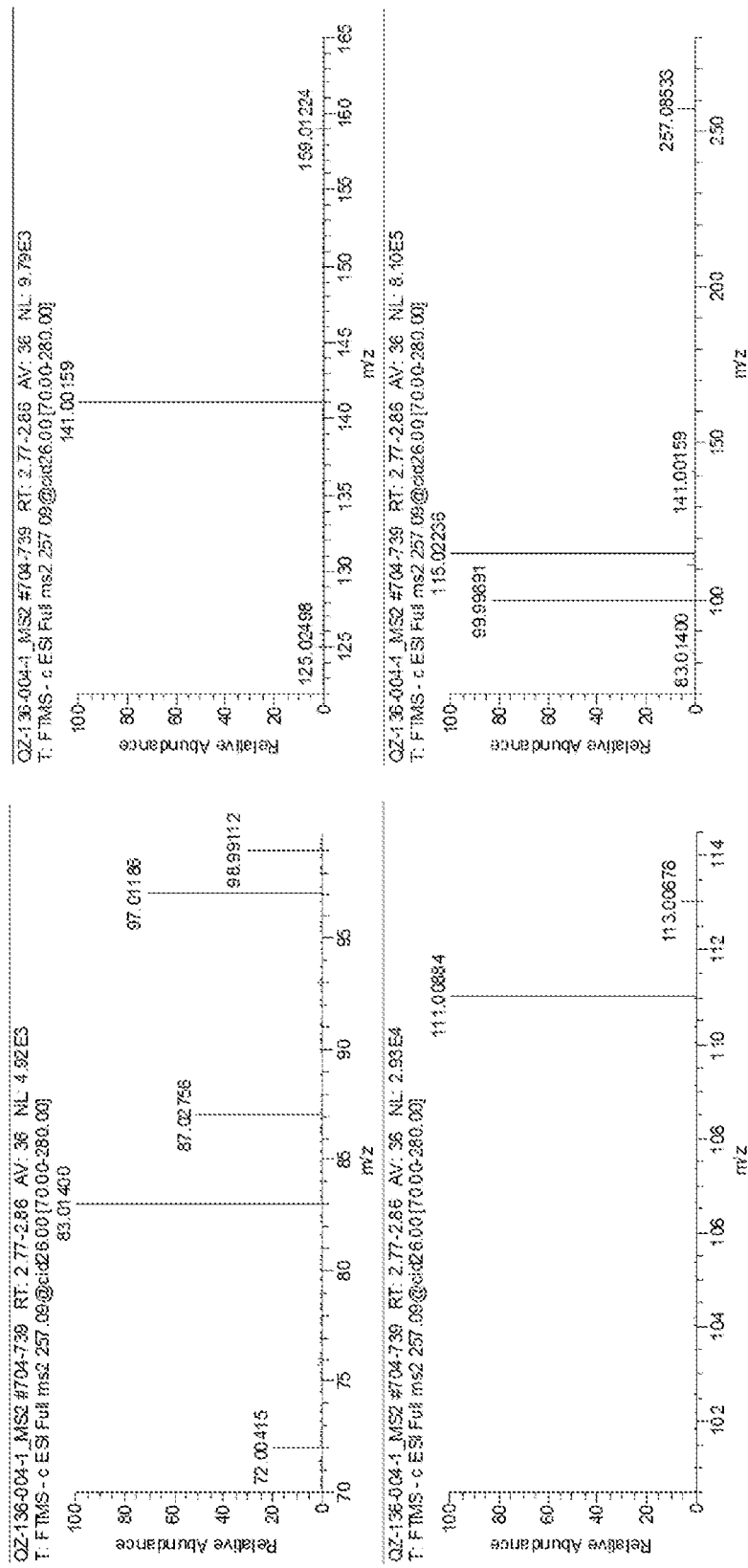
FIG. 36 shows product ion spectrum (MS²) of purified Wittig reaction products (RT of 2.81 min) with expansions using CID.
Figure 37:
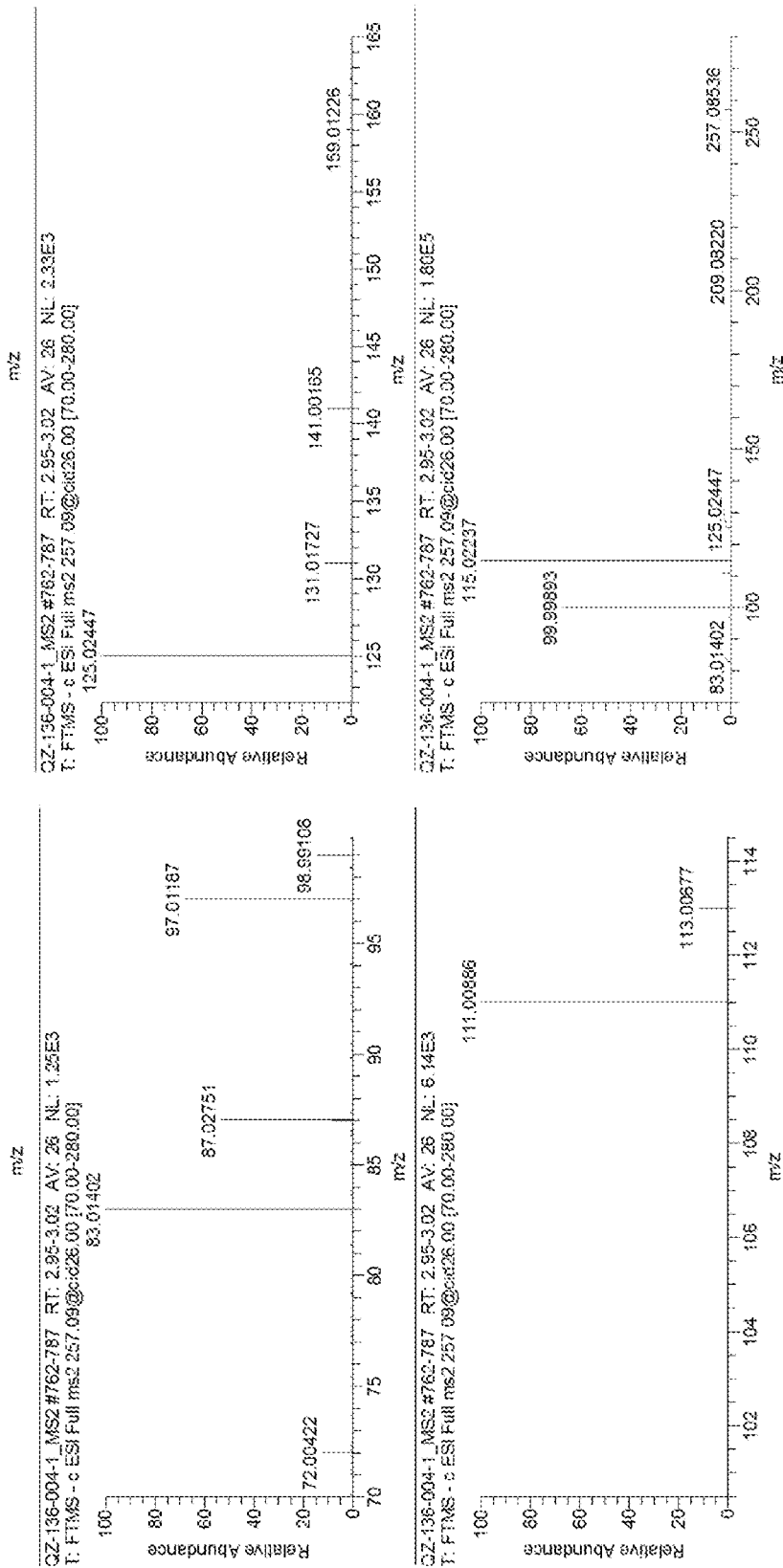
FIG. 37 shows product ion spectrum (MS²) of purified Wittig reaction products (RT of 2.98 min) with expansions using CID.

The structures were characterized by $^1$H, $^{13}$C, and $^1$H-$^1$H COSY NMR spectroscopic and mass spectrometric analyses. A $^{13}$C NMR spectrum of purified Wittig reaction products (a mixture of protected cis and trans thioenolethers) is shown in FIG. 34. LC/MS chromagotrams and mass spectrum of purified Wittig reaction products are shown in FIG. 35. Product ion spectrum (MS$^2$) of purified Wittig reaction products with RT of 2.81 min or 2.98 min are shown in FIGS. 36 and 37, respectively.

Deprotection

In a 20 mL Scintillation vial, the mixture of protected cis and trans thioenolethers (2.0 mg in 0.50 mL of acetonitrile), Dowex® 50WX8 (0.75 g, washed with water (2×10 mL)), water (4.5 mL), and a stir bar were added. After stirring at room temperature for 20 min, the mixture was transferred to 1.5 mL Eppendorf tubes and centrifuged for 5 min at 14,000 rpm. The combined supernatant was adjusted to pH ~7 with diluted ammonium hydroxide (4% of concentrated ammonium hydroxide in water). An aliquot was diluted with water and analyzed by LC/MS.

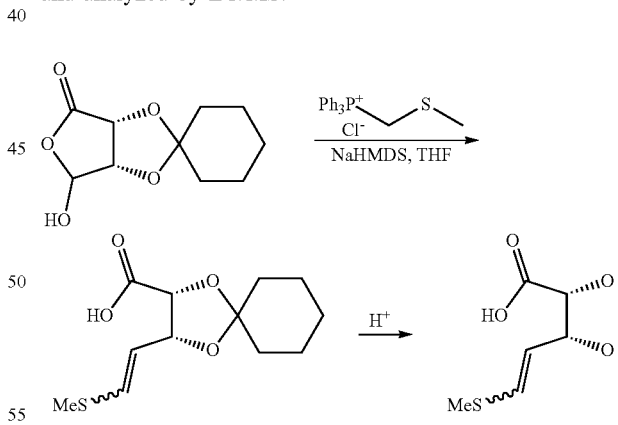

A second method for deprotection was carried out by dissolving the starting material in 0.1% aqueous formic acid. The solution was kept at room temperature for 1 h before LC/MS analysis.

HPLC Purification of Wittig Reaction Products (Mixture of Protected Cis and Trans Thioenolethers)

An Agilent 1290 Infinity UHPLC system, equipped with a binary solvent pump unit, a refrigerated autosampler (set at 4° C.), and a column heater (set at 50° C.) was used for semi-preparative liquid chromatography with a reversed phase column (Waters XBridge® C18, 3.5 µm, 4.6×150 mm). Mobile phase A was water/acetonitrile (92:8) and mobile phase B was acetonitrile. Linear gradient elution was carried out with an initial condition of 100% mobile phase A, which was maintained for 10 min. Mobile phase B was increased to 90% in 1.0 min and maintained for 2.0 min. Mobile phase B reverted to 0% in 0.5 min and maintained for 2.5 min for equilibration for next injection. The flow rate was 900 µL/min for a total run time of 16 min. The eluent was directly introduced into the electrospray source of an AB Sciex QTrap 5500 mass spectrometer. Isopropanol was used for needle wash. The mass spectrometer was operated in negative multiple reaction monitoring (MRM) mode. Ionspray voltage was set at −4.3 kV, source temperature at 550° C., curtain gas at 30, and nebulizer and desolvation gas flow rates at 70, CAD gas at medium. Two transitions (257.1/115.0 and 257.1/100.0) were monitored with declustering potential at −60 V, entrance potential at −10 V, collision energy at −10 eV (detuned), and collision cell exit potential at −12 V. The eluent between 7.0 and 9.8 min (for the early eluting peak) from about 400 runs was diverted to a collection flask automatically using the switch valve on the mass spectrometer. The collected fraction was dried under a gentle stream of nitrogen at room temperature over two weeks. The residue was dissolved in methanol and the solution was transferred to a small vial. After removal of solvent, the residue was analyzed by NMR and MS. Results for the sulfoxides are: $^1$H NMR (700 MHz, CD$_3$OD) δ 6.37 (1H, d, J=14.9 Hz, H-5), 5.40 (1H, dd, J=15.0, 7.9 Hz, H-4), 4.77 (1H, dd, J=7.9, 7.0 Hz, H-3), 4.57 (1H, d, J=7.0 Hz, H-2), 2.67 (1H, s, CH$_3$), 2.22 (2H, s, CH$_3$), 1.25-1.90 (10H, m, ring protons). For the isomer eluting at 2.42 min, HRESIMS m/z 273.08049 [M-H]$^-$ (calcd for C$_{12}$H$_{17}$O$_5$S$^-$, 273.08022). MS$^2$ m/z 258.05700, 156.99666, 131.01737, 123.00895, 115.99388, 113.00681, 111.00892, 98.99116, 97.98334. For the isomer eluting at 2.53 min, HRESIMS m/z 273.08046 [M-H]$^-$ (calcd for C$_{12}$H$_{17}$O$_5$S$^-$, 273.08022). MS$^2$ m/z 258.05702, 156.99670, 131.01738, 123.00888, 115.99389, 113.00683, 111.00894, 98.99114, 97.98335.
Method 2.

A general strategy for a second synthetic approach is represented below. Protected L-erythruronic acid may be used as the starting molecule. Any suitable hydroxyl protecting groups can be used (P. G. M. Wuts, *Greene's Protective Groups in Organic Synthesis*, Wiley-Interscience, New York, 2014). In one embodiment, the protecting group R$_1$ and R$_2$ may be silyl groups, such as triakylsilyl groups (e.g. trimethylsilyl). The Wittig reagent can be of any salt, where X$^-$ can be Cl$^-$, Br$^-$, I$^-$, etc. Removal of the protecting groups R$_1$ and R$_2$ depends on the nature of the protecting groups. In one embodiment, the protecting group can be removed by the treatment with a fluoride.

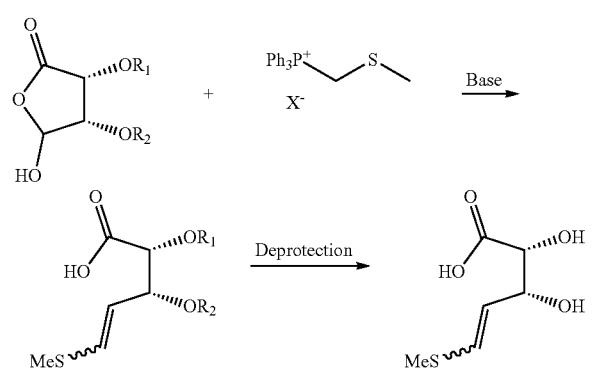

In another example of this general strategy, the starting material may be protected L-erythruronic acid. The carboxyl protecting group, R$_3$, may be a t-butyl group or a silyl group (e.g. tris(trimethylsilyl)silyl). Removal of the protecting groups, R$_1$, R$_2$ and R$_3$, depends on the nature of the protecting groups. In one embodiment, the protecting group can be removed by the treatment with a fluoride and/or an acid.

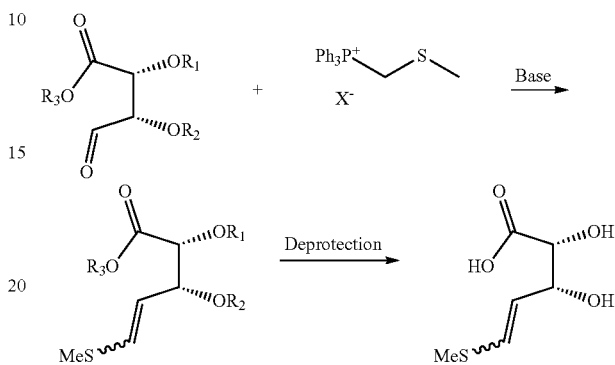

Method 3.

A general strategy for a third synthetic approach is represented below. (2R,3R)-2,3-dihydroxy-4-pentynoic acid or its protected form may be used as the starting molecule. Any suitable hydroxyl and carboxyl protecting groups can be used (P. G. M. Wuts, *Greene's Protective Groups in Organic Synthesis*, Wiley-Interscience, New York, 2014). In one embodiment, the protecting groups, R$_1$ and R$_2$, may be silyl groups, such as triakylsilyl groups (e.g. trimethylsilyl), and the carboxyl protecting group R$_3$ may be a t-butyl group or a silyl group (e.g. tris(trimethylsilyl)silyl). In one embodiment, an alkyne hydrothiolation reaction may be used in the synthetic approach. Alkyne hydrothiolation may be catalyzed by, for example, UV irradiation, a radical initiator, such as azobisisobutyronitrile (AIBN), cationic rhodium and iridium complexes, thorium and uranium complexes, rhodium complexes, caesium carbonate and/or gold. Removal of the protecting groups, R$_1$, R$_2$ and R$_3$, depends on the nature of the protecting groups. In one embodiment, the protecting group can be removed by the treatment with a fluoride and/or an acid.

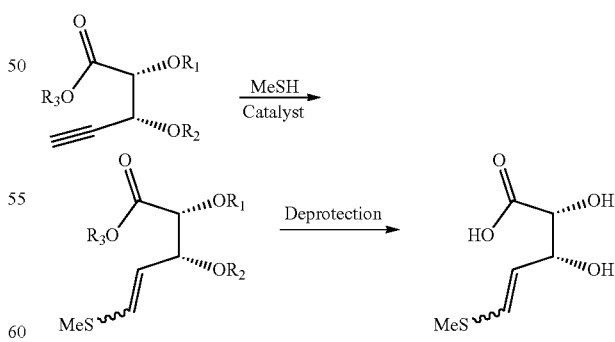

Example 3. LC-MS/MS Measurement of Compound A

A Waters Acquity UPLC system equipped with a binary solvent manager, a refrigerated sample manager (set at 12°

C.), and a column manager (set at 40° C.) was used for liquid chromatography with a reversed phase column (Waters ACQUITY UPLC® BEH C18, 1.7 μm, 2.1×100 mm). Mobile phase A was 0.1% formic acid in water and mobile phase B was 0.1% formic acid in acetonitrile. Linear gradient elution was carried out with an initial condition of 2% mobile phase B, which was held for 3.00 min. Mobile phase B was then increased to 98% in 0.40 min and maintained for 0.50 min. Mobile phase B reverted to 2% in 0.10 min for equilibration for next injection. The total run time was 5.00 min. A loop fixed aliquot of 5.0 μL of the final sample solution was injected for each sample. The flow rate was 350 μL/min and eluent was directly introduced into the electrospray source of a mass spectrometer. Strong needle wash (200 μL) was neat methanol and weak needle wash (600 μL) was a mixture of methanol and water (0.5:99.5). Seal wash was a mixture of methanol and water (10:90).

Mass spectrometry was performed using a Thermo Scientific Orbitrap Elite mass spectrometer equipped with a heated electrospray ionization (HESI-II) probe operated in negative mode. All masses were measured at high resolution, but reported simplified for clarity. The instrument was controlled by Orbitrap Elite™ 2.7 and XCalibur™ 2.2 software (later upgraded 3.0). The heated electrospray source was set with heater temperature at 430° C., sheath gas at 65, auxiliary gas flow rates at 15, sweep gas at 0, ion spray voltage at 3.25 kV, capillary temperature at 350° C., and S-lens RF level at 60%. A resolution of 30,000 was used to collect full scan FTMS spectra with mass range between m/z 100 and 600. All fragmentation experiments were set with scan range between m/z 50 and 200, resolution of 15,000, isolation width of 1.0, activation Q of 0.250, and activation time of 10.0 ms. All mass spectroscopic data were acquired and processed without any lock mass, and external mass calibration was used.

The normalized collision energy for MS$^2$ experiment was 28.0 eV for CID MS$^2$ experiment of m/z 177.02 and 100 eV for the corresponding HCD MS$^2$ experiments. The fragmention of parent ion with m/z of about 177.02 resulted in daughter ions with m/z of about 159, 133, 131, 129, 115, 113, 111, 101, 100, 99, 89, 85, 83, 75, 73, 57.03, 57.00, and 56. HCD generated three additional daughter ions with m/z of about 97, 87, and 74. For the CID MS$^3$ experiment of m/z 177.02/159.01, normalized collision energy was 26.0 and 25.0 eV for first and second stage fragmentation, respectively. For the HCD MS$^3$ experiment of m/z 177.02/159.01, normalized collision energy was 26.0 and 100 eV for first (CID) and second (HCD) stage fragmentation, respectively. For the CID MS$^3$ experiment of m/z 177.02/129.02, normalized collision energy was 28.0 and 25.0 eV for first and second stage fragmentation, respectively. For the CID MS$^3$ experiment of m/z 177.02/115.02, normalized collision energy was 28.0 and 30.0 eV for first and second stage fragmentation, respectively. For the CID MS$^3$ experiment of m/z 177.02/85.03, normalized collision energy was 28.0 and 21.0 eV for first and second stage fragmentation, respectively. For the HCD MS$^3$ experiment of m/z 177.02/85.03, normalized collision energy was 28.0 and 200 eV for first (CID) and second (HCD) stage fragmentation, respectively. The MS$^3$ fragmentation of m/z of about 177.02/159.01, 177.02/129.02, 177.02/115.02, and 177.02/85.03 resulted in two additional ions with m/z of about 84 and 67.

What is claimed is:

1. A compound represented by the following formula:

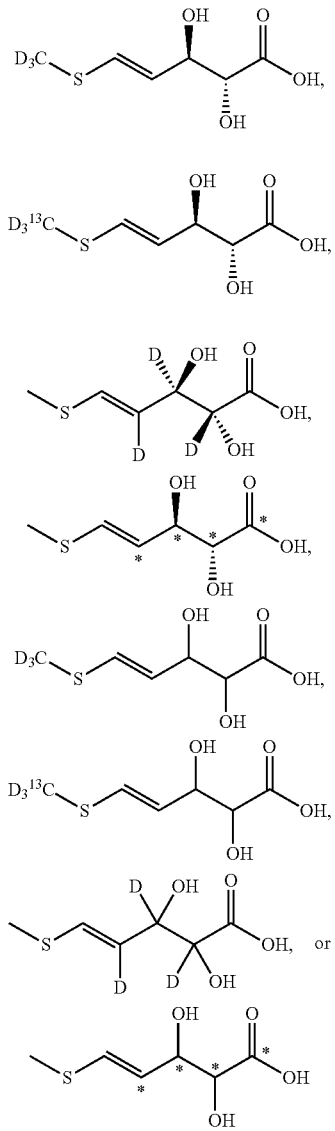

or a salt thereof, wherein *indicates $^{13}$C; and the compound is at least 60% pure.

2. A kit comprising a compound of claim 1, or a salt thereof, and instructions for measuring the level of the compound in a biological sample obtained from a subject.

3. A method for preparing a compound represented by the following formula:

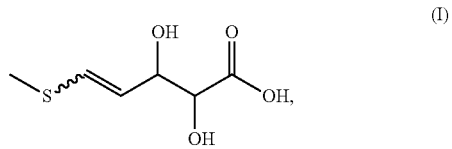

or a salt thereof, comprising the steps of:

a) reacting a compound represented by the following formula:

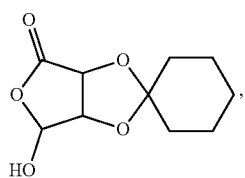

(V)

or a salt thereof, with a Wittig reagent R'$_3$P=CH$_2$SMe, wherein R' is Ph or an electron withdrawing group, to form a compound of formula (Va) or a salt thereof:

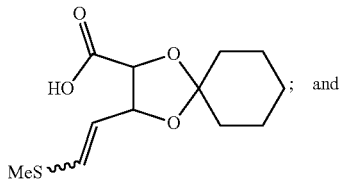

(Va)

b) deprotecting the compound of (Va) or a salt thereof to form a compound of formula (I) or a salt thereof.

4. The method of claim 3, wherein the method is for preparing a compound of formula (III):

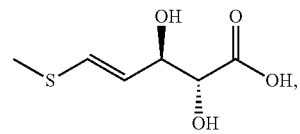

(III)

or a salt thereof, and wherein
(i) the method comprises the steps of:
a) reacting a compound of formula (VI) or a salt thereof:

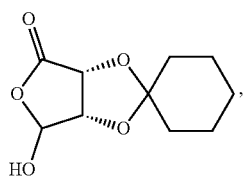

(VI)

with a Wittig reagent R'$_3$P=CH$_2$SMe, wherein R' is Ph or an electron-withdrawing group, to form a compound of formula (VIa) or a salt thereof:

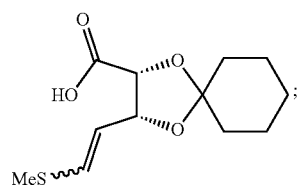

(VIa)

b) purifying the compound of (VIa) or a salt thereof to yield a compound of formula (VIb) or a salt thereof:

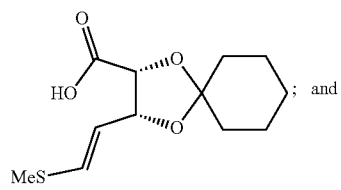

(VIb)

c) deprotecting the compound of formula (VIb) or a salt thereof to form the compound of formula (III) or a salt thereof; or (ii) the method comprises the steps of:
a) reacting a compound of formula (VI) or a salt thereof:

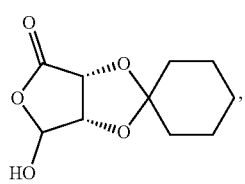

(VI)

with a Wittig reagent R'$_3$P=CH$_2$SMe, wherein R' is Ph or an electron-withdrawing group, to form a compound of formula (VIa) or a salt thereof:

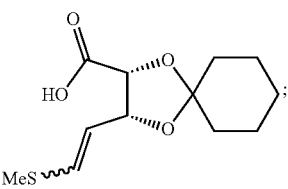

(VIa)

b) deprotecting the compound of formula (VIa) or a salt thereof to form a compound of formula (VIc) or a salt thereof:

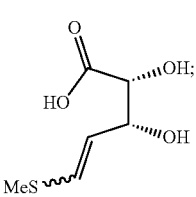

(VIc)

and c) purifying the compound of formula (VIc) or a salt thereof to yield the compound of formula (III) or a salt thereof.

5. A method of preparing a compound represented by the following formula:

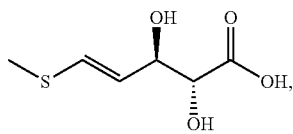
(III)

or a salt thereof, wherein
(i) the method comprises the steps of:
a) reacting a compound of formula (VII):

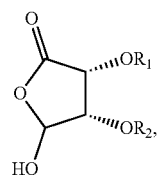
(VII)

or a salt thereof, with a Wittig reagent R'$_3$P=CH$_2$SMe, to form a compound of formula (VIIa),

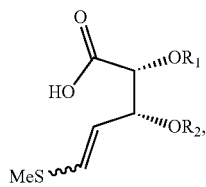
(VIIa)

or a salt thereof, wherein R' is Ph or an electon-withdrawing group, and R$_1$ and R$_2$ are each independently a silyl group;
b) purifying the compound of formula (VIIa) or a salt thereof, to yield a compound of formula (VIIb) or a salt thereof:

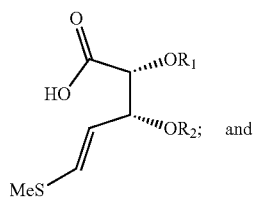
(VIIb)

c) deprotecting the compound of formula (VIIb) or a salt thereof to form the compound of formula (III) or a salt thereof; or (ii) the method comprises the steps of:
a) reacting a compound of formula (VII):

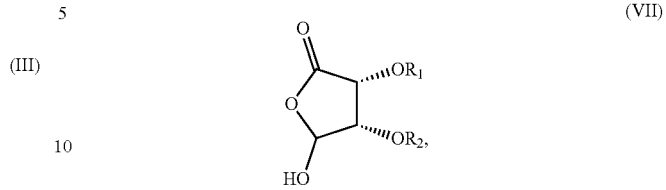
(VII)

or a salt thereof, with a Wittig reagent R'$_3$P=CH$_2$SMe, to form a compound of formula (VIIa) or a salt thereof,

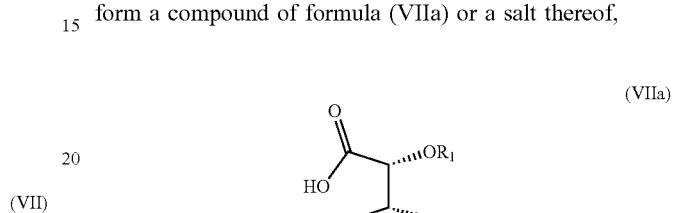
(VIIa)

wherein R' is Ph or an electon-withdrawing group, and R$_1$ and R$_2$ are each independently a silyl group;
b) deprotecting the compound of formula (VIIa) or a salt thereof to form a compound of formula (VIIc) or a salt thereof:

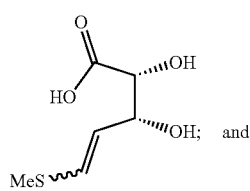
(VIIc)

c) purifying the compound of formula (VIIc) or a salt thereof to yield the compound of formula (III) or a salt thereof.

6. A method of preparing a compound represented by the following formula:

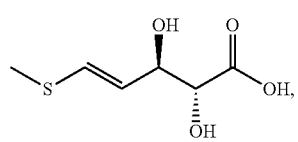
(III)

or a salt thereof, wherein
(i) the method comprises the steps of:
a) reacting a compound of formula (IX):

(IX)

with methanethiol to form a compound of formula (VIIIa) or a salt thereof:

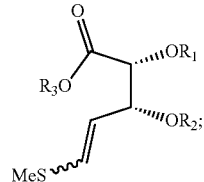
(VIIIa)

b) purifying the compound of formula (VIIIa) or a salt thereof to yield a compound of formula (VIIIb) or a salt thereof:

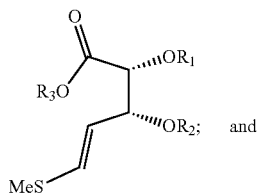
(VIIIb)

and c) deprotecting the compound of formula (VIIIb) or a salt thereof to form the compound of formula (III) or a salt thereof, or (ii) the method comprises the steps of:

a) reacting a compound of formula (IX):

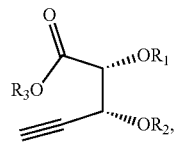
(IX)

with methanethiol to form a compound of formula (VIIIa) or a salt thereof:

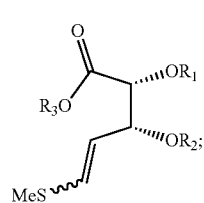
(VIIIa)

b) deprotecting the compound of formula (VIIIa) or a salt thereof to form a compound of formula (VIIIb) or a salt thereof:

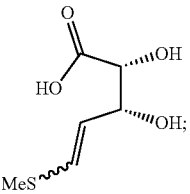
(VIIIb)

c) purifying the compound of formula (VIIIb) or a salt thereof to yield the compound of formula (III) or a salt thereof, wherein:

$R_1$ and $R_2$ are each independently a silyl group and $R_3$ is a t-butyl group or a silyl group.

7. The method of claim 4, wherein the method comprises the steps of:

a) reacting a compound of formula (VI) or a salt thereof:

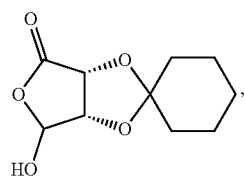
(VI)

with a Wittig reagent $R'_3P{=}CH_2SMe$, wherein R' is Ph or an electron-withdrawing group, to form a compound of formula (VIa) or a salt thereof:

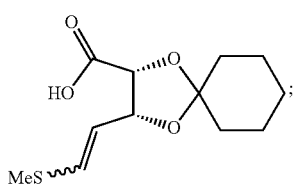
(VIa)

b) purifying the compound of (VIa) or a salt thereof to yield a compound of formula (VIb) or a salt thereof:

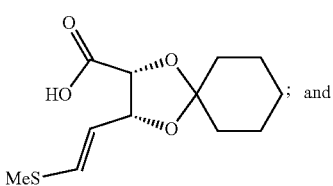
(VIb)

; and c) deprotecting the compound of formula (VIb) or a salt thereof to form the compound of formula (III) or a salt thereof.

8. The method of claim 4, wherein the method comprises the steps of:

a) reacting a compound of formula (VI) or a salt thereof:

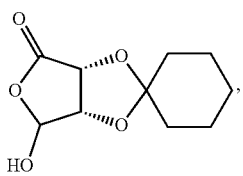
(VI)

with a Wittig reagent R'$_3$P=CH$_2$SMe, wherein R' is Ph or an electron-withdrawing group, to form a compound of formula (VIa) or a salt thereof:

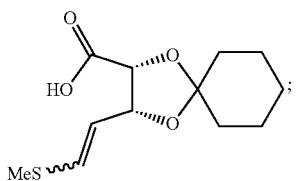
(VIa)

b) deprotecting the compound of formula (VIa) or a salt thereof to form a compound of formula (VIc) or a salt thereof:

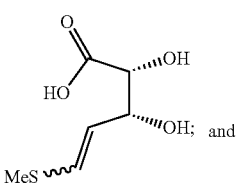
(VIc)

c) purifying the compound of formula (VIc) or a salt thereof to yield the compound of formula (III) or a salt thereof.

9. The method of claim 5, wherein the method comprises the steps of:

a) reacting a compound of formula (VII):

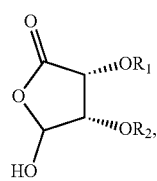
(VII)

or a salt thereof, with a Wittig reagent R'$_3$P=CH$_2$SMe, to form a compound of formula (VIIa),

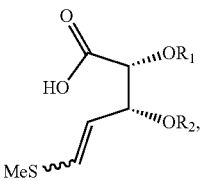
(VIIa)

or a salt thereof, wherein R' is Ph or an electron-withdrawing group, and R$_1$ and R$_2$ are each independently a silyl group;

b) purifying the compound of formula (VIIa) or a salt thereof, to yield a compound of formula (VIIb) or a salt thereof:

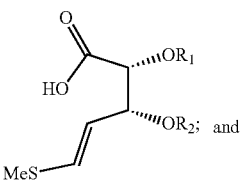
(VIIb)

c) deprotecting the compound of formula (VIIb) or a salt thereof to form the compound of formula (III) or a salt thereof.

10. The method of claim 5, wherein the method comprises the steps of:

a) reacting a compound of formula (VII):

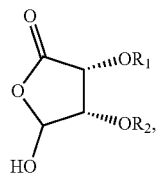
(VII)

or a salt thereof, with a Wittig reagent R'$_3$P=CH$_2$SMe, to form a compound of formula (VIIa) or a salt thereof,

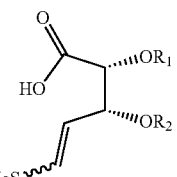
(VIIa)

wherein R' is Ph or an electron-withdrawing group, and R$_1$ and R$_2$ are each independently a silyl group;

b) deprotecting the compound of formula (VIIa) or a salt thereof to form a compound of formula (VIIc) or a salt thereof:

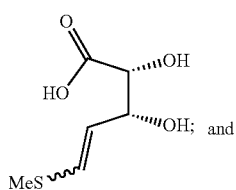

(VIIc)

c) purifying the compound of formula (VIIc) or a salt thereof to yield the compound of formula (III) or a salt thereof.

11. The method of claim 6, wherein the method comprises the steps of:

a) reacting a compound of formula (IX):

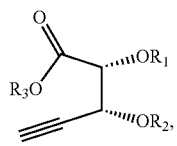

(IX)

with methanethiol to form a compound of formula (VIIIa) or a salt thereof:

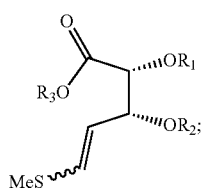

(VIIIa)

b) purifying the compound of formula (VIIIa) or a salt thereof to yield a compound of formula (VIIIb) or a salt thereof:

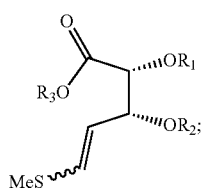

(VIIIb)

c) deprotecting the compound of formula (VIIIb) or a salt thereof to form the compound of formula (III) or a salt thereof.

12. The method of claim 6, wherein the method comprises the steps of:

a) reacting a compound of formula (IX):

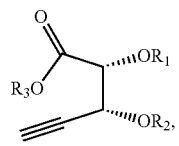

(IX)

with methanethiol to form a compound of formula (VIIIa) or a salt thereof:

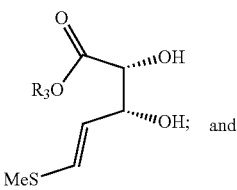

(VIIIa)

b) deprotecting the compound of formula (VIIIa) or a salt thereof to form a compound of formula (VIIIb) or a salt thereof:

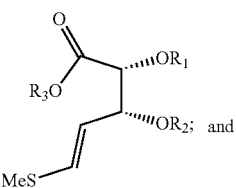

(VIIIb)

c) purifying the compound of formula (VIIIb) or a salt thereof to yield the compound of formula (III) or a salt thereof.

13. The compound of claim 1, wherein the compound is represented by the following formula:

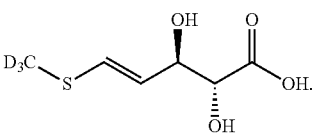 [SMILES: [2H]C([2H])([2H])S/C=C/[C@@H](O)[C@@H](O)C(=O)O]

14. The compound of claim 1, wherein the compound is represented by the following formula:

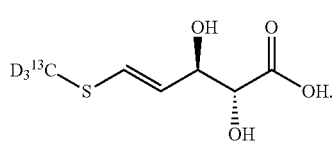

15. The compound of claim 1, wherein the compound is represented by the following formula:

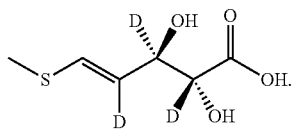

16. The compound of claim 1, wherein the compound is represented by the following formula:

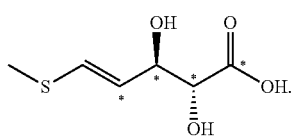

17. The compound of claim 1, wherein the compound is represented by the following formula:

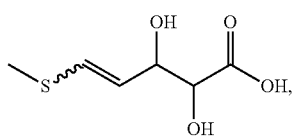

18. The compound of claim 1, wherein the compound is represented by the following formula:

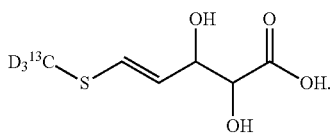

19. The compound of claim 1, wherein the compound is represented by the following formula:

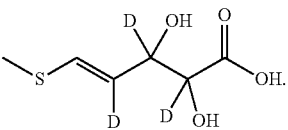

20. The compound of claim 1, wherein the compound is represented by the following formula:

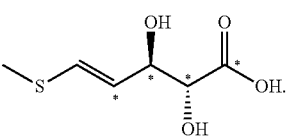

* * * * *

UNITED STATES PATENT AND TRADEMARK OFFICE
CERTIFICATE OF CORRECTION

PATENT NO. : 11,680,042 B2  
APPLICATION NO. : 16/650429  
DATED : June 20, 2023  
INVENTOR(S) : Qibo Zhang Page 1 of 1

It is certified that error appears in the above-identified patent and that said Letters Patent is hereby corrected as shown below:

In the Claims

At Column 61, Claim number 17, Lines 25-30, please replace the following structure:

" 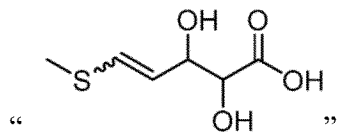 "

With:

-- 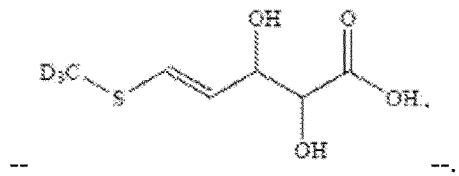 --.

Signed and Sealed this  
Nineteenth Day of September, 2023

Katherine Kelly Vidal  
*Director of the United States Patent and Trademark Office*